US009789012B2

(12) United States Patent
Chmielewski et al.

(10) Patent No.: US 9,789,012 B2
(45) Date of Patent: Oct. 17, 2017

(54) ABSORBENT ARTICLE WITH MULTI-LAYER FOLDED ABSORBENT CORE

(71) Applicant: Attends Healthcare Products, Inc., Greenville, NC (US)

(72) Inventors: Harry Chmielewski, Raleigh, NC (US); Paul Ducker, St. Simons Island, GA (US); Jacob Vrooman, Moon, VA (US); Thomas Kaiser, Marion, OH (US); Tim Sergeant, Winterville, NC (US)

(73) Assignee: ATTENDS HEALTHCARE PRODUCTS, INC., Greenville, NC (US)

( * ) Notice: Subject to any disclaimer, the term of this patent is extended or adjusted under 35 U.S.C. 154(b) by 30 days.

(21) Appl. No.: 14/634,718

(22) Filed: Feb. 27, 2015

(65) Prior Publication Data
US 2015/0245958 A1 Sep. 3, 2015

Related U.S. Application Data

(60) Provisional application No. 61/948,744, filed on Mar. 6, 2014, provisional application No. 61/946,595, filed on Feb. 28, 2014.

(51) Int. Cl.
*A61F 13/535* (2006.01)
*A61F 13/534* (2006.01)
*A61F 13/53* (2006.01)

(52) U.S. Cl.
CPC .. *A61F 13/53427* (2013.01); *A61F 13/53409* (2013.01); *A61F 2013/5355* (2013.01); *A61F 2013/530883* (2013.01)

(58) Field of Classification Search
CPC .............. A61F 13/534; A61F 13/53409; A61F 13/53427; A61F 13/535; A61F 13/53752;
(Continued)

(56) References Cited

U.S. PATENT DOCUMENTS 3,699,966 A * 10/1972 Chapuis ............ A61F 13/53418
604/377
4,576,596 A * 3/1986 Jackson ............ A61F 13/53418
604/370
(Continued)

FOREIGN PATENT DOCUMENTS

WO 99/49826 10/1999
WO 2013126934 A1 9/2013

OTHER PUBLICATIONS

International Preliminary Report on Patentability for PCT/US2015/018198 issued Sep. 15, 2016.
(Continued)

*Primary Examiner* — Lynne Anderson
(74) *Attorney, Agent, or Firm* — Norton Rose Fulbright US LLP

(57) ABSTRACT

Absorbent laminates and multi-layer, folded absorbent cores comprising the absorbent laminates for use in absorbent articles are presented. Specifically, multi-layer, folded absorbent cores are presented that are formed from an absorbent laminate comprising an absorbent layer between two tissue layers, in which the absorbent core includes a central channel running longitudinally along the core and crenellations profiled along the thickness of the core and providing enhanced liquid distribution across the core surface area or profile and improved liquid absorption into the laminate.

34 Claims, 39 Drawing Sheets

(58) Field of Classification Search
CPC ........ A61F 2013/530547; A61F 2013/530554;
A61F 2013/530883; A61F 2013/534455;
A61F 2013/53472; A61F 2013/5355
See application file for complete search history.

(56) References Cited

U.S. PATENT DOCUMENTS

| | | | | |
|---|---|---|---|---|
| 4,731,071 | A * | 3/1988 | Pigneul | ................. A61F 5/4401 |
| | | | | 604/368 |
| 5,649,916 | A * | 7/1997 | DiPalma | ............... A61F 13/534 |
| | | | | 604/365 |
| 6,632,209 | B1 * | 10/2003 | Chmielewski | .... A61F 13/49406 |
| | | | | 604/378 |
| 6,794,557 | B1 * | 9/2004 | Klemp | .............. A61F 13/49426 |
| | | | | 442/84 |
| 8,021,998 | B2 | 9/2011 | Qin et al. | |
| 2003/0105442 | A1 | 6/2003 | Johnston et al. | ............. 604/368 |
| 2003/0158531 | A1 | 8/2003 | Chmielewski | ................ 604/366 |
| 2005/0215962 | A1 | 9/2005 | Litvay et al. | |
| 2010/0198178 | A1 | 8/2010 | Litvay | ........................... 604/365 |
| 2012/0316526 | A1 | 12/2012 | Rosati et al. | |

OTHER PUBLICATIONS

Extended European Search Report issued in European Application No. 15754606.0, dated Aug. 25, 2017.

* cited by examiner

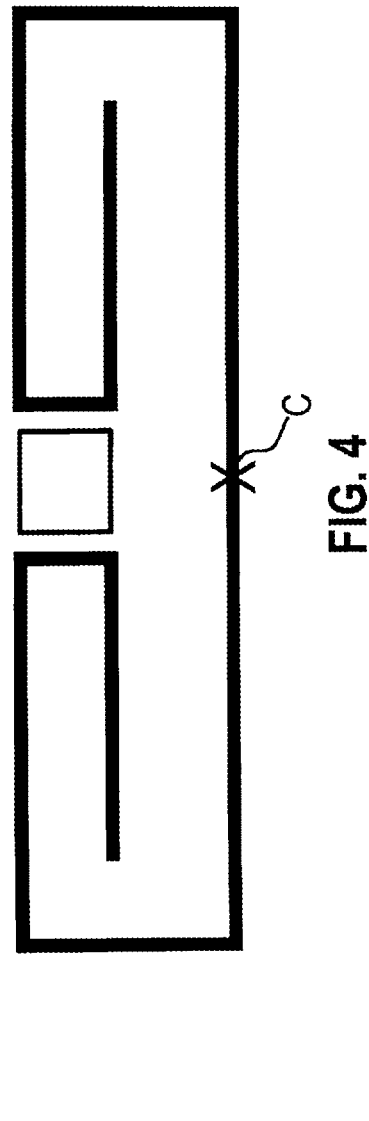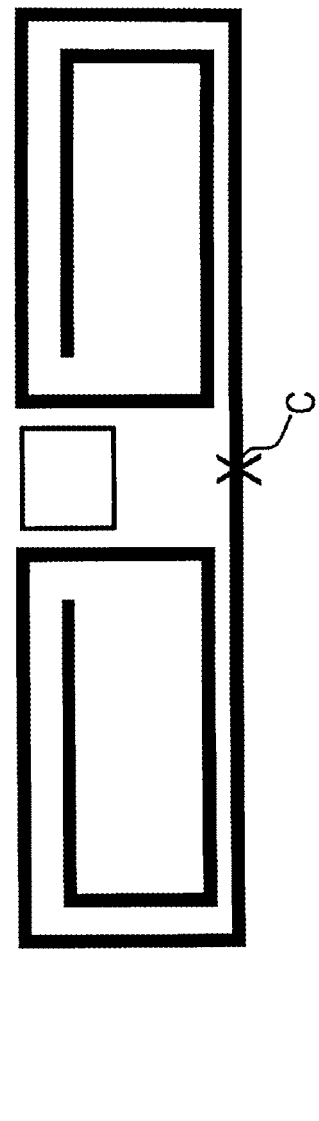
FIG. 4
FIG. 5

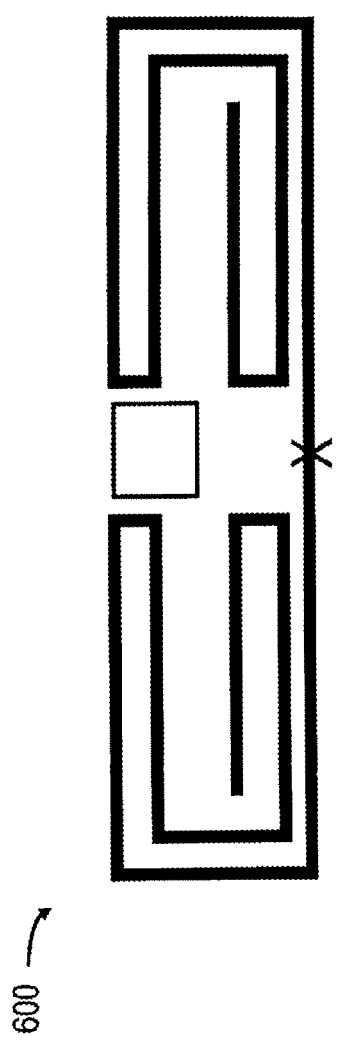
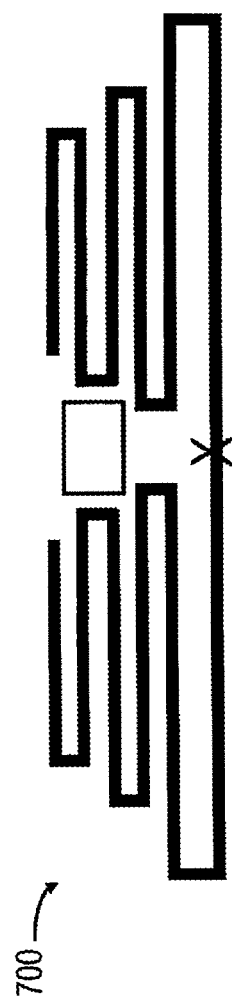
FIG. 6
FIG. 7

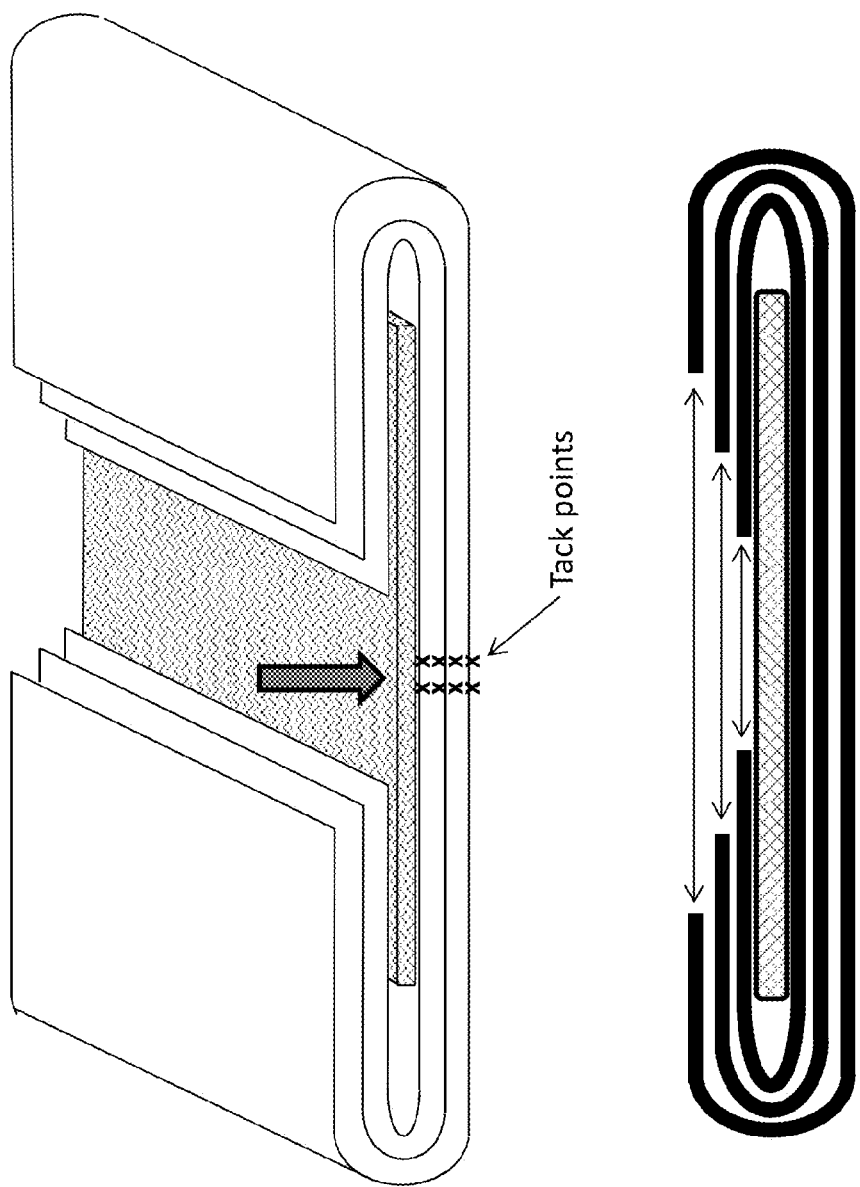

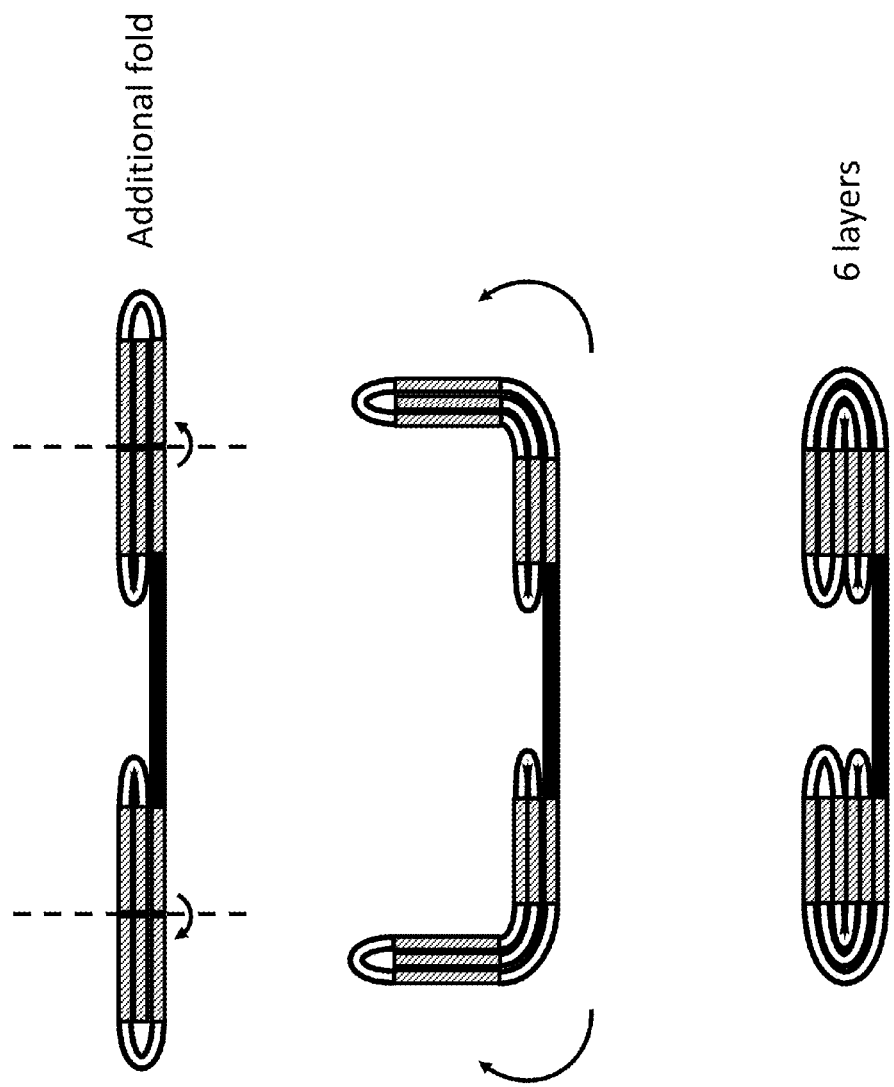

| SAP TYPE | CORE STRUCTURE | SAP SFC (g/g) | SAP SFC (60 cm) (g/g) | SAP 07 AAP (g/g) | SAP 07 RDL (g/g) | SAP EFF (%) |
|---|---|---|---|---|---|---|
| W211 | 1-Layer | 42 | 0 | 9.1 | 38.7 | 24% |
| W211 | 6-Layer | 42 | 0 | 18.3 | 35.9 | 50% |
| S125D | 1-Layer | 34.5 | >0-10 | 14.4 | 32.8 | 48% |
| S125D | 6-Layer | 34.5 | >0-10 | 24.7 | 32.9 | 75% |
| W112A | 1-Layer | 34 | >0-10 | 13.6 | 34.8 | 48% |
| W112A | 6-Layer | 34 | >0-10 | 23.3 | 31.9 | 70% |
| T9030 | 1-Layer | 30 | >0-10 | 16.5 | 30.8 | 56% |
| T9030 | 6-Layer | 30 | >0-10 | 16.2 | 30.6 | 59% |
| T7075 | 1-Layer | 28 | 10-20 | 19.0 | 29.8 | 64% |
| T7075 | 6-Layer | 28 | 10-20 | 18.5 | 29.3 | 62% |

FIG. 18

Chassis
4-Factor, 2-Level
DOE #1

| Factors | Levels |
|---|---|
| 1. ADL | 215 x 110 mm 60 gsm TAB |
| | 197 x 65 mm 50 gsm TAB |
| 2. Channel Nonwoven | 180 gsm TAB |
| | None |
| 3. Core | One-Part: 345 x 110 mm with 6-45 gsm W211 |
| | Two-Part:<br>Surge – 215 x 110 mm with 6-60 S125D<br>Base – 345 x 110 mm with 1-89 gsm W211 |
| 4. Time between doses | 2 min. |
| | 30 min. |
| Constant: 50 mm tackdown | |

Chassis
4-Factor, 2-Level
DOE #2

| Factors | Levels | | | |
|---|---|---|---|---|
| 1. ADL Length | 103 mm 40 gsm TAB | | | |
| | 215 mm 40 gsm TAB | | | |
| 2. ADL Width | 65 gsm 40 gsm TAB | | | |
| | 110 gsm 40 gsm TAB | | | |
| 3. ADL Offset | 0 | | | |
| | 25 mm | | | |
| 4. Tackdown | 0 | | | |
| | 75 mm | | | |
| Constant: One-Part Core: 345 x 100 mm with 6-45 gsm W211 | | | | |

Chassis
4- Factor, 2-Level
DOE #3

| Factors | Levels |
|---|---|
| 1. ADL Length | 149 mm 40 gsm TAB |
| | 215 mm 40 gsm TAB |
| 2. Tackdown | 0 |
| | 25 mm |
| 3. ADL Offset | 25 mm |
| | 50 mm |
| 4. Laminate SAP BW | 45 gsm |
| | 60 gsm |

Constant: One-Part Core: 345 x 100 mm & ADL Width 110 mm

ABSORBENT ARTICLE WITH MULTI-LAYER FOLDED ABSORBENT CORE

I. CROSS-REFERENCE TO RELATED APPLICATIONS

This application claims priority to U.S. Provisional Patent Application Ser. No. 61/946,595, filed on Feb. 28, 2014, and to U.S. Provisional Patent Application Ser. No. 61/948,744, filed on Mar. 6, 2014, each of which is hereby incorporated by reference in its entirety.

II. FIELD OF THE INVENTION

The present invention relates generally to absorbent garments and, particularly, absorbent garments having multi-layer folded thin absorbent cores.

III. BACKGROUND

Absorbent articles, such as baby diapers, training pants, adult incontinence products and other such absorbent products include a topsheet that is closest to the wearer, an outer, moisture-impermeable backsheet, and an absorbent core. Over time the absorbent cores have become increasingly thinner with superabsorbent materials being included in ever-increasing amounts in place of traditional cellulosic pulp and other fillers and absorbents. While these thinner, superabsorbent-containing cores provide advantages, such as, generally offering a better fit to the wearer, they also present various challenges. One such challenge relates to the acquisition and distribution of liquid insults. In conventional core designs the liquid spreads radially from the point where it strikes, or insults, the core. Thus, rather than being dispersed across the core surface generally, its transport is localized. This challenge is exacerbated by the issue of gel blocking. Gel blocking refers to the blocking of liquid transport through the core by the swelling and gelling of the superabsorbent material as it absorbs and retains liquid and swells. Gel blocking often leads to leakage from the absorbent article since the core does not have the ability to absorb and retain liquid at the rate desired.

Prior designs have attempted, to varying degrees of success and in a variety of ways, to address these issues. These efforts have involved the selection of superabsorbent materials based on the materials' properties, the addition of acquisition and distribution layers on top of the cores, and the positioning of the superabsorbent materials in the core in a variety of designs and arrangements.

The preferred embodiments discussed below seek to address some of these disadvantages in the prior art.

IV. SUMMARY OF THE INVENTION

The present invention relates generally to absorbent garments and, particularly, to thin, multi-layer folded absorbent cores for disposable absorbent garments having improved absorbent properties, including rapid liquid acquisition, good core utilization and high SAP efficiency The multi-layer folded absorbent core according to the present invention comprises an absorbent laminate that is folded in such a manner as to present a central channel and multiple liquid pathways for greatly enhanced distribution and acquisition of liquid within the core.

In accordance with one aspect of the present invention, there is provided an absorbent core comprising an upper laminate layer, a lower laminate layer and an absorbent layer positioned between the upper laminate layer and the lower laminate layer, the absorbent layer comprising greater than about 90 percent by weight super absorbent polymer (SAP).

In certain aspects, the absorbent core further comprises a third laminate layer between the upper laminate layer and the lower laminate layer. In some embodiments, the third layer is disposed between the upper laminate layer and the absorbent layer. In still other embodiments, the third laminate layer is disposed between the absorbent layer and the lower laminate layer.

In specific embodiments, the longitudinally folded absorbent laminate comprises a channel, which in certain other embodiments, is generally centrally located relative to a longitudinal centerline. In other embodiments, the channel extends along the length of the folded laminate. In yet other embodiments, the channel includes a channel insert. In certain aspects, the channel insert is a material selected from group consisting of tow fibers, nonwoven, and yarn. In still other aspects, the channel insert comprises a material selected from group consisting of tow fibers, nonwoven, and yarn.

The longitudinally folded absorbent laminate preferably comprises at least two laminate layers on each side of the channel. In certain embodiments, the two laminate layers on each side of the channel essentially form two 'V' structures, with the bottom side of each 'V' structure joined to form the bottom of the channel and the top side of the 'V' structures are not joined, and form the top of the open channel. In still other aspects, the longitudinally folded absorbent laminate includes at least two laminate layers on each side of the channel, and when unfolded and generally flat, the laminate is at least about 180% the width of the folded absorbent laminate.

In certain aspects, at least one of the upper laminate layer and the lower laminate layer of the folded absorbent laminate comprises a tissue. In certain aspects, at least one of the upper laminate layer and the lower laminate layer of the folded absorbent laminate comprises tissue selected from the group of tissues consisting of porous tissue, creped tissue, and standard tissue. In still other embodiments, at least one of the upper laminate layer or the lower laminate layer of the folded absorbent laminate comprises a synthetic nonwoven.

In certain aspects, the upper and lower laminate layers of the folded absorbent laminate are bonded to each other through non-adhesive bonding. In yet other aspects, the folded absorbent laminate further comprises an adhesive between the upper and lower laminate layers. In specific embodiments, the adhesive is applied between the upper laminate layer and the lower laminate layer. In certain aspects, the adhesive extends along at least one longitudinal edge of the laminate such that the upper laminate layer is adhered to the lower laminate layer.

In some aspects, the adhesive basis weight is less than about 10% of the SAP basis weight. In yet other embodiments, the adhesive is selected from a group consisting of styrene-butadiene-styrene block copolymer (SBS) or styrene-isoprene-styrene (SIS).

In specific embodiments, the absorbent laminate of the absorbent core is folded to form a longitudinally folded multi-layer absorbent laminate of at least three layers and, in other embodiments laminates having four, five, six, seven, eight or nine layers. In still other aspects, the multi-layer absorbent laminate is part of a dual core. The dual core may comprise a base core and a surge core, wherein the base core and/or the surge core includes a longitudinally folded, multi-layer absorbent laminate as described in the present application. In yet other aspects, the surge core and/or base core can include a longitudinally folded, multi-layer absorbent laminate further comprises a channel. In specific embodiments, the channel is generally centrally located relative to the laminate width. In still other specific embodiments, the channel width is from about 2 mm to about 50 mm wide.

In specific embodiments, the multi-layer absorbent laminate is part of a dual core comprising a base core and a surge core. In certain embodiments, both the base core and the surge core comprise a longitudinally folded, multi-layer absorbent laminate. In specific embodiments, the surge core is nested within the channel of the base core. In yet other embodiments, the surge core is nested within the channel of the base core such that two additional channels are formed between the edges of the surge and the base core, thereby forming three total channels.

In certain aspects, the SAP in the absorbent core has centrifuge retention capacity (CRC) in the range of about 33-38 g/g. In certain aspects, the SAP in the absorbent core has a 0.7 SAP AAP, as measured in the 6-layer laminate test, of at least about 20 g/g.

In yet still other embodiments, the SAP has a mean particle size in the range of about 250 μm to about 350 μm. In specific embodiments, less than 10% of the weight of the SAP particles reside in particles that are greater than 500 μm. In certain aspects, the SAP is non-uniformly distributed. In specific embodiments, a SAP with an absorption time between about 160 to about 220 seconds is used. In specific embodiments, the resultant asymmetry of the absorbent laminate is between about 1 and about 2. In still other embodiments, SAP with an absorption time less than about 160 seconds is used and the resultant asymmetry is greater than about 4.

In specific embodiments, the SAP content of each layer of the multi-layer folded absorbent laminate is from about 40 gsm to about 150 gsm. In still other embodiments, the total SAP content of the multi-layers of the folded laminate is from about 7.4 g. to about 18 g. In still other embodiments the total SAP content of the multi-layers of the folded laminate is between about 240 gsm to about 600 gsm.

In certain aspects, the core comprising the longitudinally folded, multi-layer absorbent laminate has a thickness of less than about 5 mm and, in other aspects, 4 mm, 3 mm or 2 mm.

In specific aspects, the core has side leakage that is less than about 5 g.

In certain embodiments, the absorbent layer comprises a single layer of SAP.

In still other embodiments, the absorbent laminate exhibits a 2 ml Free Surface Absorption Time of less than about 10 seconds.

In accordance with other aspects of the present invention, there is provided a disposable absorbent article comprising a body-facing topsheet, a backsheet and an absorbent core comprising any of the longitudinally folded, multi-layer absorbent laminates of the present application.

In certain aspects, the disposable absorbent article further comprises a through-air bonded (TAB) acquisition distribution layer (ADL) positioned between the topsheet and the absorbent core. In specific aspects, the ADL width is a least 80% of folded core width.

In still other aspects, a layer of cellulosic acquisition fiber is positioned between the topsheet of the absorbent article and the absorbent core. In embodiments in which the cellulosic acquisition fiber layer is included and contains SAP, the amount of SAP is no more than 10% by weight SAP.

In certain aspects, the disposable absorbent article and the core are stable after an insult. In certain aspects, the core and the absorbent article have a stability rating of at least 35 drops.

In accordance with another aspect of the present invention, there is provided an absorbent core comprising a longitudinally folded multi-layer absorbent laminate, the absorbent laminate comprising an upper laminate layer, a lower laminate layer, and an absorbent layer positioned between the upper laminate layer and the lower laminate layer, the absorbent layer containing SAP, wherein the absorbent laminate is folded to form a longitudinally folded multi-layer absorbent laminate of at least three layers. In some aspects, the SAP content of each layer of the multi-layer folded absorbent laminate is from about 40 gsm to about 150 gsm. In other aspects, the total SAP content of the multi-layers of the folded laminate is from about 7.4 g. to about 18 g. In still other aspects, the total SAP content of the multi-layers of the folded laminate is between about 240 gsm to about 600 gsm. In other aspects still, the 0.7 psi AAP of the folded laminate is greater than the 0.7 psi AAP of the same total basis weight of SAP.

In some embodiments, the absorbent core further comprises a channel extending longitudinally along the folded absorbent laminate, a first set of laminate layers positioned on one side of the channel and a second set of laminate layers positioned on the other side of the channel. In certain embodiments, the absorbent core comprises a plurality of liquid passageways positioned between the laminate layers.

In certain embodiments of the absorbent core, the folded absorbent laminate has an interior interfacial area for liquid absorption that is greater than one and one half times the surface area of the top surface of the folded laminate. In other embodiments of the absorbent core, certain of the liquid passageways open toward the central channel and certain other of the liquid passageways open toward the sides of the folded laminate.

In still other embodiments of the absorbent core, at least one liquid passageway is positioned between the laminate layers and is open to the channel that is at least 2 millimeters wide. In other aspects, the channel is no greater than about 50 millimeters wide. In other aspects still, the absorbent core comprises a folded laminate that, when unfolded and generally flat, is at least about 150% the width of the folded absorbent laminate when folded.

In specific aspects of the absorbent core, at least one liquid passageway of the longitudinally folded absorbent laminate is positioned between the laminate layers and open to the channel such that liquid flows away from the channel passing radially from the channel into the laminate layers. In other embodiments, the absorbent core comprises at least four laminate layers on each side of the channel. In specific embodiments, the absorbent core comprises a folded laminate that, when unfolded and generally flat, is at least about 345% the width of the folded absorbent laminate.

In certain aspects, the folded core comprises an absorbent layer comprising SAP. In certain aspects, the folded core comprises an absorbent layer comprising, in addition to SAP, an adhesive positioned between the upper laminate layer and lower laminate layer holding the upper and lower laminate layers together. In still other embodiments, the adhesive comprises or is mixed with the SAP.

In still other embodiments, the longitudinally folded absorbent laminate of an absorbent core comprises at least six laminate layers. In certain embodiments, the longitudinally folded absorbent laminate of an absorbent core comprises at least six laminate layers on each side of a channel.

In specific embodiments, when the folded laminate, when unfolded and generally flat, is at least about 475% the width of the folded absorbent laminate.

In certain aspects, the longitudinally folded absorbent laminate of an absorbent core has at least one liquid passageway positioned between the laminate layers and open to a channel. In certain aspects, the longitudinally folded absorbent laminate of an absorbent core has at least two liquid passageways positioned between the laminate layers. In some aspects, at least one of the two passageways is open to a channel. In certain aspects, the longitudinally folded absorbent laminate of an absorbent core folded has an interior interfacial area for liquid absorption that is greater than two times the surface area of the top surface of the folded laminate.

In certain aspects, the longitudinally folded absorbent laminate of an absorbent core has incorporated therein free volume articles. In some embodiments, the free volume articles are fibers and Discrete Acquisition Cells. In other aspects, during use and liquid absorption, the free volume articles provide relatively high free volume within the laminate to provide better liquid access to the SAP. In some aspects, the Discrete Acquisition Cells are selected from the group consisting of particles of compressed cellulose sponge, creped cellulosic paper, soy bean hulls, and clumps of fiber such as wood pulp and cellulosic fluff bonded with adhesive, and the fibers are selected from the group consisting of continuous filament tow, staple fiber tow, continuous filament yarn, and staple fiber yarn. In still other embodiments, the absorbent layer comprises greater than about 40 percent by weight SAP.

In accordance with yet another aspect of the present invention, there is provided an absorbent core comprising a longitudinally folded multi-layer absorbent laminate, the absorbent laminate comprising a substrate laminate layer and an absorbent layer positioned and adhered on the substrate laminate layer, the absorbent layer containing SAP, wherein the absorbent laminate is folded to form a longitudinally folded multi-layer absorbent laminate of at least three layers.

V. BRIEF DESCRIPTION OF THE DRAWINGS

The following drawings illustrate by way of example and not limitation. For the sake of brevity and clarity, every feature of a given structure may not be labeled in every figure in which that structure appears. Identical reference numbers do not necessarily indicate an identical structure. Rather, the same reference number may be used to indicate a similar feature or a feature with similar functionality, as may non-identical reference numbers.

FIG. 4 is a schematic view of a 3-layer folded absorbent laminate according to one aspect of the present invention.

FIG. 5 is a schematic view of a 4-layer folded absorbent laminate according to another aspect of the present invention.

FIG. 6 is a schematic view of a 5-layer folded absorbent laminate according to another aspect of the present invention.

FIG. 7 is a schematic view of a multi-layer folded absorbent laminate according to another aspect of the present invention.

FIG. 8 schematically illustrates a folded core with a terraced central channel comprised of separate layers of laminate encapsulating an optional acquisition material in the interior of the core.

FIGS. 9A-9E illustrate schematically folding schemes for forming 3-layer, 4-layer, 5-layer and 6-layer folded cores.

Figure 10A:
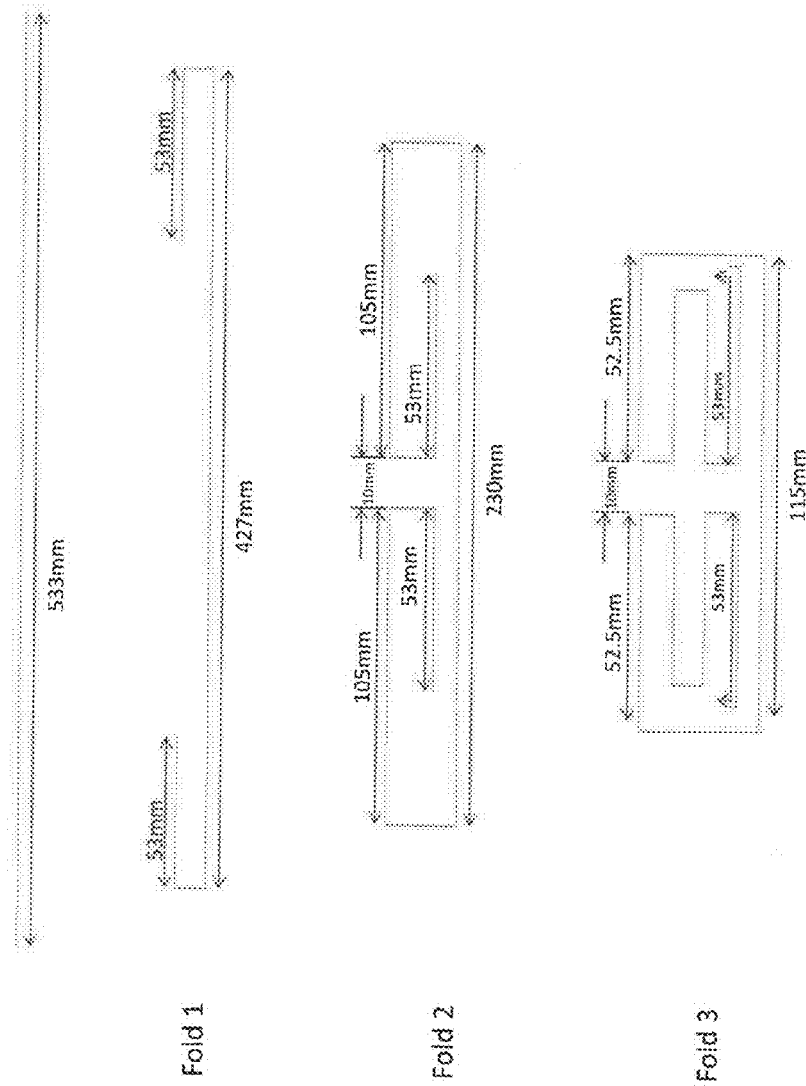

FIG. 10A is a schematic view of a particular 5-layer folded laminate according to an example; 10B illustrates the relation between core width and channel width for a 533 mm width sheet.

Figure 11:
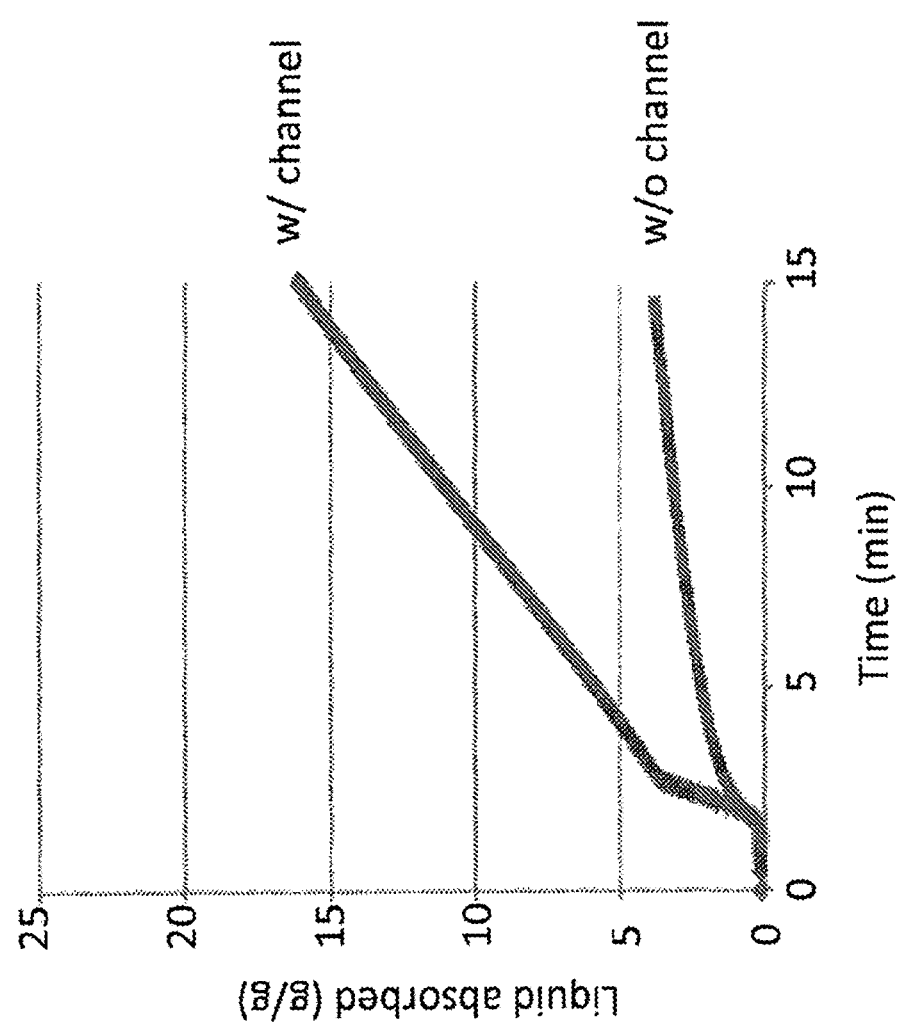

FIG. 11 is a chart reporting the results of a demand absorbency experiment performed on a Gravimetric Absorbency Test System (GATS) comparing a multi-layer folded core according to one embodiment of the present invention to a sample that does not include the novel features of the present invention.

Figure 12:
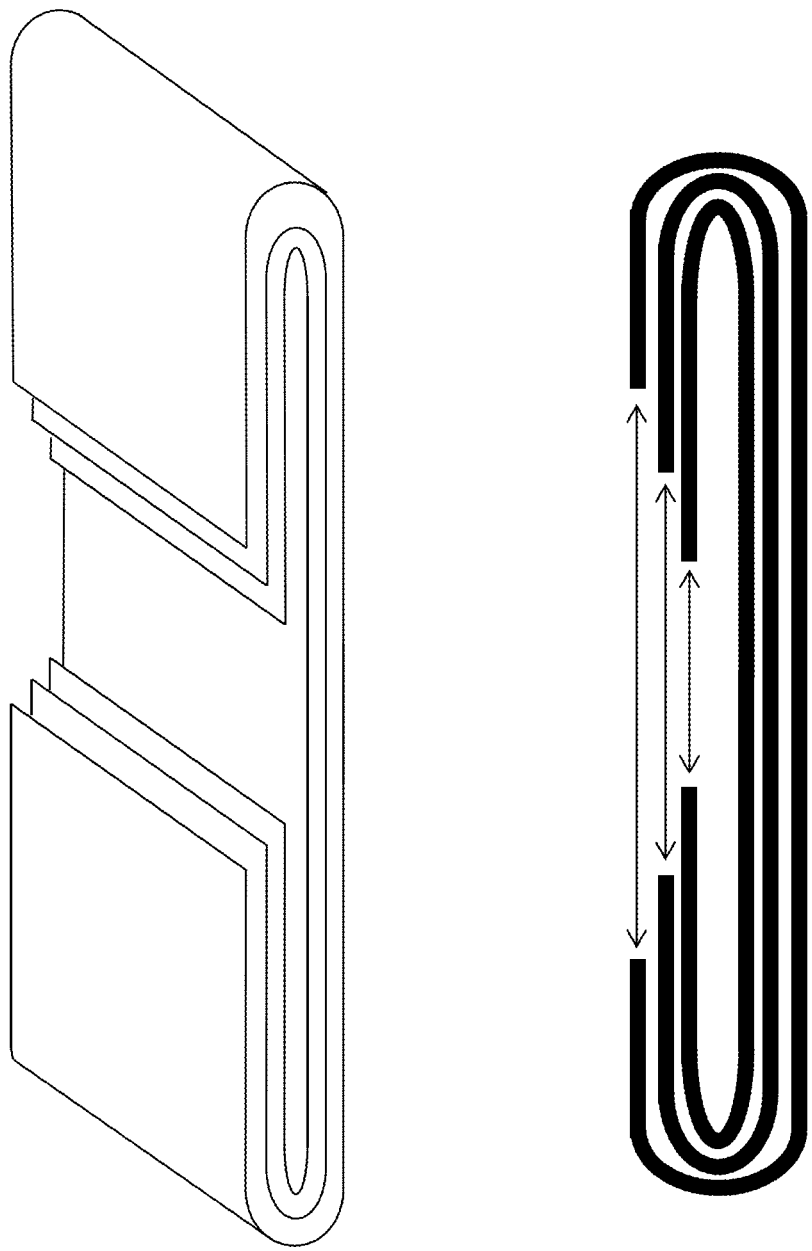

FIG. 12 schematically illustrates an alternate embodiment of a multiple-layer folded core according to the present invention.

Figure 13:
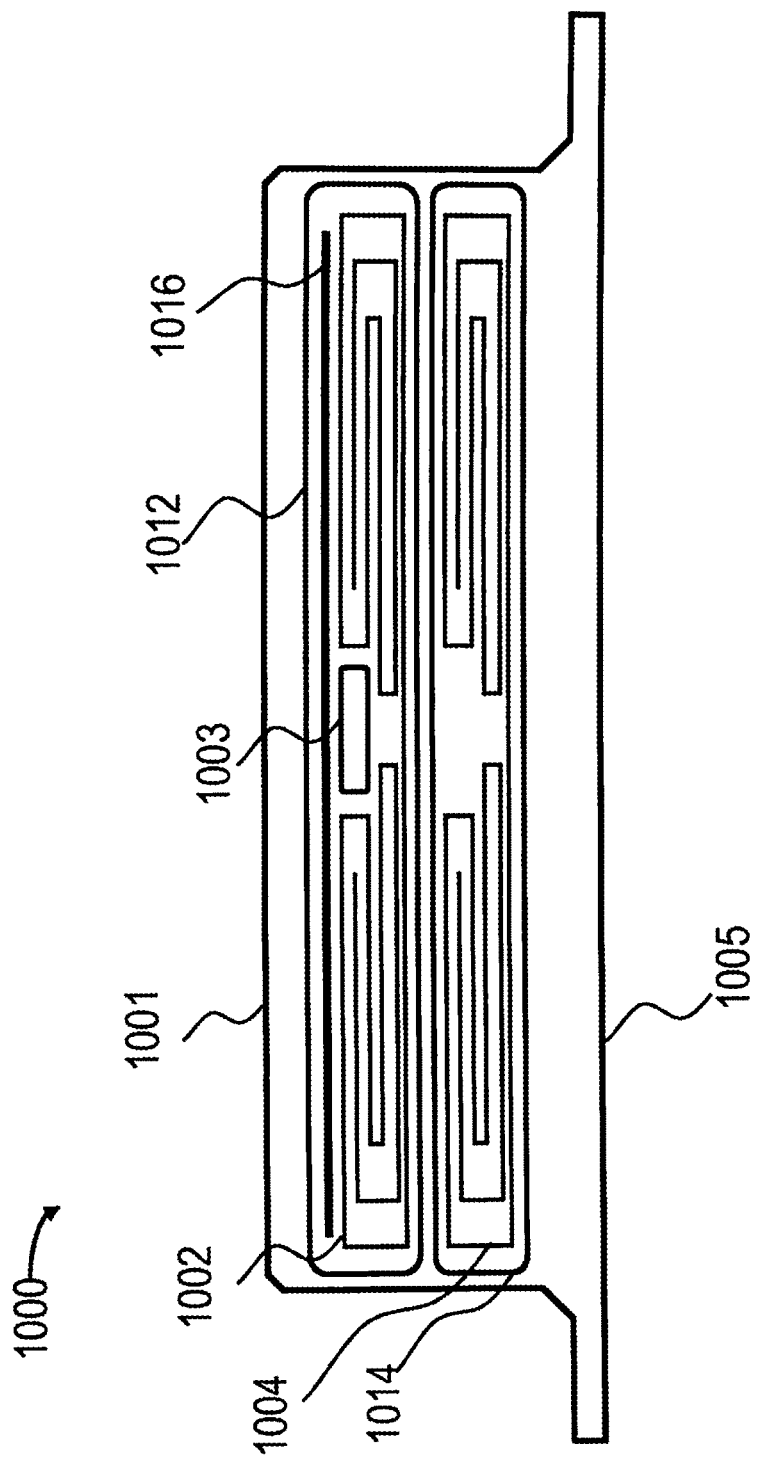

FIG. 13 is a schematic cross-sectional view of an absorbent article comprising one embodiment of a two-part core according to the present invention.

Figure 14A:
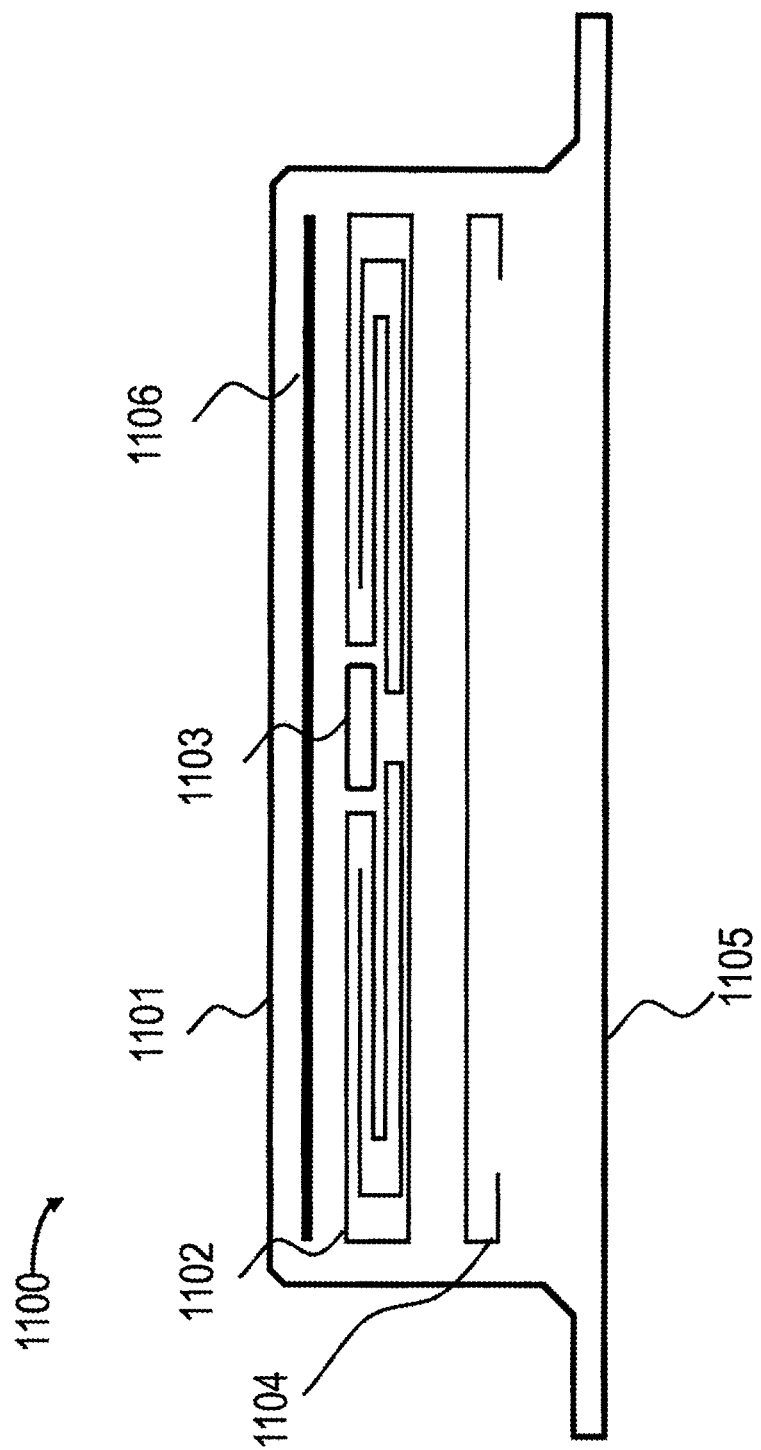
Figure 14B:
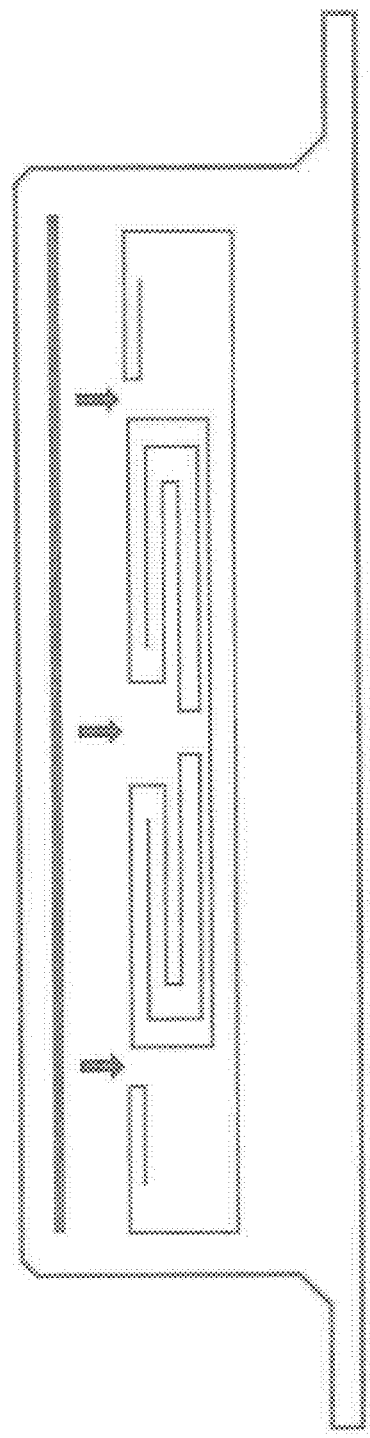

FIGS. 14A-14B are schematic cross-sectional views of absorbent articles comprising other embodiments of a Two-Part core according to the present invention.

Figure 15:
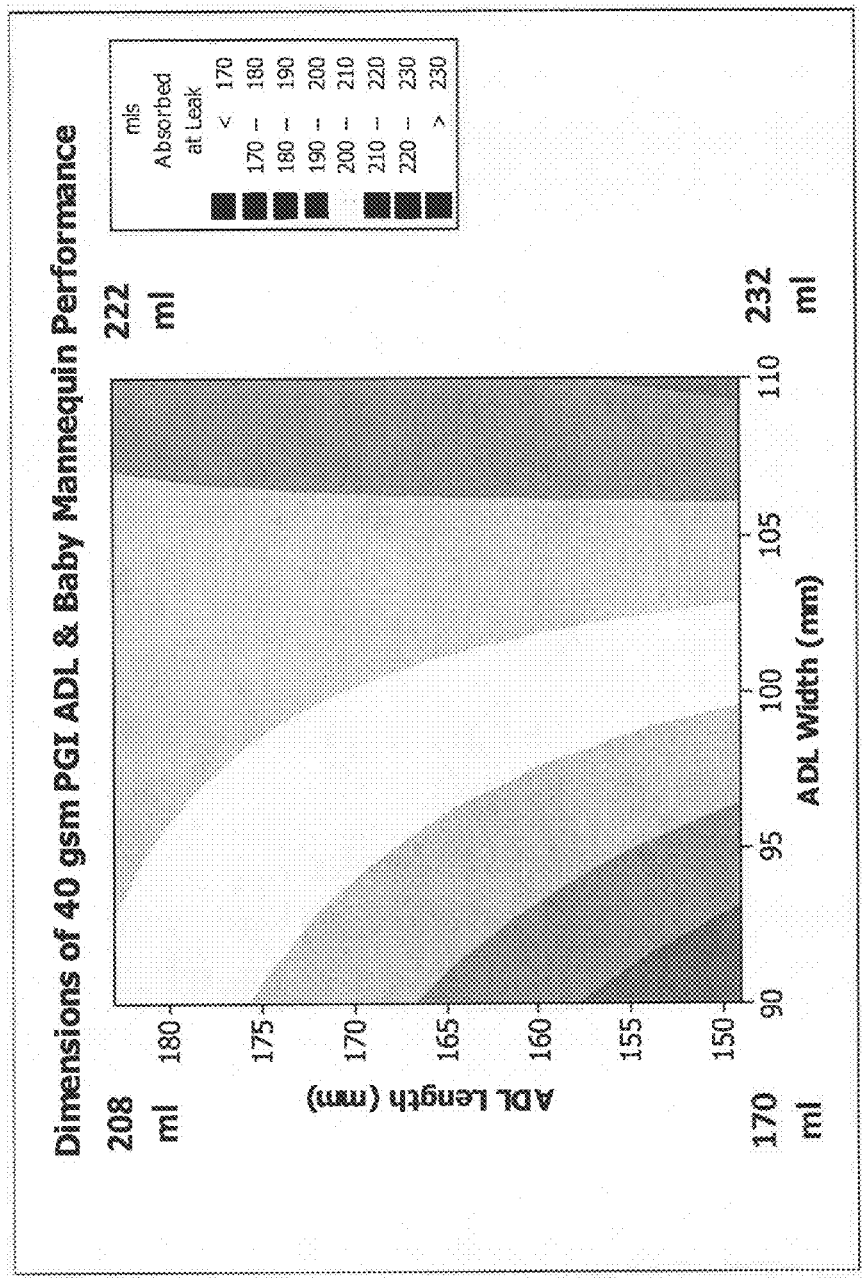

FIG. 15 is a chart optimizing the length and width of the ADL to maximize Mannequin ABL for diapers made with a core of the present invention.

Figure 16:
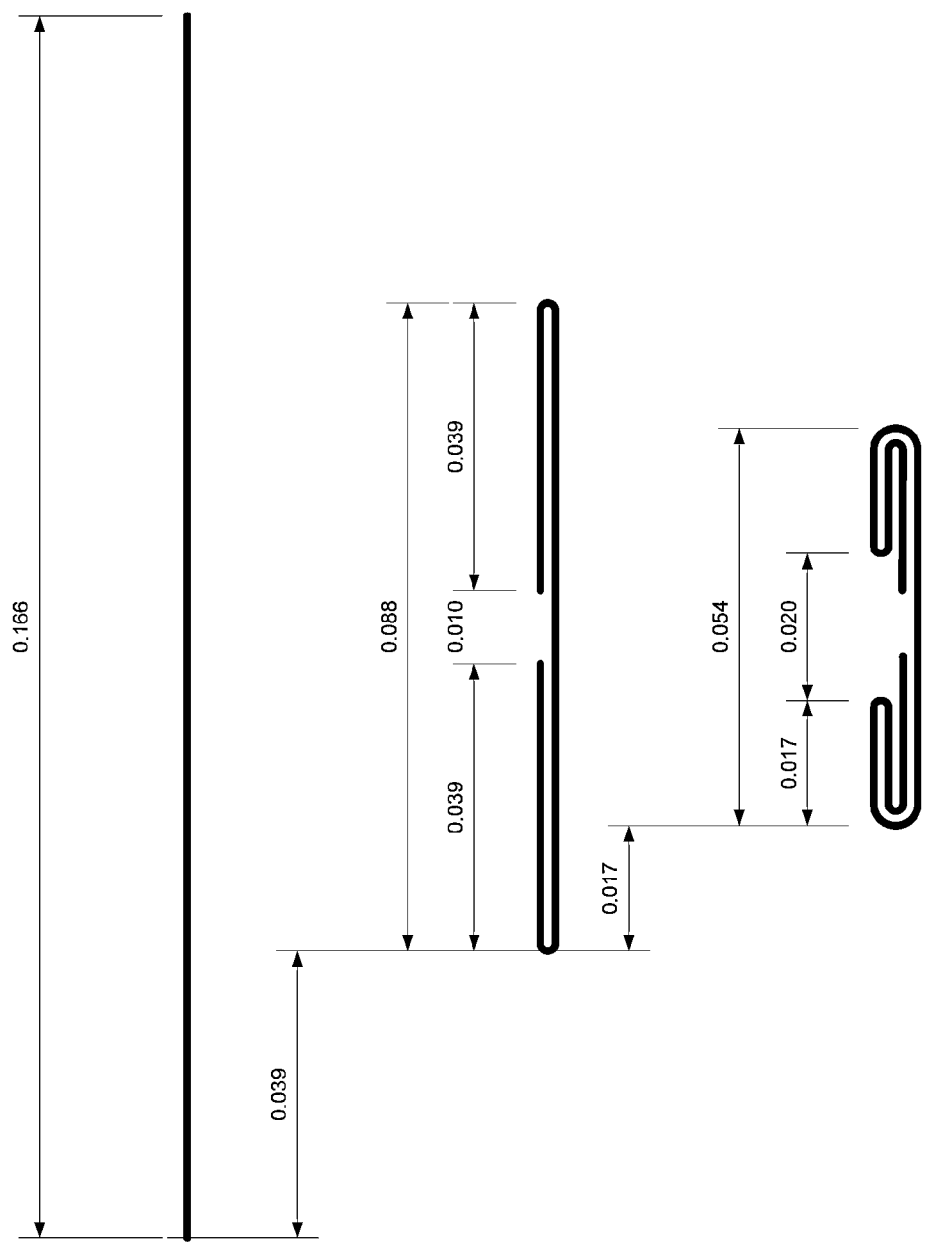

FIG. 16 shows dimensions of a 4-layer core after each of two folds.

Figure 17:
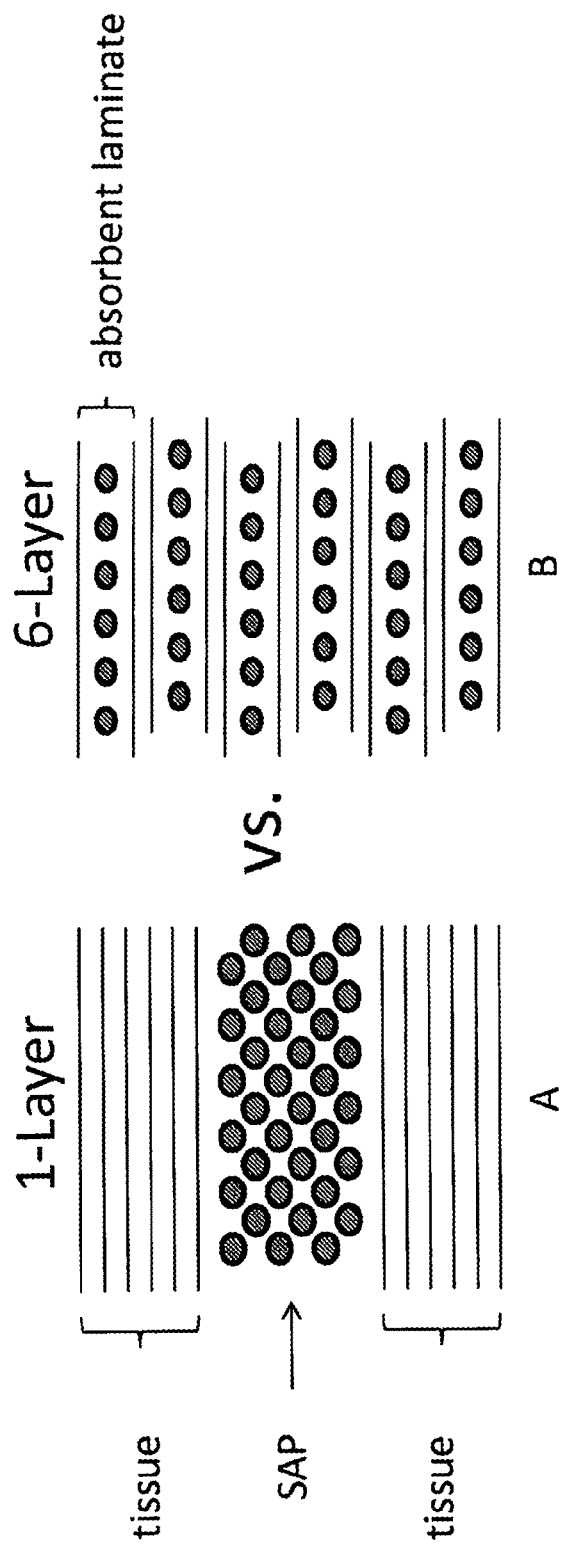

FIG. 17 illustrates schematically test core structures used for the 6-layer and 1-layer SAP AAP tests.

FIG. 18 presents SAP AAP, SAP RUL and SAP EFF results obtained using the core structures of FIG. 17.

Figure 19:
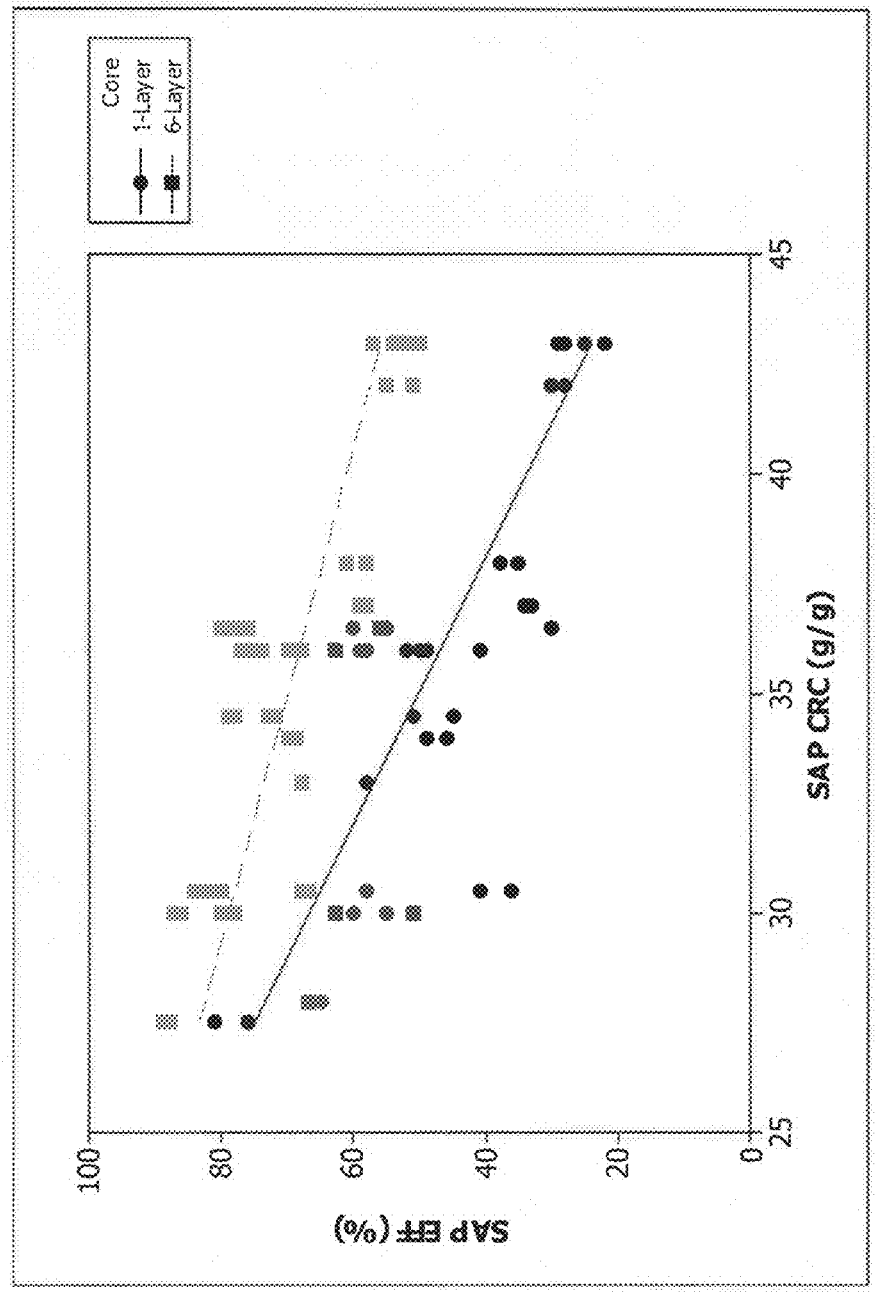

FIG. 19 shows SAP EFF from the 1-layer and 6-layer SAP AAP tests for various SAP's over a wide range of CRC.

Figure 20:
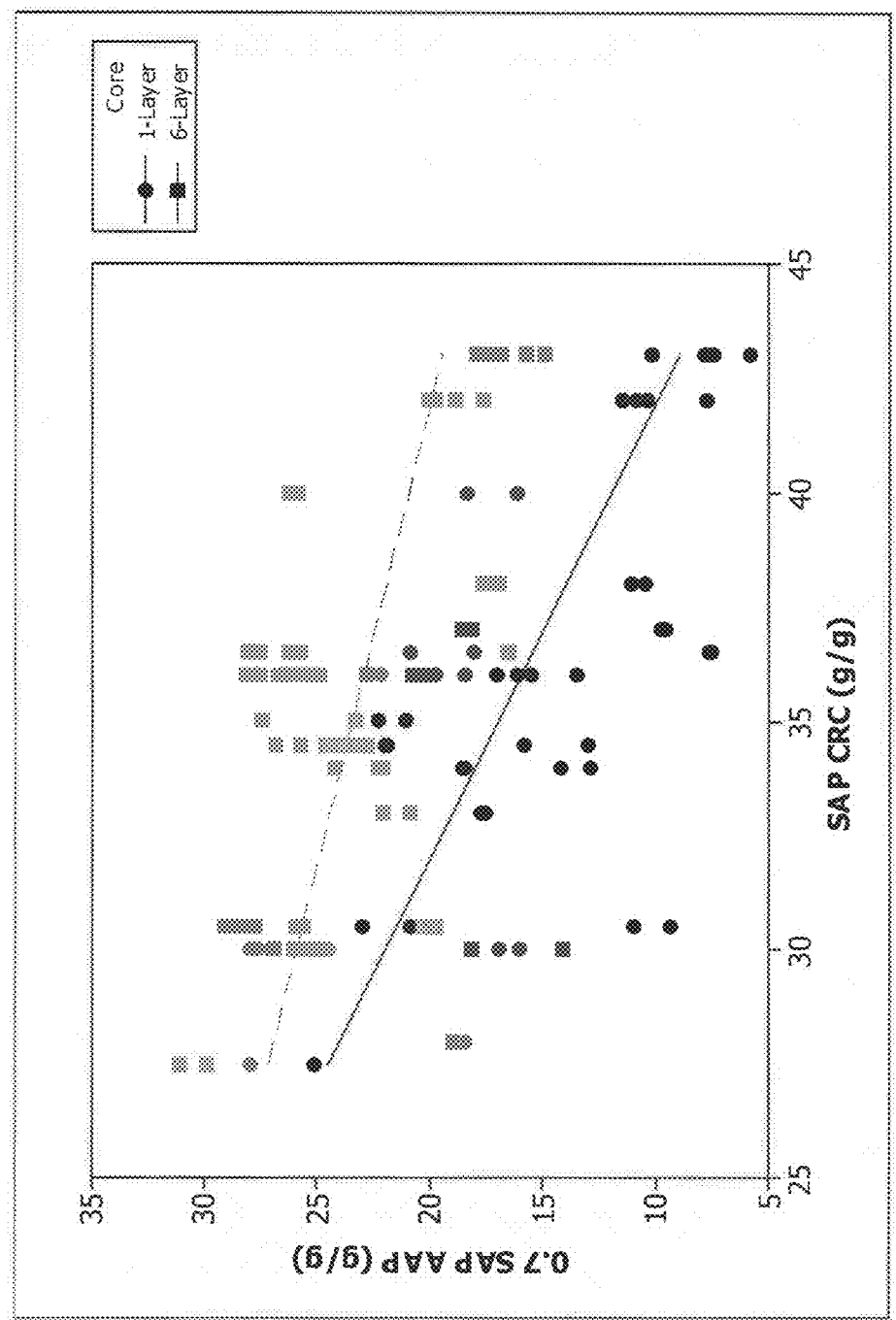

FIG. 20 shows 0.7 SAP AAP from the 6-layer SAP AAP test for various SAP's over a wide range of CRC.

Figure 21:
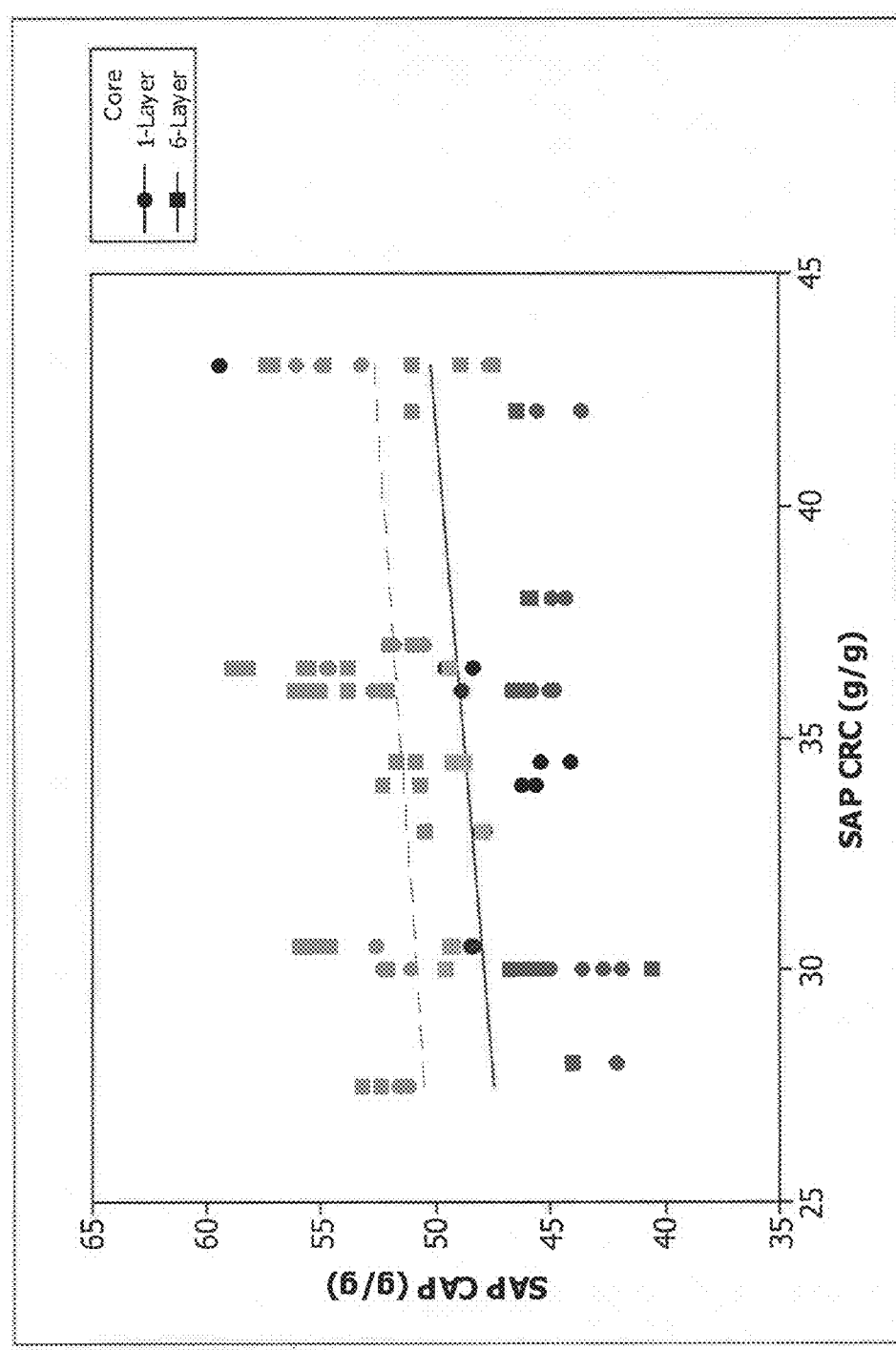

FIG. 21 shows SAP CAP results over a CRC range for a 6-layer core according to the present invention.

Figure 22:
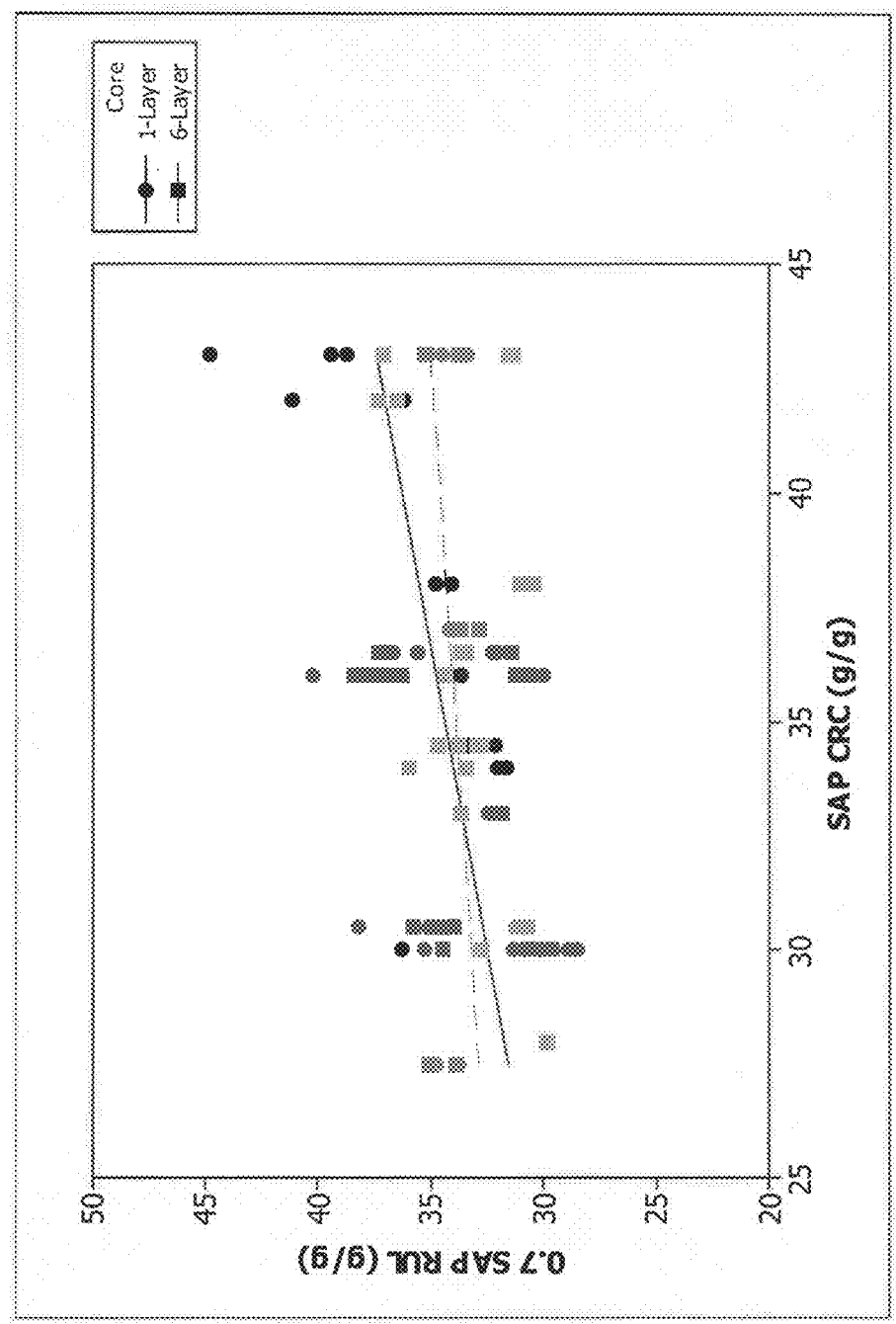

FIG. 22 shows SAP RUL results over a CRC range for a 6-layer core according to the present invention.

Figures 23, 24:
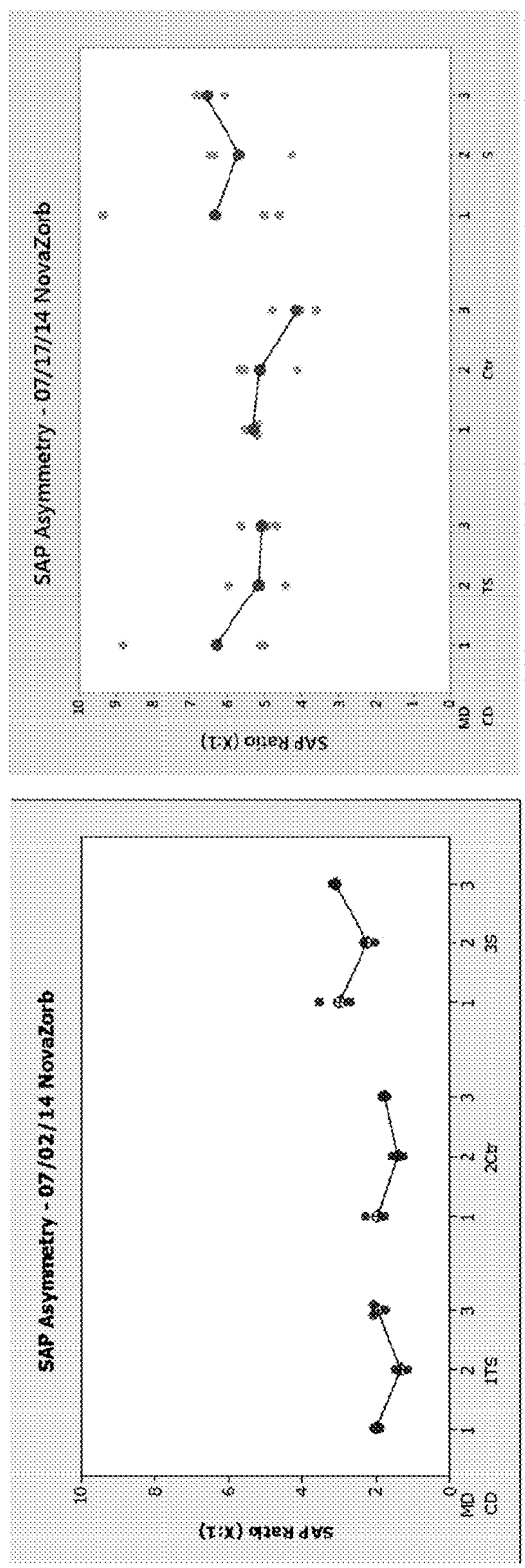

FIG. 23 shows low values of SAP asymmetry and analysis of variance for a laminate in both MD and CD directions.

FIG. 24 shows high values of SAP asymmetry and analysis of variance for a laminate in both MD and CD directions.

Figure 25A:
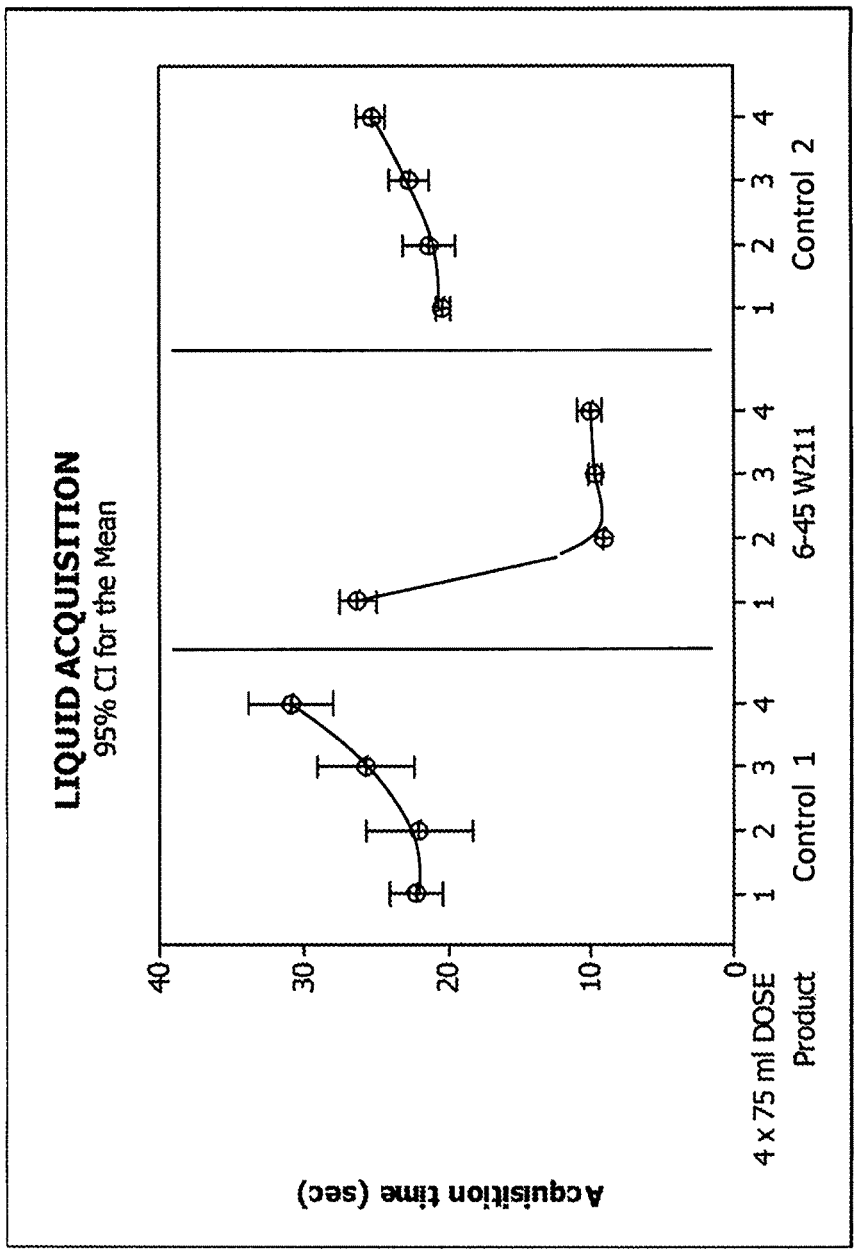
Figure 25B:
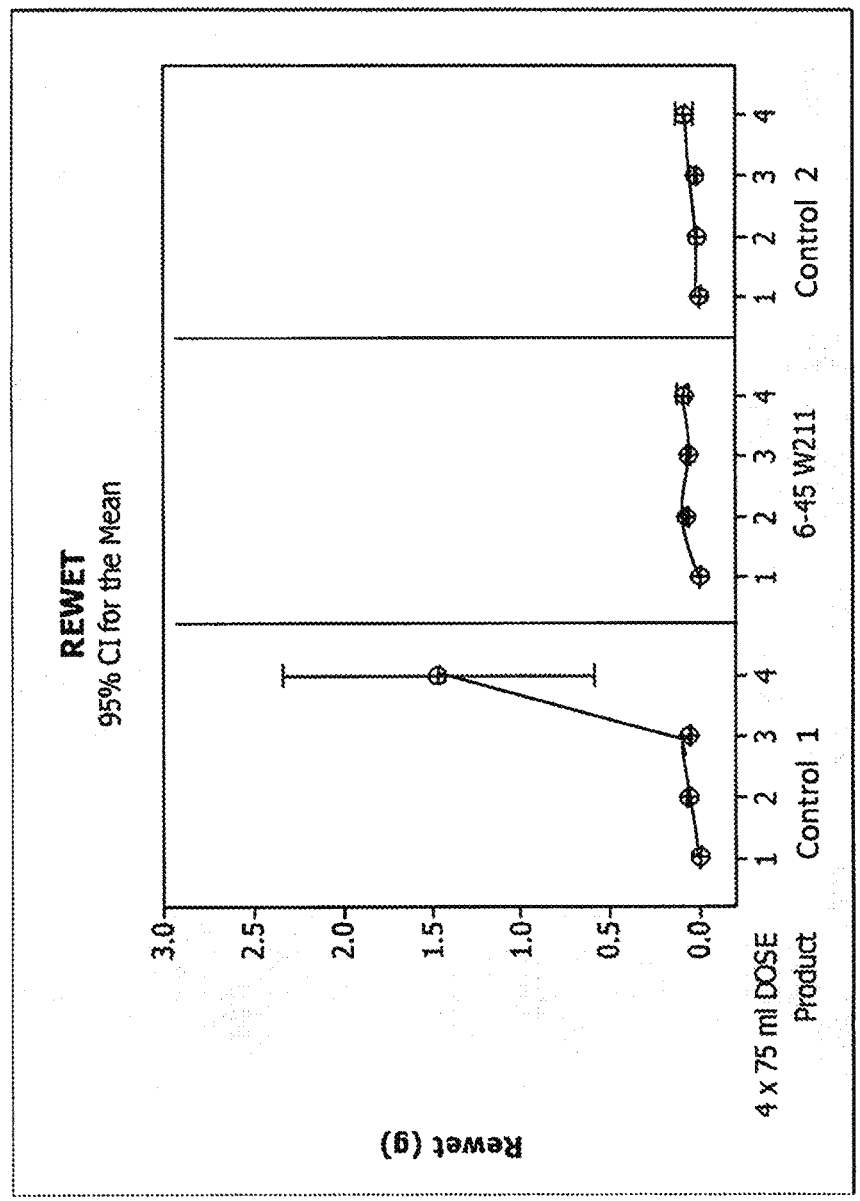

FIGS. 25A and 25B present liquid acquisition and rewet test results for a One-Part folded absorbent core compared to two commercially available diapers.

Figures 26A, 26B:
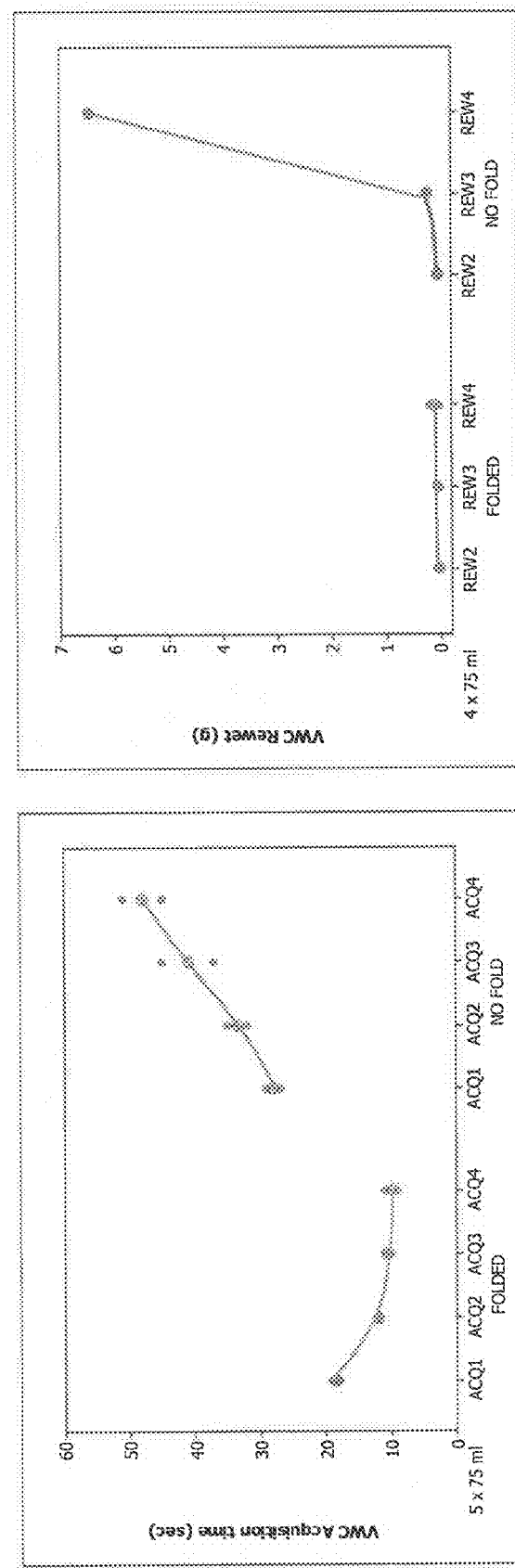

FIGS. 26A-26B present liquid acquisition and rewet test results for a One-Part, 6-layer folded absorbent core compared to an unfolded core.

Figure 27A:
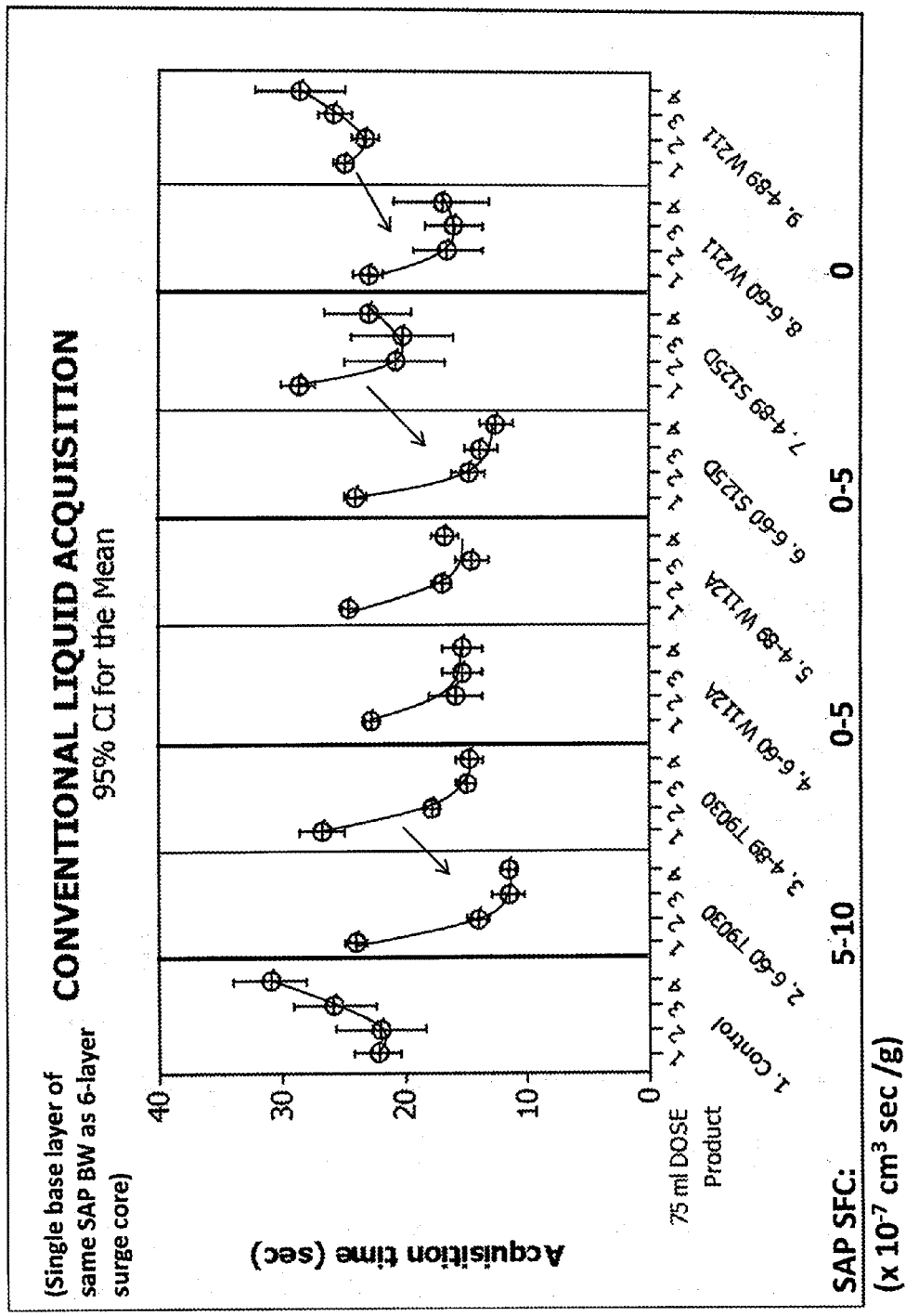
Figure 27B:
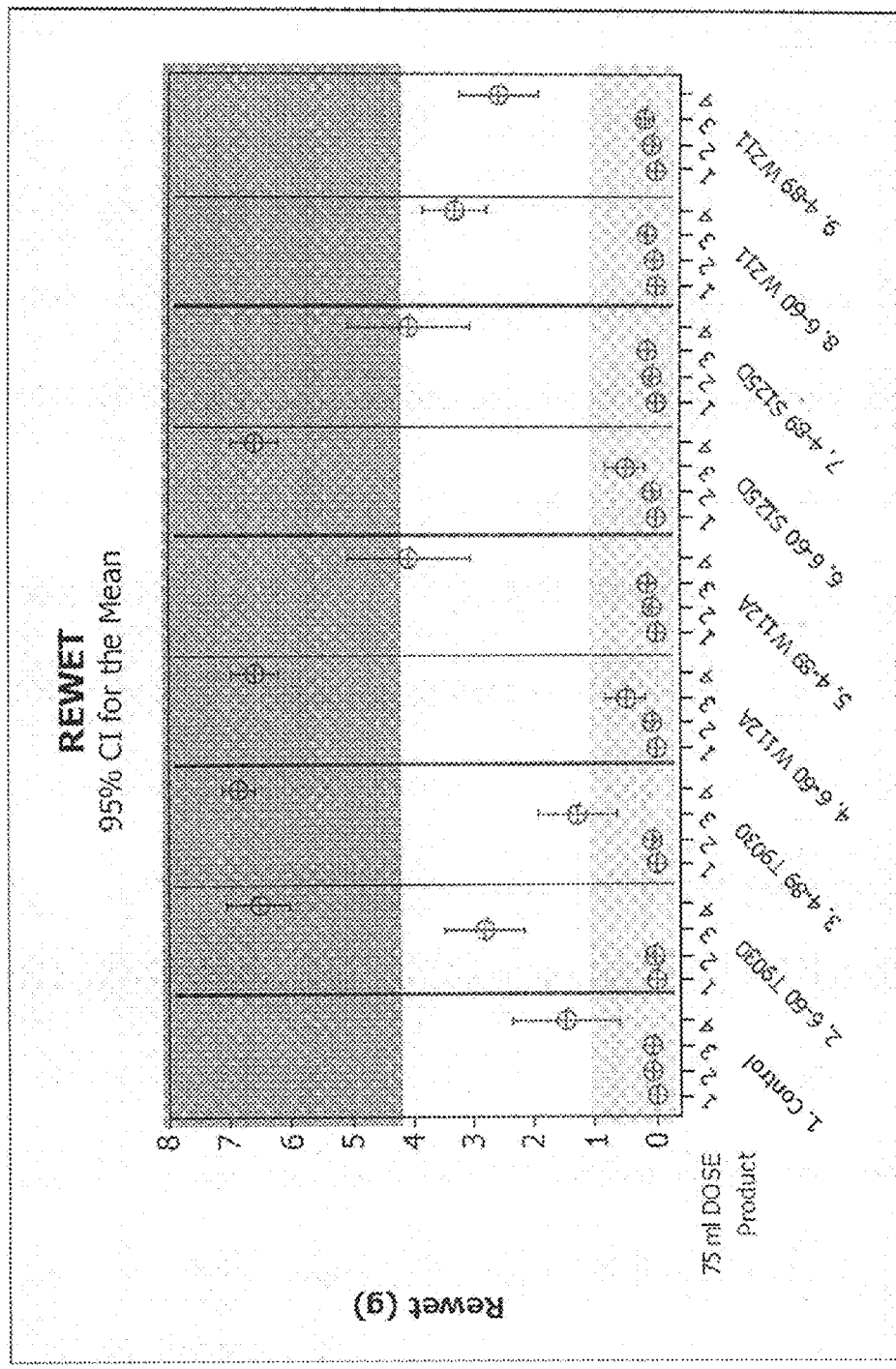

FIGS. 27A-27B present liquid acquisition test and rewet results for Two-Part, multi-layer absorbent cores according to various embodiments of the present invention compared to a conventional core.

Figure 28:
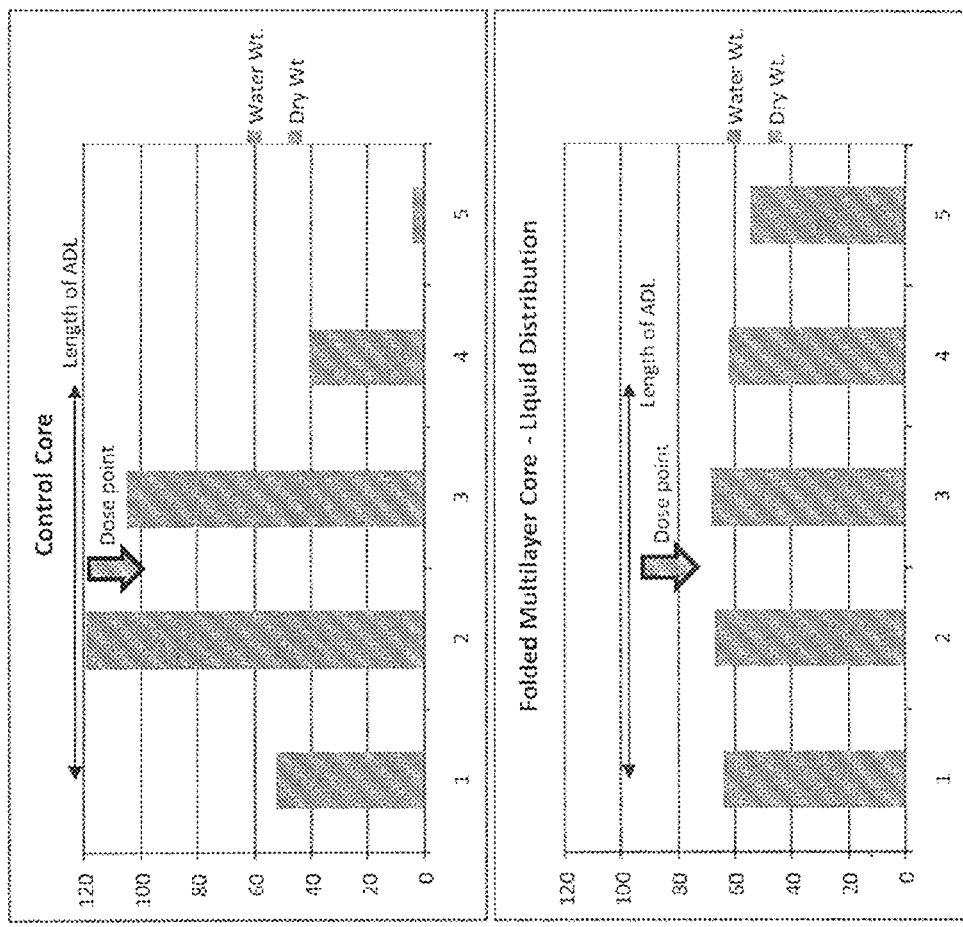

FIG. 28 presents liquid distribution along a One-Part, folded multilayer core according to the present invention compared to that of a conventional fluff/SAP core.

Figure 29A:
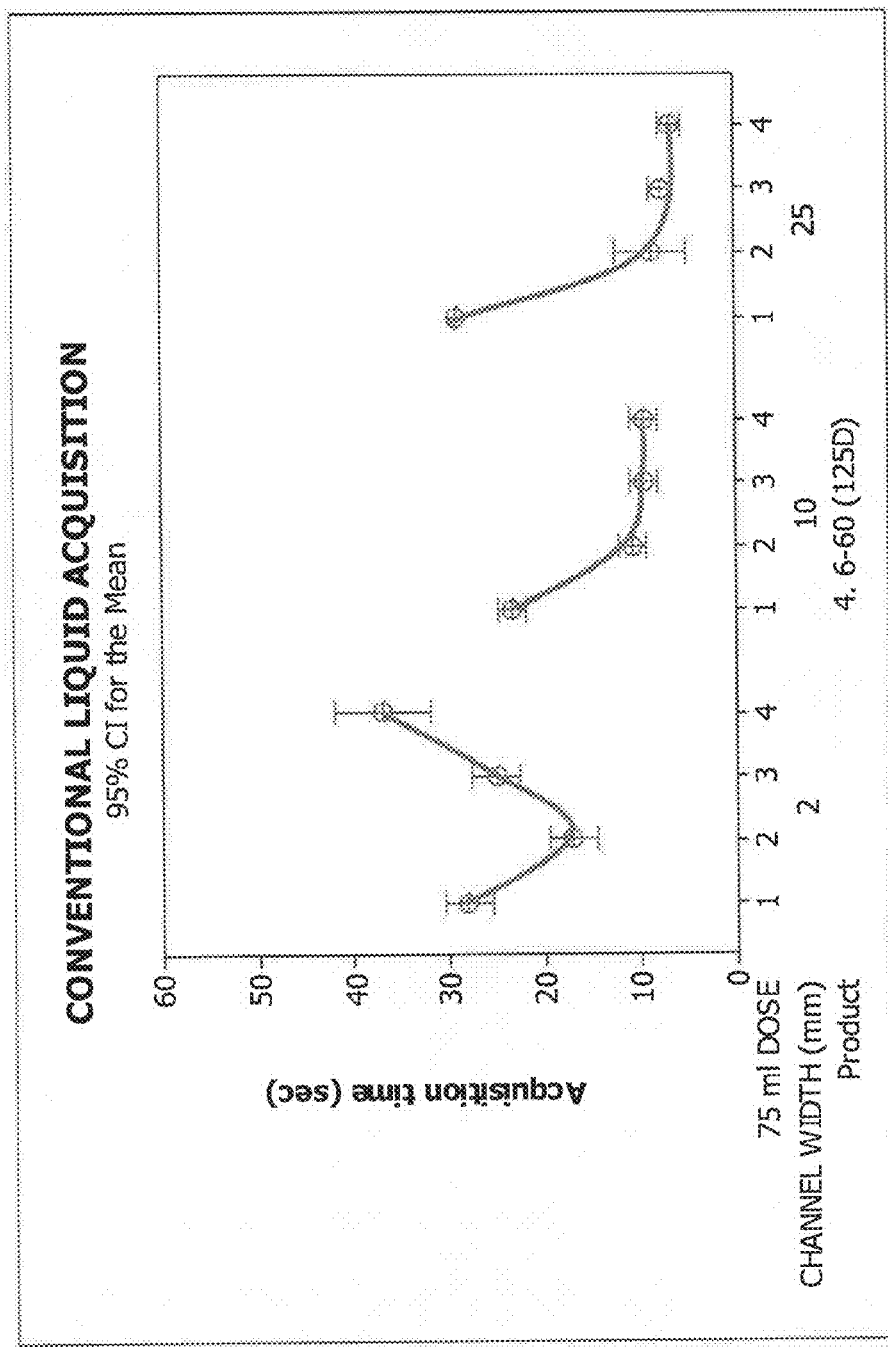
Figure 29B:
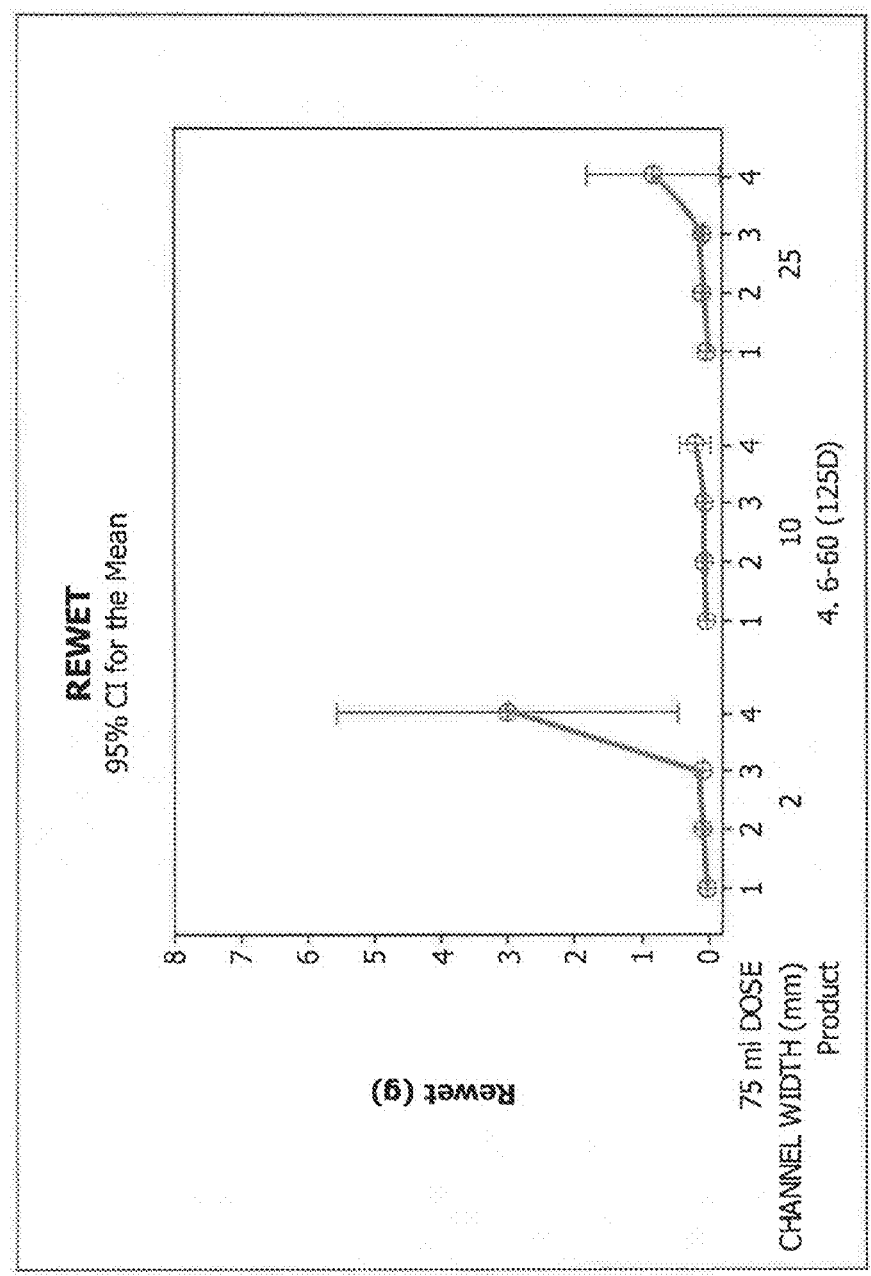

FIGS. 29A-29B demonstrate liquid acquisition times and rewet values for 6-layer folded cores with varying central channel widths.

Figure 30:
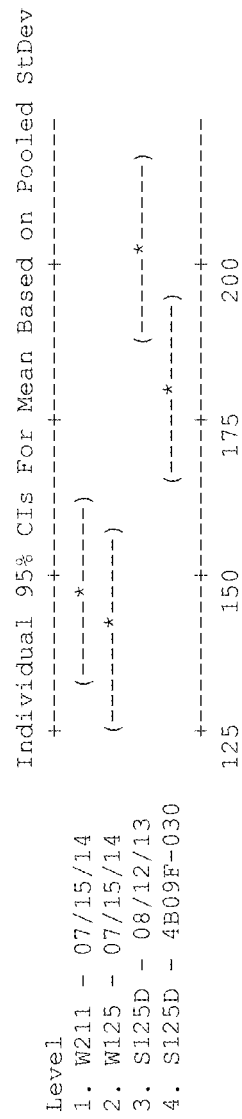

FIG. 30 shows a one-way Analysis of Variance for absorption times of SAP's used to make folded, multilayer cores for mannequin tests.

Figure 31A:
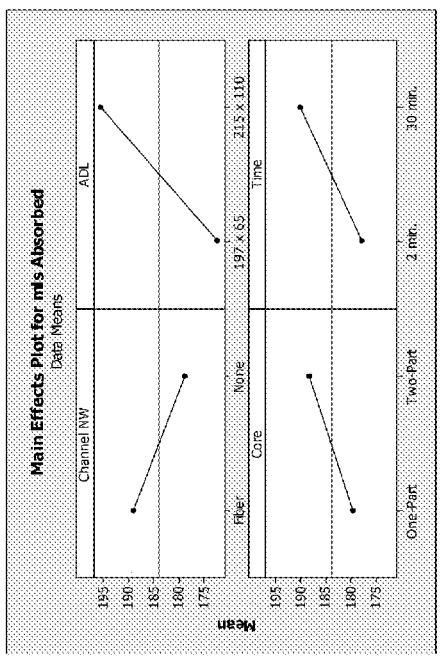
Figure 31B:
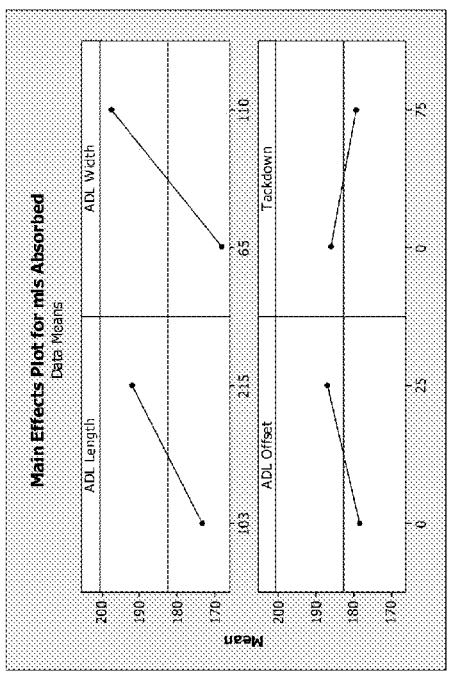
Figure 31C:
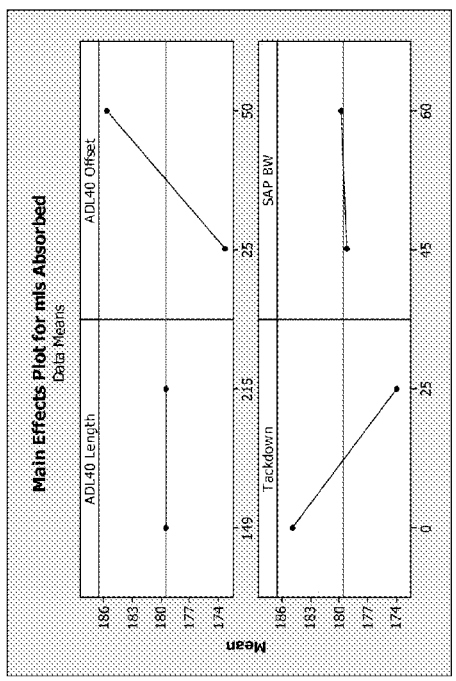

FIGS. 31A-31C relate the effects revealed by Designs of Experiment determining the effects of ADL length, ADL width, ADL offset and Tackdown Length on mannequin ABL for diapers made with a core of the present invention.

VI. DEFINITIONS AND CONSTRUCTIONS

Various features and advantageous details of the present invention are explained more fully in the following Detailed Description of Preferred Embodiments section. It should be understood, however, that the detailed description and the specific examples, while indicating embodiments of the invention, are given by way of illustration only, and not by way of limitation. Various substitutions, modifications, additions, and/or rearrangements within the spirit and/or scope of the underlying inventive concept will become apparent to those of ordinary skill in the art from this disclosure.

In the following description, numerous specific details are given to provide a thorough understanding of the present embodiments. One of ordinary skill in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

The terms "a" and "an" are defined as one or more unless this disclosure explicitly requires otherwise.

The terms "absorbent article" and "absorbent garment" refer to garments or articles that absorb and contain exudates and, more specifically, refer to garments or articles that are placed against or in proximity to the body of the wearer to absorb and contain the various exudates discharged from the body. These garments or articles, include diapers, training pants, feminine hygiene products, bibs, wound dressing, bed pads, and adult incontinence products. The term "disposable" when used with "absorbent article" or "absorbent garment" refers to garments and articles that are intended to be discarded after a single use.

"Absorbent core" means a structure positioned between a topsheet and backsheet of an absorbent article for absorbing and containing liquid received by the absorbent article and may comprise one or more substrates, absorbent polymer material, adhesives or other materials to bind absorbent materials in the core and, for purposes of the present invention, includes the disclosed absorbent laminate.

"Absorbent laminate" means the absorbent substrate described herein comprising top and bottom layers and an absorbent composition therebetween.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements possesses those one or more steps or elements, but is not limited to possessing only those one or more elements. Likewise, a step of a method or an element of a device that "comprises," "has," "includes" or "contains" one or more features possesses those one or more features, but is not limited to possessing only those one or more features. Furthermore, a device or structure that is configured in a certain way is configured in at least that way, but may also be configured in ways that are not listed. Metric units may be derived from the English units provided by applying a conversion and rounding to the nearest millimeter.

The term "coupled" is defined as connected, although not necessarily directly, and not necessarily mechanically.

Two items are "couplable" if they can be coupled to each other. Unless the context explicitly requires otherwise, items that are couplable are also decouplable, and vice-versa. One non-limiting way in which a first structure is couplable to a second structure is for the first structure to be configured to be coupled (or configured to be couplable) to the second structure.

Terms such as "first" and "second" are used only to differentiate structures or features, and not to limit the different structures or features to a particular order.

The term "substantially" and its variations (e.g., "approximately" and "about") are defined as being largely, but not necessarily wholly, what is specified (and include wholly what is specified, e.g., substantially 90 degrees includes 90 degrees and substantially parallel includes parallel) as understood by one of ordinary skill in the art. In any embodiment of the present disclosure, the terms "substantially," "approximately," and "about" may be substituted with "within [a percentage] of" what is specified, where the percentage includes 0.1, 1, 5, 10, and 15 percent.

"Thickness" and "caliper" are used herein interchangeably.

The feature or features of one embodiment may be applied to other embodiments, even though not described or illustrated, unless expressly prohibited by this disclosure or the nature of the embodiments.

Other features and associated advantages will become apparent with reference to the following detailed description of specific embodiments in connection with the accompanying drawings.

VII. DETAILED DESCRIPTION OF PREFERRED EMBODIMENTS

The present invention is directed to a multi-layer folded absorbent core that provides numerous advantages, including rapid liquid acquisition, improved core utilization, high superabsorbent material efficiency, the use of higher capacity superabsorbent materials, excellent liquid containment, the possible elimination of conventional materials, such as a core wrap, and improved core stability and integrity in use.

A. The Absorbent Laminate

Figure 1:
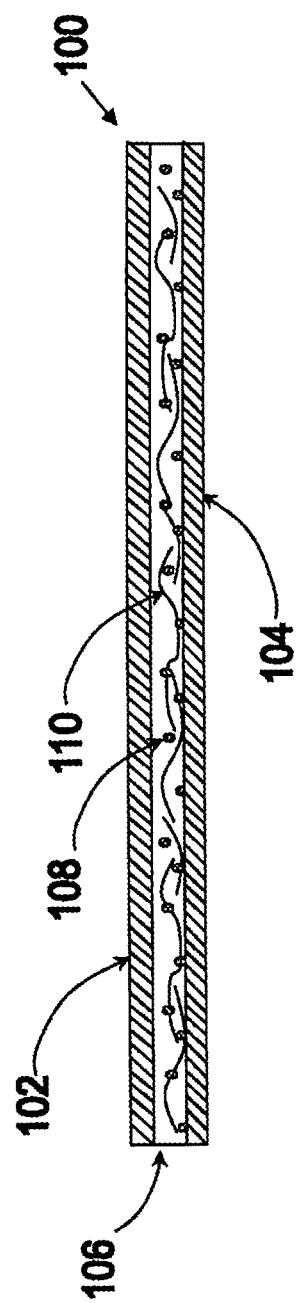
FIG. 1 is a schematic view of an absorbent laminate.

FIG. 1 is a horizontal cross-sectional illustration of an embodiment of an absorbent laminate 100 of a type for use in the multi-layer folded absorbent core according to the present invention. The absorbent laminate comprises an upper laminate layer 102, a lower laminate layer 104, with an intermediate layer 106 between the upper and lower laminate layers.

Upper laminate layer 102 and/or lower laminate layer 104 may be constructed from a variety of materials, including synthetic nonwoven, such as spunbond or carded webs of polypropylene, polyethylene, nylon, polyester and blends of these materials, and tissue. In preferred embodiments, either or both layers comprise tissue. The tissue, for example, can be a porous tissue, a creped tissue or a standard tissue. A preferred material is 3995 tissue from Dunn Paper from East Hartford, Conn. The tissue could also be a high creped variety such as 1113, also available from Dunn Paper.

It is possible to print, or otherwise attach, SAP particles to a single layer of tissue or nonwoven and it is envisioned that these types of materials could also be used to make folded, multi-layer absorbent cores that will be described in later sections. It is well known that there are non-adhesive bonding methods for laminating tissue and nonwovens. Mechanical bonds or stitching can be used to make bond multi-layer tissue laminates. Synthetic fiber nonwovens can be bonded with thermal or ultrasonic bonding techniques well known in the art.

In some embodiments, one or both of upper laminate layer 102 or lower laminate layer 104 can comprise a wet strength additive, such as Kymene™ from Solenis International, L.P. of Wilmington, Del. Such wet strength additive can be applied, preferably in lanes, to the upper and/or lower laminate layers in the cross (or width) direction to strengthen the edges and/or control leakage at the side of a folded core. In other embodiments, upper laminate layer 102, lower laminate layer 104, or both may comprise a skin wellness ingredient and/or an odor-control ingredient. In certain embodiments, the upper layer is highly porous and liquid permeable and the lower level is substantially liquid impermeable.

Turning now to the intermediate layer 106, as mentioned, the intermediate layer includes an absorbent composite comprising particulate superabsorbent material 108 and an adhesive composition 110. "Superabsorbent material," or "Superabsorbent polymer," or "SAP" refers to water-swellable, water-insoluble material capable of absorbing many times its weight in liquid. The superabsorbent material can comprise a variety of materials, including organic compounds, such as cross-linked polymers. "Cross-linked" is a commonly understood term and refers to any approach for effectively rendering normally water-soluble materials substantially water insoluble, but swellable. Such polymers include, for example, carboxymethylcellulose, alkali metal salts of polyacrylic acids, polyacrylamides, polyvinyl ethers, hydroxypropyl cellulose, polyvinyl morpholinone, polymers and copolymers of vinyl sulfonic acid, polyacrylates, polyacrylamides, polyvinyl pyridine and the like. Other suitable polymers include hydrolyzed acrylonitrile grafted starch, acrylic acid grafted starch, and isobutylene maleic anhydride copolymers, and mixtures thereof. Organic high-absorbency materials can include natural materials, such as agar, pectin, guar gum and peat moss. In addition to organic materials, superabsorbent materials may also include inorganic materials, such as absorbent clays and silica gels. Suitable examples of SAP include T9030 from BASF Corporation, Charlotte, N.C.; and W211, W112A, W125 and S125D from Nippon Shokubai Co. Ltd, N.A.I.I., Houston, Tex., and Aqua Keep SA60N II and SA55SX II from Sumitomo Seika Chemicals Co., Ltd., Osaka, Japan.

Over the last 25 years, diaper cores have become thinner and the concentration of SAP in the core has increased from about 15% in 1990 to about 50% in 2015. The trend continues today with the commercial introduction of new types of absorbent cores that contain no fluff pulp. Fluffless cores contain a high basis weight layer of SAP, and liquid-spreading properties of this partially-hydrated, thick layer of SAP mediate the spreading and distribution of liquid in the core. Under pressure, the spreading of liquid through a swollen gel mass can stop. This condition is referred to as gel blocking To help promote the spreading and distribution of liquid in this type of core the permeability of SAP's has been increased. SAP permeability is achieved by an increase in crosslinking density that increases the swollen gel strength of the polymer. Polymers of high gel strength are more permeable because individual, irregularly-shaped particles of SAP can retain their shape as they swell and prize adjacent particles apart when swelling under pressure. These swelling particles prize apart, draw air into the gel mass, and create a capillary network for liquid spreading. SAP's that provide good liquid spreading in a core have higher values of 0.7 psi AAP (Absorption Against Pressure) g/g and higher ratios of 0.7 AAP/0.7 RUL (ratio of AAP to Retention Under Load) (i.e., SAP Efficiency). The compromise involved in the use of a high gel-strength, permeable SAP is that it has a lower specific liquid-holding capacity, as evidenced by a reduced value of CRC (Centrifuge Retention Capacity), which is expressed in units of g. of liquid absorbed per g. of SAP. The net result of these conditions is that more permeable SAP must be used to achieve the total liquid-holding capacities required for a particular application.

Fluffless cores of the current invention provide a multi-layer laminate structure that separates SAP particles between wicking layers of tissue to greatly reduce gel blocking of the SAP and to promote liquid spreading and distribution between the layers of the laminate. A layer of SAP of about one-particle thickness will be achieved for about 50 gsm of SAP. A SAP layer that has a thickness of two SAP particles thick will be about 100 gsm. So, even for laminates containing 100 gsm of SAP, individual particles of SAP will be in direct contact with a layer of tissue that provides an effective capillary network for liquid spreading. The capillary network provided by the tissue is, of course, independent of the properties of the SAP and it remains open as the core absorbs liquid and the polymer swells. The multi-layer structure of the absorbent core actually improves SAP performance. It has been unexpectedly discovered that the structure of a multi-layer core of the current invention imparts exceptional permeability to the core so that SAP's with higher capacity (and lower permeability) can be used to advantage to maximize the 0.7 AAP of SAP, and SAP efficiency, in a folded, multi-layer core structure.

Identification of optimal properties of a SAP for efficient use in a folded, multi-layer core is an important part of the current invention. It has been discovered in that regard that SAP's with a mid-range CRC, in the range of about 33-38 g/g, can provide high values of 0.7 AAP, which is a key measure of cost-effective performance in an absorbent core. 0.7 AAP of preferred SAP's in a multi-layer core have been measured to values of about 23-29 g/g, while the 0.7 SAP AAP for an equal mass of SAP in a 1-layer core has AAP values less than about 20 g/g. This is achieved through the use of multi-layer core designs to provide increases in SAP efficiency under load.

The superabsorbent material typically is in particle form and can be of any desired configuration, such as granulated powders, fibers, agglomerated spheres and other shapes known to those skilled in the art. The particle size of the superabsorbent material may vary, but typically ranges from about 20 microns to about 1000 microns. Superabsorbent polymer particles, however, can impart roughness. According to the present invention, a number of ways have been identified to reduce this roughness. As a first approach, the SAP particle size may be reduced. It has been discovered that SAP's for use in the present invention should have a fine particle size distribution. This fine particle size approach contrasts with state-of-the-art fluffless core design, which generally use SAP's with coarse particles to help improve liquid permeability of high gel-strength SAP's. Particularly, superabsorbent polymers having a mean particle size in the range of about 250 µm to about 350 µm and with a particle size distribution where only 3% of the mass of the superabsorbent polymer cannot pass through a 500 µm screen will provide a meaningful reduction in surface roughness of the laminate materials. An example of a superabsorbent polymer with this type of particle size distribution would be SA60N Type II provided by Sumitomo. Even more preferred, surface roughness of the laminate can be mostly eliminated for a superabsorbent polymer that contains no particles greater than 500 µm.

It also has been discovered that, according to the present invention, this reduction in roughness is largely independent of the basis weight of the SAP used to make the laminates. By way of example, laminates were made according to the present invention at three SAP basis weights using three superabsorbent polymers with two layers of a 17 gsm tissue substrate of the grade 3995 commercially available from Dunn Paper from East Hartford, Conn. SAP basis weights of the laminates were 47, 60, and 97 gsm. The three superabsorbent polymers had different amounts of polymer residing in particles greater than 500 µm. SA60N Type II (Sumitomo) had 3% of the mass of the polymer residing in particles greater than 500 µm, S125D (Nippon Shokubai) had 18%, and W211 (Nippon Shokubai) had 48%. W211 provided laminates with the greatest amount of surface roughness, S125D provided less roughness, and SA60N Type II provided the best laminate with even less roughness. The spherical shape of particles of the SA60N Type II SAP may have contributed to the reduction in surface roughness. Surface roughness was independent of the basis weight of SAP used to make these laminates. It was noteworthy that surface roughness of the laminates was mostly eliminated when laminates were made with all of these polymers after the polymers had been screened to remove all particles greater than 500 µm.

Alternatively, any commercially available SAP can be used as a starting SAP material and then can be filtered or screened to obtain applicable and useful SAP to minimize surface roughness where the polymer contains less than about 10% of the mass of the polymer residing in particles greater than 500 µm, more preferably less than 3%, and most preferably no particles greater than 500 µm.

In addition to SAP selection or modification, surface roughness may be addressed by mechanical or structural means, such as by adding additional tissue or nonwoven or similar material between the laminate and the wearer. For example, laminates containing three and four layers of tissue exhibit less roughness with little or no meaningful increase in core stiffness. Laminates comprised of more than two layers of tissue also provide better SAP performance, because the total amount of SAP required can be placed in more than one layer. SAP efficiency improves with decreasing SAP basis weight. Placing SAP in more than one layer also provides opportunities to use more than one SAP, and to use SAP and acquisition materials in separate layers. The basis weight of the existing tissue substrates can be increased in order to reduce the roughness; however, this approach may not be preferred given the likely resulting increase in core stiffness. As yet another alternative, Acquisition-Distribution Layers (ADL) of Through-Air-Bonded (TAB) nonwoven in the range of about 30 gsm to about 120 gsm, which is a core structure well known to those skilled in the art, may be disposed on the surface of the core adjacent the wearer to mask surface roughness, as well as improve acquisition and rewet performance. Similarly, cellulosic acquisition fiber layers similarly disposed in the range of about 100 gsm to about 350 gsm can mask the roughness. Additionally, TAB nonwovens and cellulosic acquisition fibers can be used together to effectively reduce surface roughness.

Additionally, the SAP may be uniformly or non-uniformly distributed within the intermediate layer. In the illustrated embodiment of FIG. 1, intermediate layer 106 comprises SAP that is uniformly applied at a relatively low basis weight, thereby forming substantially a single layer of SAP particles. However, a non-uniform SAP distribution in the absorbent laminate is preferred in many embodiments of the invention in order to enhance z-direction liquid permeability through the laminate. SAP distribution may be reflected by the measured Coefficient of Variation (COV) of the distribution. COV is defined as the standard deviation of basis weight of absorbent laminate samples divided by the mean basis weight and can be measured according to the following test. A circular die of 30 mm diameter is used to cut a total of 27 samples from an absorbent laminate according to the present invention. For a 500 mm wide×385 mm length absorbent laminate used to make a folded, multi-layer core, as will be described herein in more detail in subsequent sections, a 3×3 array of samples is cut, in triplicate from three separate pieces of laminate. Each sample is weighed to determine its basis weight, and the coefficient of variation (COV) of basis weight is calculated for the laminate. The COV of basis weight is defined as (Std Dev of BW)/(Mean BW)×100%. In preferred embodiments of the present invention, the COV of basis weight for absorbent laminates should be greater than about 5%.

As indicated, the intermediate layer of the absorbent composite 106 preferably also includes an adhesive composition. The adhesive composition should be of a type that is suitable for use in the production of disposable hygiene articles. In certain preferred embodiments, the adhesive composition is a thermoplastic hot-melt adhesive composition. A thermoplastic hot-melt adhesive composition generally comprises one or more polymers that provide cohesive strength, a resin or similar material that provides adhesive strength, possibly waxes, plasticizers or other materials that modify viscosity, and other additives, such as antioxidants and stabilizers. According to more preferred embodiments of the present invention, the adhesive composition is a pressure-sensitive thermoplastic adhesive composition, more preferably, a synthetic rubber-based pressure sensitive adhesive composition having a glass transition temperature greater than 25° C. In specific embodiments, the adhesive composition may be a Styrene-Butadiene-Styrene (SBS) or Styrene-Isoprene-Styrene (SIS) block copolymer hotmelt adhesive composition. In this regard, these preferred adhesive compositions are described in Provisional Patent Application No. 61/946,304, entitled "Novel Absorbent Laminate for Disposable Absorbent Articles," filed Feb. 28, 2014, which is herein incorporated by reference for all purposes and in a manner consistent with this application and invention. The amount of the adhesive composition applied should be kept generally at the minimum amount necessary to provide a laminate with acceptable integrity to be unwound at high speed in a converting process used to make absorbent articles containing the laminate. In this regard, the preferred adhesive compositions provide sufficient cohesive strength to the laminate to allow for the use of a reduced amount of the adhesive composition.

The superabsorbent material and adhesive composition may be present in the intermediate layer in a variety of amounts, with preferred embodiments including the superabsorbent material as the majority component in the layer. In more preferred embodiments, the superabsorbent material comprises at least about 90% of the total weight of the intermediate layer and, more preferably, at least about 94%, even more preferably, at least 95%, at least about 97%, at least about 98% and even at least about 99%, of the total weight of the SAP.

In an alternative embodiment the absorbent laminate may utilize discrete acquisition cell (DAC) technology. This technology, and the inventions related to it, are described in U.S. patent application Ser. No. 14/212,754, entitled "Absorbent Structure with Discrete Acquisition Cells," filed on 14 Mar. 2014, and Ser. No. 14/212,969, entitled "Absorbent Structure with Dryness Layer," filed 14 Mar. 2014, which applications are herein incorporated by reference for all purposes and in a manner consistent with this application and invention. DACs address the paradox of requiring high free volume for instantaneous liquid absorption in a low-volume thin structure. DACs provide an instantaneous increase in free volume in thin cores to rapidly absorb and contain free liquid before any appreciable swelling of SAP can occur and partition liquid into SAP over time so as to regenerate free volume in the DACs to absorb subsequent doses of liquid. Discrete Acquisition Cells can be comprised of compressed cellulosic sponge, creped cellulosic paper, soy bean hulls, and other filler materials that provide free volume for rapid absorption of liquid in thin laminates. In other embodiments, filler such as wood pulp or cellulosic fluff, may be mixed with the adhesive and SAP.

In embodiments where the absorbent layer contains Discrete Acquisition Cells, the superabsorbent material comprises at least about 40% of the total weight of the intermediate layer. Furthermore, in embodiments where the absorbent layer contains continuous filament or staple fiber tow, or continuous filament or staple fiber yarn, the superabsorbent material comprises at least about 40% of the total weight of the intermediate layer. In this regard, the basis weight of the SAP in the intermediate layer may range from about 10 grams per square meter (gsm) to about 400 gsm, preferably from about 40 gsm to about 150 gsm.

As shown in FIG. 1, in one embodiment, left edge and right edge of laminate 100 are open and are substantially uncovered by upper laminate layer 102 and lower laminate layer 104. In another embodiment, the adhesive extends along at least one longitudinal edge of the laminate such that the upper laminate layer is adhered to the lower laminate layer. In other embodiments, upper laminate layer 102 and lower laminate layer 104 may be joined together (i.e., adhered or bonded) such that left edge and right edge are sealed and absorbent layer 106 is partially or totally encapsulated, though, as will be described in the following paragraphs, such joining is generally not necessary since the laminate, when formed into the multi-layer folded absorbent core, does not exhibit open edges that could lead to SAP leakage.

The absorbent laminate according to the present invention may be manufactured according to processes well known to those skilled in the art of absorbent article manufacturing. According to one such process, a roll or sheet of laminate can be made by metering a free-falling curtain of SAP particles and mixing the curtain of SAP particles with hot melt adhesive fibers. This hot melt adhesive fiber curtain can be formed using conventional hot melt spray equipment, such as the UFD applicator head provided commercially by ITW Dynatec in Hendersonville, Tenn.

The resulting mixture is then directed onto a moving substrate (lower layer). A second substrate (upper layer) is directed on top of the SAP-adhesive mixture to form a sandwich structure. The fibrous layer of thermoplastic adhesive may be in at least partial contact with at least one of the particles of the superabsorbent material, the lower composite layer and the upper laminate layer. The fibrous layer of thermoplastic adhesive may form cavities in which superabsorbent material particles may reside, improving the immobilization of the particles. The fibrous thermoplastic layer may bond to the particles of the superabsorbent material, the lower composite layer or the upper composite layer. In certain embodiments, the superabsorbent material may be essentially dispersed throughout the thermoplastic adhesive fibers. The laminate may then be rolled up and/or cut into segments sized for use in an absorbent article. Methods and apparatuses for metering SAP and mixing the SAP with hot melt adhesive are available commercially and known to those skilled in the art.

The laminate of the present invention can also be made to be asymmetrical. "Asymmetry" is defined as the ratio of the weights, or basis weights, of each of the tissue layers with attached SAP that is obtained upon separation of the laminate. For example, SAP asymmetry is equal to a value of 1 when the SAP is equally distributed between the two layers of tissue. Similarly, in a situation in which the laminate has a total basis weight of 133 gsm (e.g., 97 gsm SAP, 34 gsm tissue, and 2 gsm adhesive), the SAP asymmetry would be approximately 5 if the laminate were to separate into layers of 111 gsm and 22 gsm. Asymmetry may be measured by heating a laminate to about 50 C. for about 10 min. and then separating the laminate by peeling the tissue or layers apart and then weighing each side. According to the present invention, SAP asymmetries of greater than about three are preferred, with asymmetries greater than about four being even more preferred. In addition, preferred results are obtained when the "weak side" of the laminate is positioned in an absorbent core, as will be discussed in detail below, to present at the core's surface. One method of manufacturing such asymmetrical laminates involves applying two mixtures of SAP and adhesive fibers, having different SAP and adhesive contents, to the first substrate in two separate layers, one on top of the other.

B. Multi-layer Folded Absorbent Core

According to the present invention these absorbent laminates may be formed into multi-layer folded absorbent cores that provide novel features and improved performance.

FIGS. 2-8, 10 and 13-14 illustrate schematically various embodiments of multi-layer folded absorbent cores according to the present invention. The Figures are exaggerated to better understand the overall structure of the cores and, as such, are for illustrative purposes only and should not be interpreted literally. Specifically, while the Figures show (and the following discussion of FIGS. 2-8, 10 and 13-14 describe) the segments as generally horizontal and vertical, with the horizontal portions perpendicular to the vertical segments, such depictions are to illustrate the general folded core structure, the transition from one segment to another, and the general relationship between the segments, and should not be interpreted to limit the invention. More specifically, while the schematic views, and the following descriptions refer to "vertical" sections, it should be understood that, in application, the depth dimension, or "Z," is more compact (see FIG. 9E as more representative of such a structure) and, thus, the "vertical" sections appear more as a transition area, or rounded folds, between generally horizontal laminate sections. Typical values for the thickness of a single layer of the laminate and the 6-layer folded core are 0.4-0.5 mm and 2.4-3.4 mm, respectively, measured under a pressure of 2.5 g/cm$^2$. A typical value for the depth of the central channel is about 2.5 mm.

Figure 2:
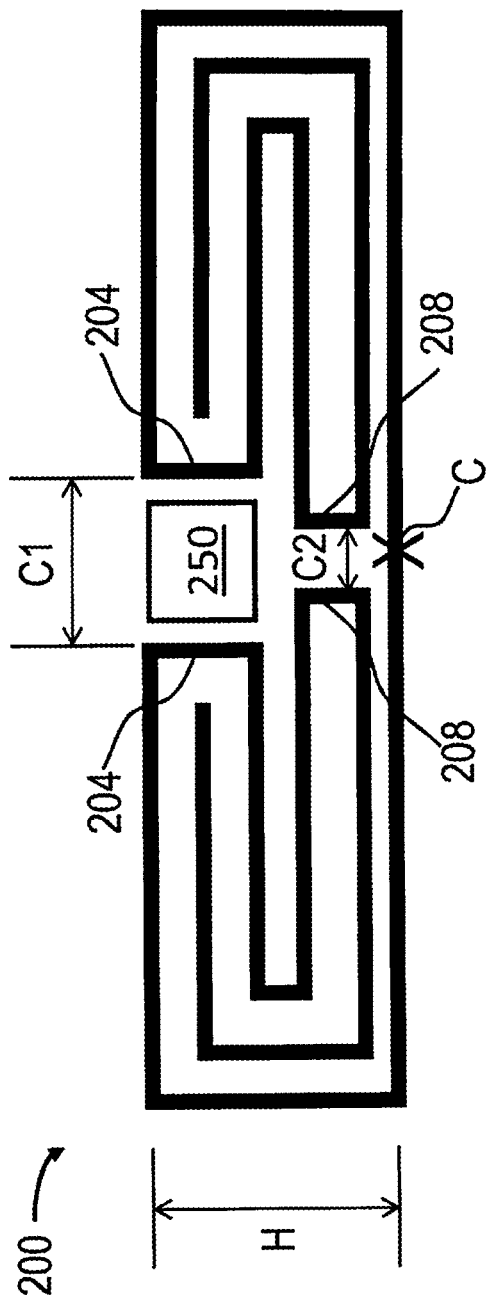
FIG. 2 is a schematic view of a multi-layer folded absorbent laminate according to one aspect of the present invention.

FIG. 2 schematically illustrates one such multi-layer folded absorbent core, in this case a 6-layer folded absorbent core 200. Specifically, FIG. 2 is an end view of a schematic illustration of an embodiment of a 6-layer absorbent core 200 comprising laminate 100 that has been folded to form two halves that are symmetrical relative to longitudinal centerline C and two central channels C1 and C2 that run substantially the length of absorbent core 200 along longitudinal centerline C. The width of channel C1 is shown to be greater than that of C2 in FIG. 2, but the widths of C1 and C2 can also be of comparable dimension. Typical values for the thickness of a single layer of the laminate and the 6-layer folded core are 0.45 mm and 2.9 mm, respectively, measured under a pressure of 2.5 g/cm2. A typical value for the depth of the central channel is about 2.5 mm.

Figure 3:
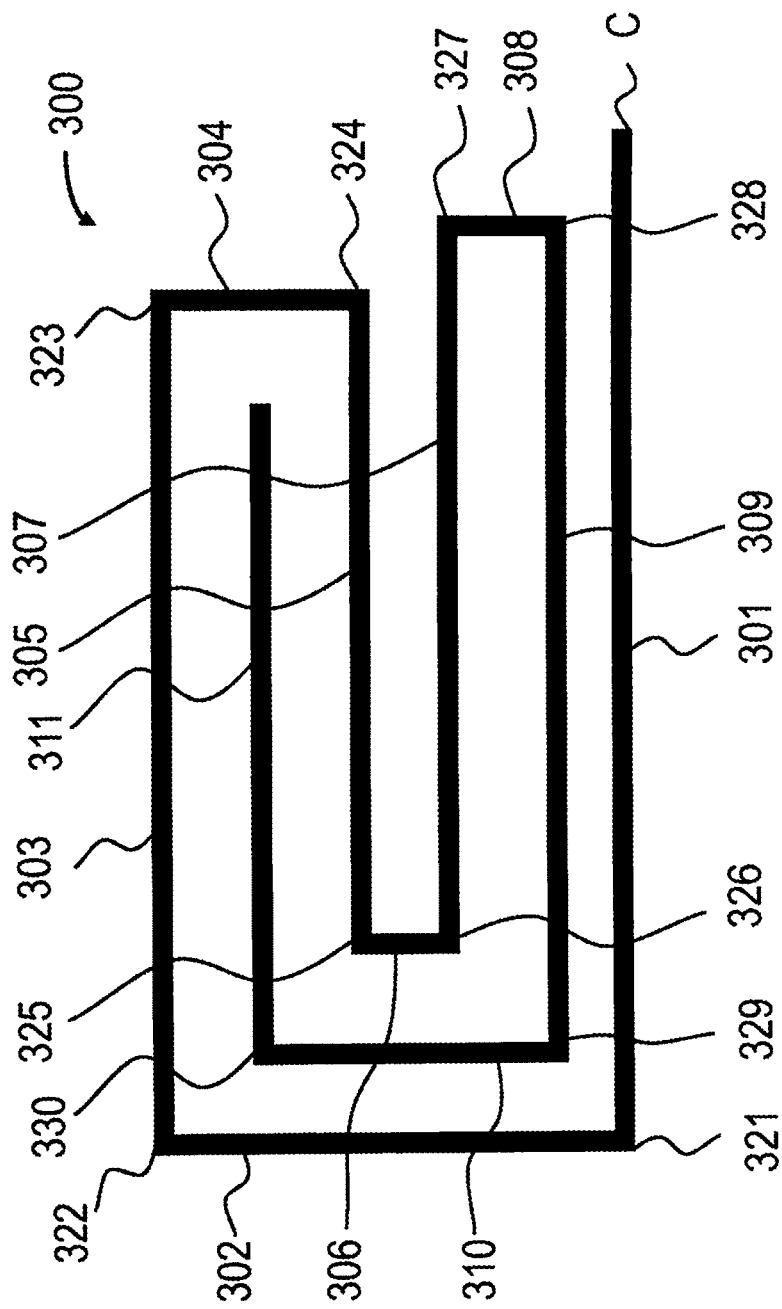
FIG. 3 is a schematic view of one-half of the multi-layer folded core of FIG. 2.

FIG. 3 is a schematic illustration of one-half of 6-layer absorbent core 200 shown in FIG. 2 comprising several horizontal and vertical segments and forming a folded core. By way of illustration only, each half comprises a first horizontal segment 301 adjacent to the longitudinal centerline C, a first fold 321, a first vertical segment 302 adjacent to first horizontal segment 301, a second fold 322, a second horizontal segment 303 adjacent to first vertical segment 302, a third fold 323, a second vertical segment 304 adjacent to second horizontal segment 303, a fourth fold 324, a third horizontal segment 305 adjacent to second vertical segment 304, a fifth fold 325, a third vertical segment 306 adjacent to third horizontal segment 305, a sixth fold 326, a fourth horizontal segment 307 adjacent to third vertical segment 306, a seventh fold 327, a fourth vertical segment 308 adjacent to fourth horizontal segment 307, an eighth fold 328, a fifth horizontal segment 309 adjacent to fourth vertical segment 308, a ninth fold 329, a fifth vertical segment 310 adjacent to fifth horizontal segment 309, a tenth fold 330, and a sixth horizontal segment 311 adjacent to the fifth vertical segment 310.

After folding, the six horizontal segments 301, 303, 305, 307, 309, and 311 form six layers of folded laminate. In certain embodiments, the lengths of the vertical segments are small compared to the lengths of the horizontal segments. Additionally, the vertical segments generally are in the form of fold, curves or transition areas from one generally horizontal segment to another, and not truly vertical segments. This is further schematically illustrated in FIGS. 9A-9D and the description related to these figures.

Other embodiments of an absorbent laminate may be folded substantially as discussed above to form an absorbent core with three, four, or five layers as shown schematically in FIGS. 4-6, respectively. For example, laminate 100 may be folded to form an absorbent core 400 with three vertically-positioned layers (FIG. 4); an absorbent core 500 with four vertically-positioned layers (FIG. 5); and an absorbent core 600 with five vertically-positioned layers (FIG. 6).

FIG. 7 schematically illustrates yet another embodiment of a multi-layer folded absorbent core according to the present invention. This core design provides enhanced liquid transport through the core by providing pathways or crenellations (internal indentations as will be described in following paragraphs) on the out-facing side of the core, in addition to the pathways from the central channel into the laminate. As can be seen, FIG. 7 schematically illustrates a "terraced" structure at both the outer edges and inner edges of each half of the multi-layer folded core. In alternative embodiments, either of the inner or outer edges may have a uniform edge profile while the opposing edge profile is terraced, or both inner and outer edge profiles are uniform.

FIG. 8 schematically illustrates yet another embodiment of a multi-layer folded absorbent core where the opposing terraced edge profile is formed by separate layers of laminate. This core is shown with an optional layer of acquisition material in the center of the core which is wrapped by the separate layers of laminate. The acquisition material can be comprised, for example, of cellulosic or nonwoven acquisition fiber, or DAC materials of the type previously described.

The multi-layer folded absorbent cores described above may be made on standard converting machinery of the type typically used in the manufacture of disposable absorbent articles and the folds themselves may be made using a folding shoe. Other embodiments comprising different numbers of laminate layers are manufactured using this same technique. An example of a typical folding shoe or board used in the industry is described in U.S. Pat. No. 3,401,927, the contents of which are incorporated by reference herein for all purposes and in a manner consistent with this application and invention.

Figure 9A:
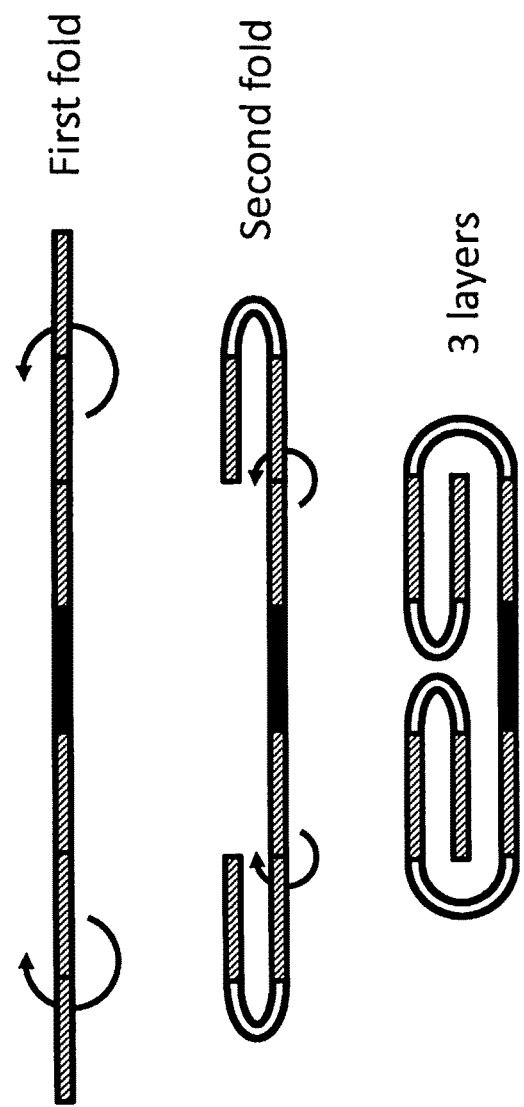

FIGS. 9A-9D schematically illustrate, by way of example, the steps performed when making 3-layer, 4-layer, 5-layer and 6-layer absorbent cores according to the present invention. To create a 3-layer structure, an absorbent laminate is folded two times. An initial 180 degree fold is made towards the center line at an axis at each end of the laminate (FIG. 9A). Then, a second 180 degree fold is made at each end in the same direction as the first fold, at axes closer to the centerline (FIG. 9A, second stage). The resultant structure comprises three layers (FIG. 9A, third stage).

Figure 9B:
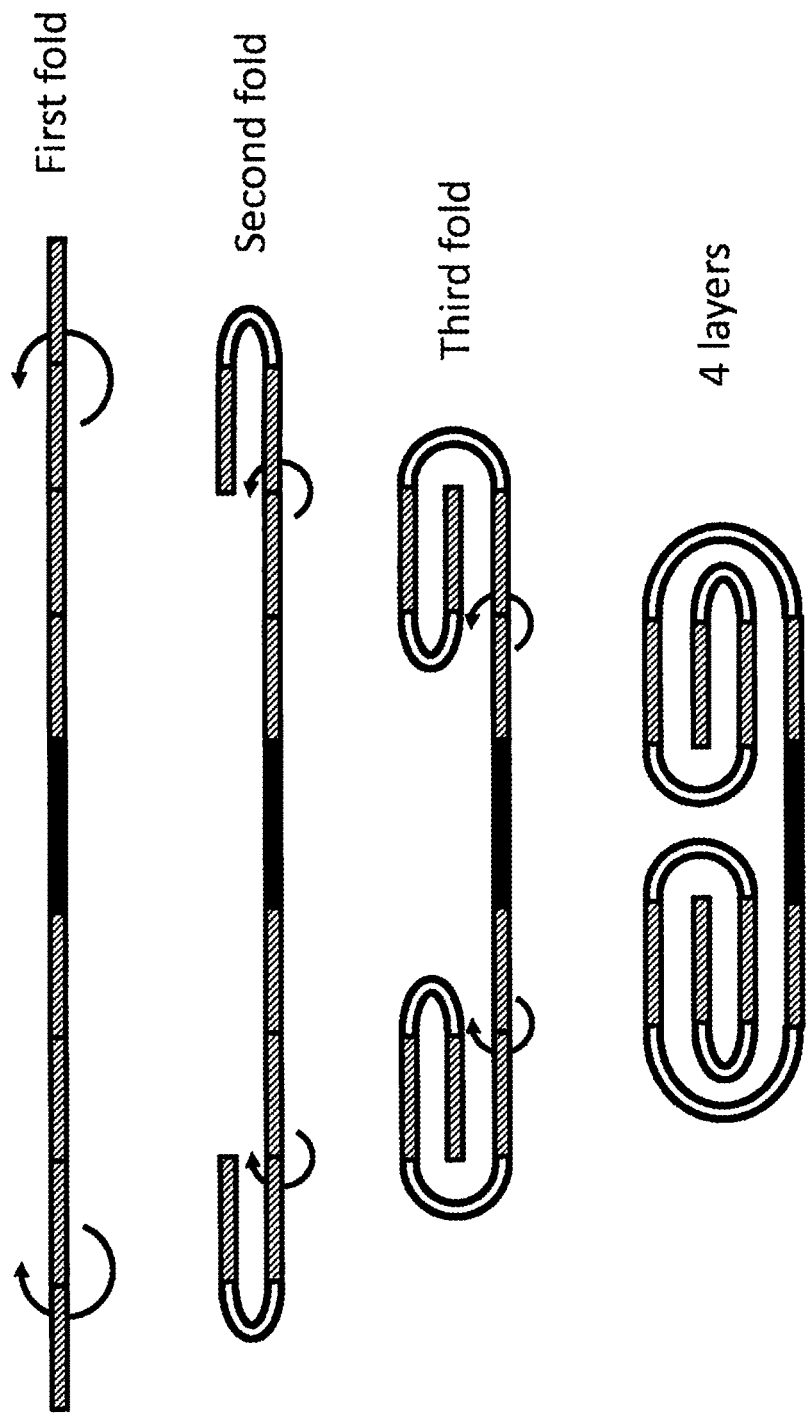

To create a 4-layer structure, an absorbent laminate is folded three times. An initial 180 degree fold is made towards the center line at an axis at each end of the laminate (FIG. 9B, first stage). Then, a second 180 degree fold is made at each end in the same direction as the first fold at axes closer to the centerline (FIG. 9B, second stage). A third 180 degree fold is made at each end in the same direction as the first fold at another axis that is closer to centerline than each second axis fold (FIG. 9B, third stage). The resultant structure comprises four layers (FIG. 9B, fourth stage).

Figure 9C:
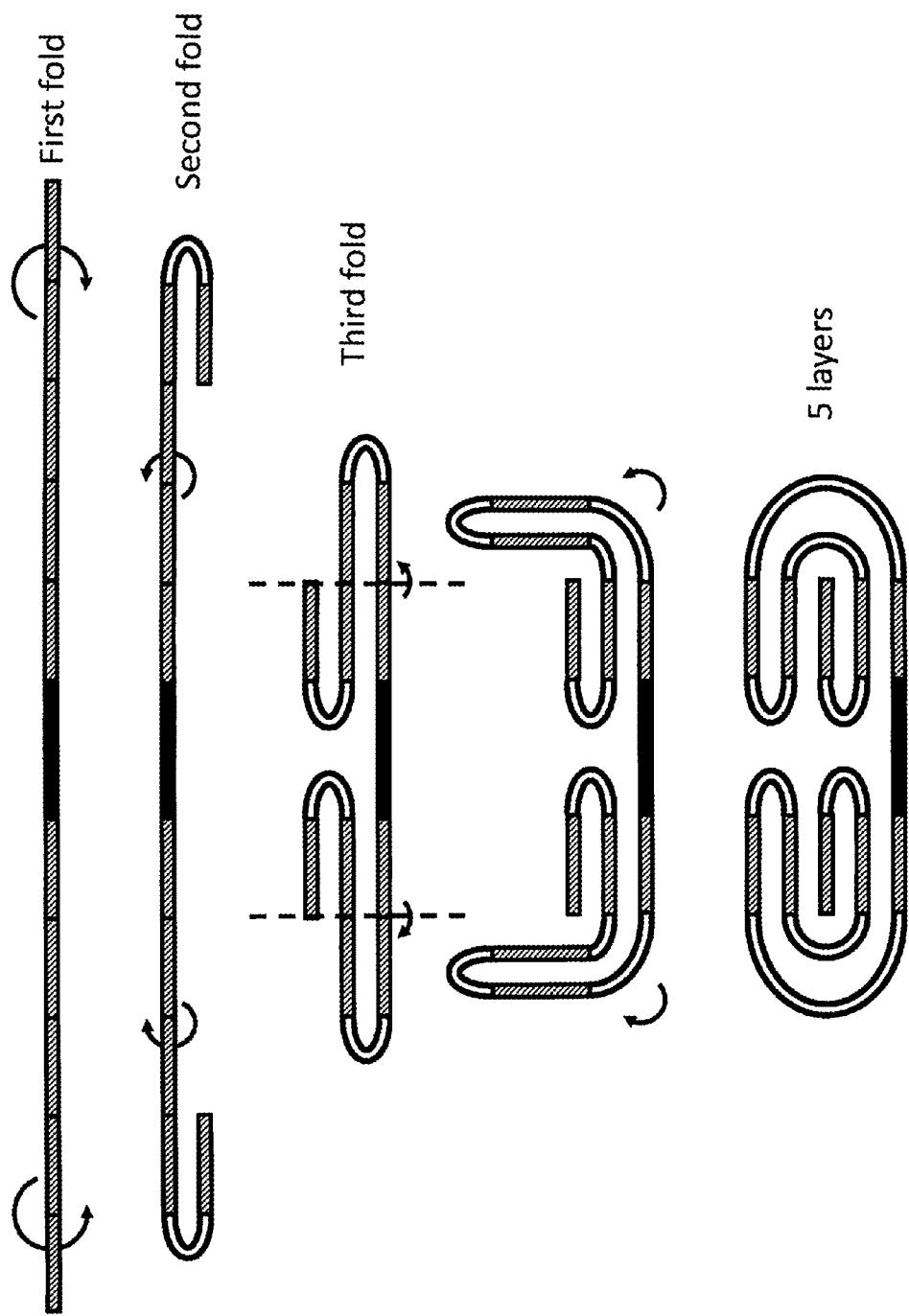

To create a 5-layer structure, an absorbent laminate is folded three times. An initial 180 degree fold is made towards the centerline at an axis at each end of the laminate (FIG. 9C, first stage). Note that the initial fold can be made in either an up-turned or down-turned manner so as to provide different configurations for the final folded core. Then, a second 180 degree fold in the direction opposite to that of the initial fold is made at each end at an axis closer to the centerline of the laminate (FIG. 9C, second stage). The third 180 degree fold is made at the axes defined by the ends of the absorbent laminate, in the same direction as the first fold (FIG. 9C, third stage, dashed lines). The topology of the absorbent laminate structure during the third fold (third fold at 90 degrees) is demonstrated (FIG. 9C, fourth stage). The resultant structure comprises five layers (FIG. 9C, fifth stage).

Figure 9D:
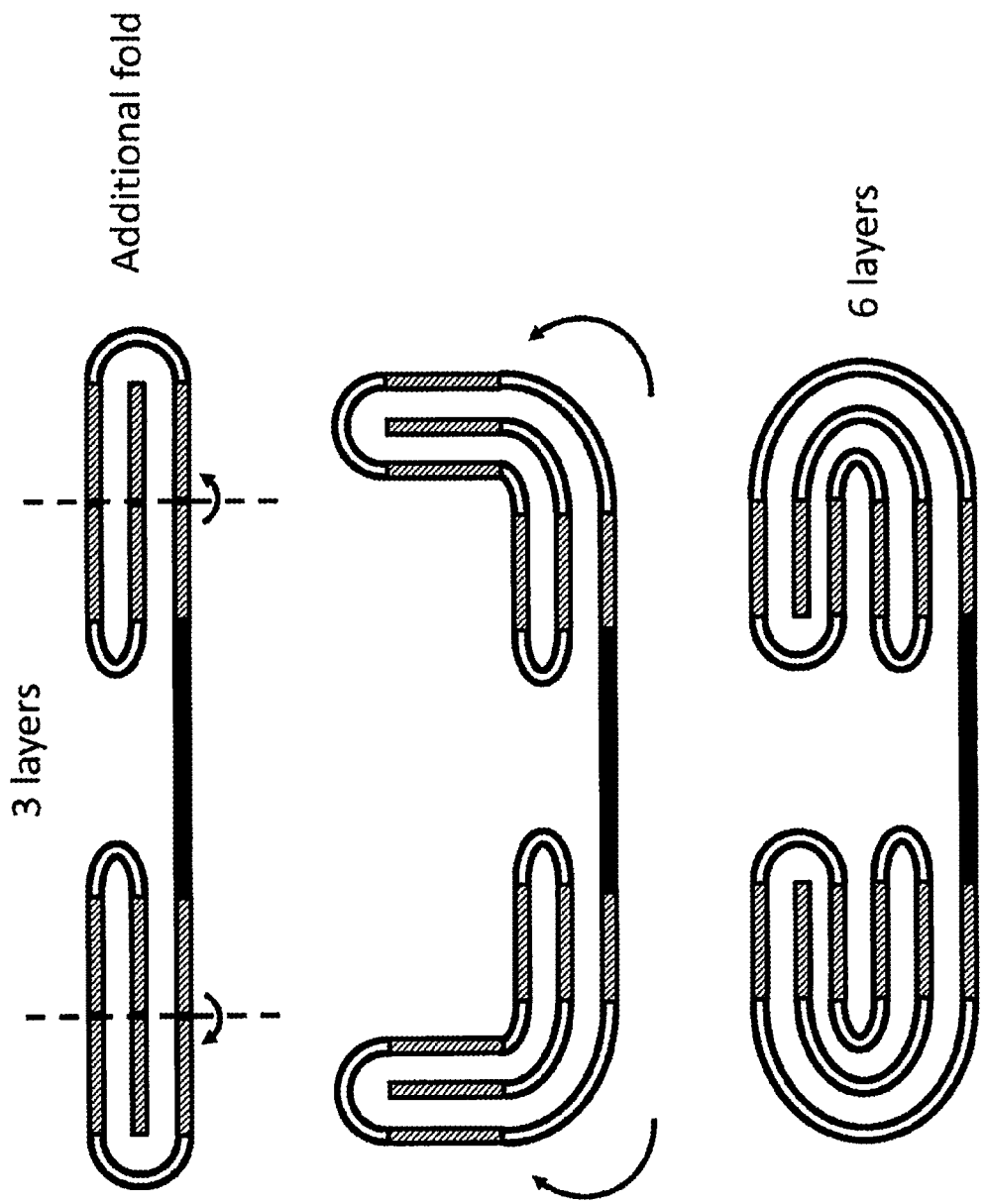

To create a 6-layer structure, a folded 3-layer structure as described above is additionally folded once at each end. An additional 180 degree fold is made at the axis defined by the midpoint of the internal layer at each end, in the same direction as the folds used to create the 3-layer structure (FIG. 9D, first stage, dashed lines). The topology of the absorbent laminate structure during the additional fold (additional fold at 90 degrees) is demonstrated (FIG. 9D, second stage). The resultant structure comprises six layers (FIG. 9D, third stage).

FIG. 9E schematically illustrates the multi-layer folded core of FIG. 9D in its compressed, in use profile.

The multi-layer folded absorbent cores provide significant flexibility to the selection and content of the SAP in the absorbent laminate and, in turn, in the multi-layer folded absorbent core. For example, as discussed above with respect to FIG. 1, laminate 100 may have a SAP basis weight between about 40 gsm and about 150 gsm in some embodiments. Thus, the basis weight of SAP in a multi-layer folded absorbent core comprising six layers may range from about 240 gsm to about 600 gsm. In a preferred embodiment, the laminate has a SAP basis weight of about 60 gsm such that 6-layer absorbent core has a SAP basis weight of about 360 gsm. Alternatively, the multi-layer absorbent cores provides considerable design flexibility for adjusting core structure and an overall SAP basis weight. For example, to make a core with a total SAP basis weight of about 360 gsm, the absorbent laminate layer may have a SAP basis weight of about 120 gsm in a three-layer absorbent core, a SAP basis weight of about 90 gsm in a 4-layer absorbent core, and a SAP basis weight of about 72 gsm in a 5-layer absorbent core.

In certain embodiments, the vertical segments may bow or bend toward or away from centerline C. As mentioned previously, one of skill in the art would understand that a "fold" or "vertical" section is a location of transition between two generally horizontal segments and does not necessarily require a crease or other abrupt transition.

Returning to FIG. 2, the width of the channel(s) may vary along the core's thickness or caliper. In this regard and according to FIG. 2, first channel C1 is formed between opposing second vertical segments 204 and second channel C2 is formed between opposing fourth vertical segments 208. As shown in FIG. 2, first channel C1 may be wider than second channel C2 (C1>C2), providing a central channel with a greater width at the surface of the absorbent core 200; however in other embodiments, first channel C1 may be generally the same width as second channel C2 (C1=C2). In some embodiments of the current invention, the width of second central channel C2 can be <10 mm to provide more absorbency in the center of the core, and the width of first central channel C1 can be greater than one-half of the width of the folded core. When first central channel C1 is wide, acquisition material 250 in FIG. 2 may be a formed pad comprised of cellulosic acquisition fiber. Furthermore, when this pad of acquisition fiber is encased in a core wrap of tissue or nonwoven, and its width is somewhat less than that of central channel C1, additional central channels for liquid absorption can be formed by gaps between the sides of wrapped pad 250 and vertical sections of laminate 204.

Figure 10B:
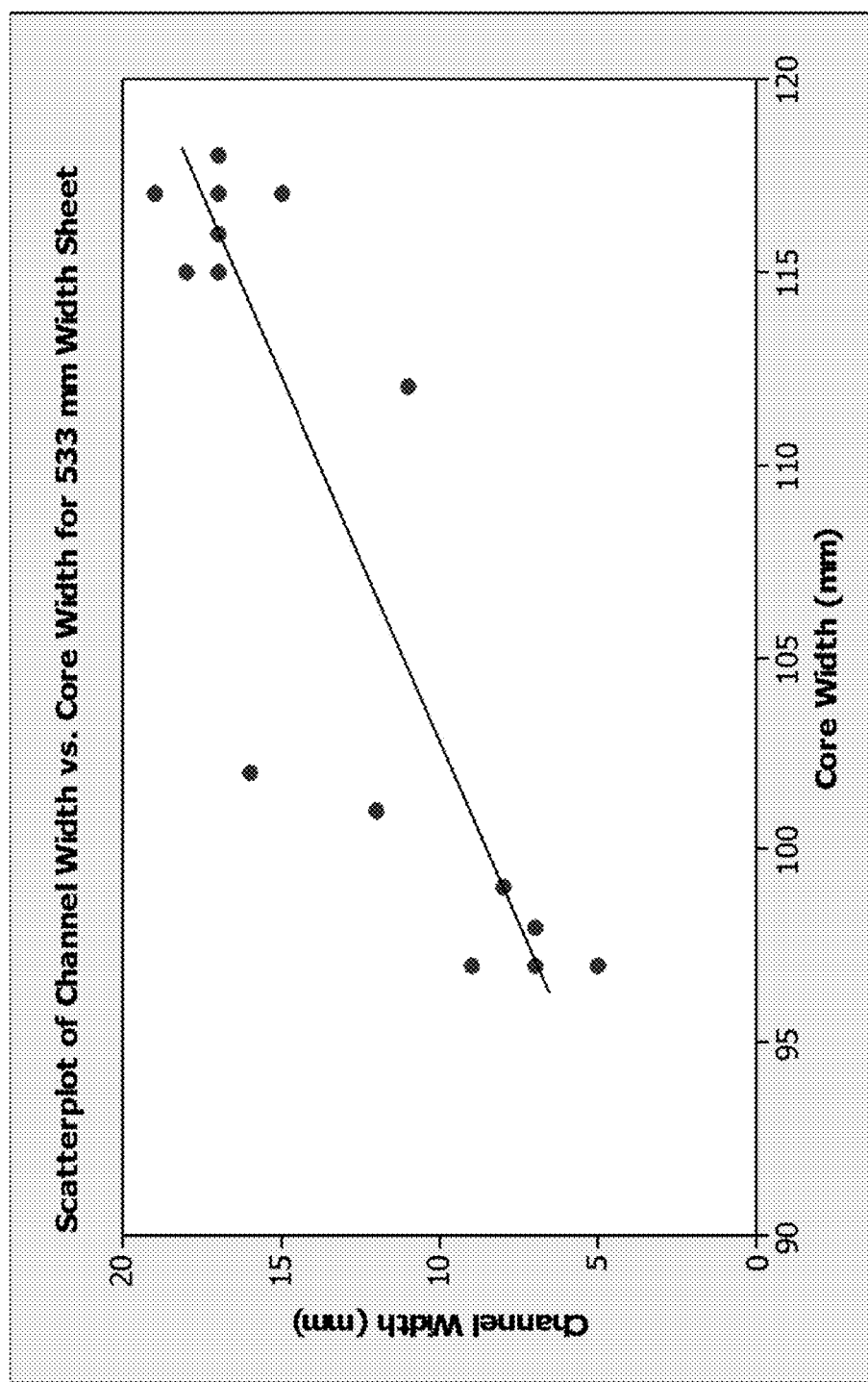

Importantly for purposes of the present invention, the channel should be wide enough so as not to close during swelling of the absorbent laminate. An open channel provides improved and advantageous liquid acquisition time and rewet performance. As known to those skilled in the art, liquid acquisition time is the time for a section of absorbent to absorb a known volume of liquid, typically saline, and rewet is the amount of liquid returned to the surface of the absorbent onto an absorbent filter paper when the absorbent is compressed by an external load. In certain preferred embodiments, the width of first channel C1 and/or second channel C2 should be at least about 2 mm, and more preferably at least about 8 mm. In more preferred embodiments, the channel's width is between about 8 mm and about 50 mm, more preferably, between about 15 mm and about 20 mm. Widths in this range compensate for the occasional "ruck" or overlap between the sides of the channel due in part to pressure applied to the sides of the core by the wearer. Additionally, swelling of the SAP in the laminate during liquid absorption further reduces the width of the channel and, thus, reduces performance. For cores having a folded width of 80-120 mm, the channel should preferably be between about 5% and about 45% of the folded core width and more preferably between about 8% and about 20%. For example, in FIG. 10A, absorbent laminates with a width of 533 mm can be formed into a 5-layer absorbent core of 115 mm width with a central channel width of 10 mm. In this example, the width of the parent laminate is 463% of the width of the folded core. According to another example, an absorbent laminate with a width of 533 mm can be formed into a 6-layer absorbent core of 100 mm width with a central channel width of 9 mm or a 6-layer core of 115 mm width with a central channel width of 15 mm. FIG. 10B shows experimental data for channel width as a function of core width for 6-layer folded cores made with a single layer of laminate that is 533 mm in length.

Also importantly, such a multi-layer folded absorbent core construction increases the surface area of the absorbent laminate 100 that may be exposed to exudates and liquids (i.e., the interfacial area). For example, in certain embodiments, the novel folded geometry of absorbent core 200 provides internal surfaces that provide surface area of at least twice the geometric surface area (i.e., the footprint) of the folded absorbent core. In other embodiments, the interfacial area can be at least three times, at least four times, at least five times, at least six times, or more the geometric surface area.

In addition to the multi-layer folded geometry of the absorbent cores of the present invention, a key feature of the invention involves the improved and unexpected liquid acquisition and distribution provided by the central channel and internal liquid passageways, including crenellations formed by the folding of the absorbent laminate. A liquid passageway refers to any means for liquid movement in the multi-layer core, including the internal crenellations. As noted previously, a crenellation is an internal indentation or crevice for liquid movement. Discussing first the central channel, the central channel provides a mechanism for receiving and containing large volumes of liquid (surges) and directing the bulk flow of liquid both longitudinally along the core and laterally within the core. As a result, core utilization is improved over that of a conventional fluff/SAP core that spreads liquid via a radial wicking mechanism. Furthermore, liquid travel in the inventive core is enhanced by the multiple liquid passageways presented. The internal crevices or interfaces are an important element of such liquid movement. The internal crevices or interfaces further enhance core utilization by moving laterally and longitudinally liquid from the central channel along and between the layers to significantly increase introduction of liquid to the larger interfacial core area. Such a mechanism is not burdened by the slower rate of liquid diffusion through the absorbent laminate in the z (top-to-bottom)-direction. In another advantage of the inventive design, the channels and spaces between the folds create spaces where exudates and liquids may be contained until they can be absorbed into the absorbent layer. Note that 3- and 4-layer folded cores have only one crenellation on each side of the central channel, whereas 5- and 6-layer folded cores in FIGS. 2 and 6 have two crenellations on each side of the central channel. As a result, 5- and 6-layer folded cores generally provide superior liquid acquisition speed as a result of the doubling of this internal surface area. An advantage of the "Christmas tree" fold design, such as the design of FIG. 7, is that it provides multiple crenellations open to the central channel, as well as additional crenellations which are open to the side of the core. An advantage, in general, for multi-layer cores of this invention is that there is much less side leakage, measured in laboratory liquid acquisition/rewet tests, because less liquid moves in a radial pattern at the center of a folded, multi-layer core. Preferably, according to the invention, the central channel or channels and crenellations provide an internal or interfacial surface (the laminate-to-laminate interfaces which provide a path for liquid spreading) that is greater than two times the surface area of the laminate without the channel(s) and crenellations.

To determine the impact on liquid acquisition and distribution of the central channel(s) and crenellations, a demand absorbency experiment was performed to compare a 6-layer folded core with crenellations and a central channel to 6-layers of the same absorbent laminate without crenellations and central channel. Demand absorbency is measured using a Gravimetric Absorbency Test System (GATS). According to this test protocol, a 60 mm diameter sample was cut from an absorbent core. Such cuts were made using a circular die and a clicker press, for example. During a measurement, a sample was restrained by a 60 mm diameter section of rigid tubing. A positive hydrostatic tension of about 1 mm was provided through a 5 mm single aperture centered in a solid plate. The sample was centered on the plate over the aperture under a load providing a pressure of 0.3 psi. Results were expressed as g/g of sample as a function of time. Rates of absorption were calculated from the slopes of this absorption curve. The results of the demand absorbency test are shown in FIG. 11. As a result of liquid spreading within the interior of the core via the crenellated surfaces connected to the central channel, the volume of liquid absorbed by the folded core with the central channel was greater than 3× the volume of liquid absorbed by 6-layers of the laminate without a central channel and crenellations after 10 minutes.

FIG. 2 also illustrates that the central channel may include an insert 250 to improve liquid acquisition performance and reduce end leakage (it has also been determined that after liquid absorption slows after the first few doses, the insert can impede bulk liquid flow along the central channel to reduce or eliminate leakage from the front or rear of the core through the central channel.) The channel may include two or more inserts in those cases in which the width of the channel changes along the thickness or caliper of the core. The inclusion of an insert or inserts in the central channel may mean that a conventional Acquisition Distribution Layer, or ADL, on the surface of the core is not as important for the multi-layered cores of this invention as it is for conventional fluff/SAP cores and current fluffless cores.

In certain embodiments, channel insert 250 is about the same width as the channel into which it is inserted (i.e., first channel C1 or second channel C2). Additionally, in certain embodiments, channel insert 250 is at least about half the depth of the channel into which it is inserted (i.e., first channel C1 or second channel C2). It is possible to have an insert reside both in the central channel and a portion of an internal crenellation, such that the insert is wider than central channels C1 and C2, but not as wide as the width of the folded core.

The insert can comprise an ADL-like nonwoven insert, which exhibits advantageous properties of acquiring the liquid insult and releasing and distributing the liquid across a broader area. More specifically, channel insert 250 may comprise a through-air bonded, or TAB, ADL, preferably comprised of bicomponent fibers that had been treated with a durable or nondurable hydrophilic surface finish. In other embodiments, channel insert 250 may comprise melt-blown polypropylene or a low-twist yarn. In the case of low-twist yarns, the yarn may be comprised of polyester continuous filament or staple fibers with a durable, or alternatively non-durable, hydrophilic finish and, specifically, may range from about 1000 decitex to about 1500 decitex. In yet another embodiment, the channel insert may be a continuous filament or staple fiber tow or narrow-slit nonwoven carded or spunbond pulled from end of a spool to make a twisted, ribbon-like structure. In one embodiment, the insert is a 60 gsm TAB ADL having a width of between about 5 mm and 15 mm. In an alternative embodiment, the insert may utilize discrete acquisition cell (DAC) technology. As previously noted, Discrete Acquisition Cells can be comprised of compressed cellulosic sponge, creped cellulosic paper, soy bean hulls, and other filler materials that provide free volume for rapid absorption of liquid in thin laminates. The DACs can be incorporated into the crenellations of a folded core or introduced into the core in an absorbent laminate.

In yet further embodiments, channel insert 250 may comprise a cellulosic acquisition fiber. The cellulosic acquisition fiber may further comprise SAP. In preferred embodiments, the cellulosic acquisition fiber comprises no more than about 10% by weight SAP. A layer of cellulosic acquisition fiber could also be placed on the surface of a multi-layer folded core. A conventional (fiber or film) ADL is usually required on the surface of cellulosic acquisition fiber to improved overall dryness of the core.

In an alternative folding geometry according to the present invention, the multiple folded core may be inverted with the opening of the central channel facing away from the wearer. A single layer of laminate covering the central channel with the core in an inverted position has sufficient porosity for the central channel and absorbent core to provide rapid liquid acquisition and spreading.

In still yet another embodiment, a sprayable adhesive, a wet-strength resin, or other material could be applied selectively to the outer edges of a multi-layer core to impart wet strength to the tissue.

In yet another embodiment as shown in FIG. 12 and FIG. 8, a multiple-layer absorbent core is achieved by stacking multiple laminates, which are then folded into a C-fold configuration. In a certain embodiment, the single-step C-folding of the stacked multiple laminates, each with identical dimensions, achieves a tapered central channel as shown in FIG. 12. This embodiment is beneficial as the folding occurs in a single step and has the added benefit of suppressing the feel of the edges of the channel as the channel is only three layers thick and the edges taper outwardly. In addition, the wider opening of a tapered or terraced central channel helps liquid to flow into the interior of the core when that liquid impinges the surface of the core at a distance from the center of the open channel.

C. One-Part and Two-Part Multi-Layer Folded Cores

Turning now to another aspect of the invention, the multi-layer folded core according to the present invention may be used as the sole absorbent core in an absorbent article (a "One-Part" core) or may be combined with a second core (a "Two-Part" core). The second core may be a single layer absorbent laminate, one or more other multi-layer folded cores, a conventional (SAP/fluff or fluff only) absorbent core, or combinations thereof. Two-Part cores provide zoned absorbency to increase absorbency in a part of the product where absorbency is needed. Two-Part absorbent cores are well known in the industry for optimization of performance and raw material cost.

FIG. 13, FIG. 14A and FIG. 14B schematically illustrate embodiments of absorbent articles that comprise Two-Part absorbent cores. According to the embodiment shown in FIG. 13, an absorbent article 1000 comprises topsheet 1001, a first multi-layer folded core according to one embodiment of the invention, which will be referred to as a "surge" core 1002, optional channel insert 1003, a second multi-layer folded core according to the present invention, which will be referred to as a "base" core 1004, and a backsheet 1005.

In the illustrated embodiment, surge core 1002 additionally comprises a layer of cellulosic acquisition fiber 1016 positioned above the multi-layer folded core itself to improve liquid acquisition performance. Cellulosic acquisition fiber has a higher Absorption Against Pressure ("AAP") value and a lower Centrifuge Retention Capacity ("CRC") value than that of fluff pulp. AAP and CRC are parameters well known to those skilled in the disposable absorbent article field. The AAP test method is described in EDANA WSP 242.3 (10), and the CRC test method is described in EDANA Test Method WSP 241.2.R3 (12) both incorporated herein by reference. AAP is a measure of an absorbent material's ability to absorb a 0.9% saline solution against a 0.7 psi load. CRC is a measure of the amount of 0.9 wt % saline solution that an absorbent material can retain after free swell and centrifugation to remove bulk interstitial liquid. The acquisition fiber layer 1016 absorbs liquid rapidly, temporarily holds it with capillary tension, and partitions the liquid over time to the core below. Cellulosic acquisition fiber is well known to those skilled in the art. In an alternative embodiment, a layer of cellulosic acquisition fiber can be placed into the central channel to improve liquid acquisition performance. This acquisition fiber, in both cases, can be used with or without SAP and, if SAP is included, levels of about 10% or less are preferred.

In an alternative embodiment, conventional (fiber- or film-based) ADL can be placed on the top surface of the folded surge core to provide additional dryness. Similar to the cellulosic acquisition fiber, the ADL can be folded within a multi-layer folded core to impede rapid spreading of high volumes of liquid in the central channel. Additionally, the ADL can assume a variety of widths and lengths depending on, among other parameters, the core width. In general, ADL widths approximately equal to the width of the multi-layer core, or at least about 95% of the core width, are preferred. FIG. 15 shows an example of the effect of ADL width and length on a 6-layer core made with a laminate containing 97 gsm SAP. When the ADL had a width of 110 mm, i.e., equal to the width of the core, the mannequin leakage performance was good and independent of the length of the ADL over a range of 149-197 mm. However, for an ADL with a narrower width of 90 mm., i.e., only 82% of the core width, mannequin leakage performance became poorer as the ADL length was decreased from 197 to 149 mm.

It also has been determined that placement of an ADL relative to the front edge of the absorbent core (known as "offset") affects overall leakage. In this regard, preferred performance has been discovered when the ADL is offset from the core's front edge. For example, cores according to the present invention exhibited reduced leakage results when the ADL is offset from the core's front edge, by at least about 25 mm and, in some cases, at least about 50 mm or greater.

Absorbent articles, particularly baby diapers, oftentimes include stand-up barrier cuffs that reduce side leakage in use. These cuffs are generally adhered or "tacked down" at their ends to the wearer-side article surface. It has been discovered in accordance with the present multi-layer core design that leakage results are affected by the position of this tack down relative to the core's front edge. Particularly, it has been discovered that improved leakage results are obtained with the novel core designs of the present invention when the barrier cuff is free-standing along the length of the core and is tacked down approximately at the front edge of the core, but not overlaying the core itself.

FIG. 13 also shows schematically that the absorbent cores 1002 and 1004 are enclosed and retained by a wrap material 1012 and 1014. Core wraps are well known in the art and may be constructed from, for example, tissue or nonwoven material. However, because of the excellent core stability of the multi-layer folded cores of the present invention, it will be possible, and in many cases preferable, to use a multi-layer core in an absorbent product without any additional tissue or nonwoven core wrap.

It has further been determined that the leakage performance of cores of the current invention can be improved by selection of a SAP that has an optimal liquid absorption time for the particular dimensions of the core. For example, SAP's with a 0.9% saline absorbency time in the range of about 160 seconds to about 220 seconds provide improved absorbency before leakage in a baby diaper than SAP's with absorption rates below about 160 seconds. A test method used to determine the relevant absorption times of SAP's will be described in a later section.

Additionally, in a preferred embodiment, zoned absorbency may be implemented in a Two-Part core to make efficient use of the absorbent materials. More specifically, in a Two-Part core, the surge layer may be shorter than the base core to provide more absorbent material and absorbency in the area of insult and less core and absorbency in areas of less insult and liquid. For example, in a specific embodiment, the base core may be about 80 to about 120 mm wide and about 345 to about 400 mm long, while a surge core may be about 80 to about 120 mm wide and about 215 to about 260 mm long. In yet another embodiment of a Two-Part core, shown in FIG. 14B, the partial length surge core is comprised of a folded, multi-layer core (in this example a 6-layer core) that has a folded width that is about 20 mm less than the width of the central channel formed by a folded, multi-layer core (in this example a 3-layer core) of the lower, full length base core. This core presents three central channels to a wearer of the absorbent article containing the core. This embodiment is particularly effective at acquiring liquid that might impinge the core to one side of the central channel formed by the surge core and run off to the side of the product, such as when the absorbent article is being used with the subject lying on their side. These configurations are all envisioned to fall within the scope of the present invention.

Also, Two-Part cores can be made with different SAP's in each core. For example, a more permeable SAP may be included in the upper, or surge, core laminate for improved liquid acquisition and a higher capacity SAP may be included in the lower, or base, core laminate for higher liquid capacity. Alternatively Two-Part cores can be made with an upper, surge layer comprised of a multi-layer absorbent core containing a higher capacity SAP and a lower, base layer comprised of a lower capacity, slower absorbing, higher permeability SAP to improve spreading and core utilization. It is advantageous to include acquisition materials and DAC's in the laminates used to make the surge core.

FIG. 14A is a schematic cross-sectional view of another embodiment of an absorbent article 1100 having a Two-Part core. As shown in FIG. 14A, the core comprises topsheet 1101, surge core 1102, channel insert 1103, and backsheet 1105. According to this embodiment, the base core 1104 comprises a C-folded layer of absorbent laminate located below surge core 1102. The C-fold will seal the laminate edges to the backsheet under itself and eliminate migration of hydrated SAP from the free ends of the laminate. This, however, is usually not necessary as that SAP is well-constrained within the laminate. An ADL 1106 is located above surge core 1102 and channel insert 1103. In other embodiments, base core 1104 may be a single unfolded layer. In yet additional embodiments, base core 1104 may comprise a mixture of conventional fluff and SAP, or may comprise only conventional fluff.

Similar to Two-Part cores, a One-Part core would include the standard topsheet and backsheet, and possibly an ADL, as schematically illustrated in FIG. 13 and FIG. 14A for Two-Part cores, however, obviously utilizing only one multi-layer absorbent core. Such one-part cores may offer better manufacturing on a converting machine.

In both One-Part and Two-Part absorbent cores, the geometry and dimensions of the core or cores may vary. For example, in an embodiment configured for use in a baby diaper, a One-Part core may be between about 200 mm and about 450 mm, preferably between about 345 mm and about 385 mm, long, between about 60 mm and about 120 mm, preferably about 110 mm wide, and between about 2 mm and about 6 mm, preferably about 3.1 mm in thickness or caliper. In a preferred embodiment of a Two-Part core, the upper surge core is from about 215 mm to about 245 mm long. The folded width of the surge core would be about 100 mm wide and about 3.8 mm in thickness or caliper. The base core is from about 345 mm to about 385 mm long and from about 100 mm to about 120 mm wide. The lower base core of this preferred embodiment could be made from either a folded laminate or a single layer of unfolded laminate. The preferred thickness or caliper of combined upper and lower cores of this Two-Part core would be about 4 mm.

The folded core of the present invention is in most embodiments greater than 2 mm in thickness. It is formed, however from a material that is much thinner. By way of example, a 1066 mm diameter roll of the laminate will yield at least 3100 lineal meters of material. Such a roll would yield over 8500 cores and, if it were running at a production rate of 400 products per minute, would run for longer than 21 minutes. Roll run time over 15 minutes is considered not unreasonable for those skilled in the art. This would not be possible if the core had to be unwound from a roll in its final thickness and, thus, presents a serious problem for core technologies that require that cores be unwound from their rolls in their final thickness.

Core placement within the absorbent article also is important. Particularly, preferred embodiments place the leading edge of the core within about 30 mm, and preferably less, of the front edge of the diaper chassis. Another relative measure regarding the placement of the core is its location relative to the frontal tape that is often part of an absorbent article's design. Preferably, the leading edge of the core is positioned slightly behind the frontal tape relative to the absorbent article's front edge.

Preferred embodiments for the Two-Part core design, include (a) a 6-layer surge core comprising 45-97 gsm S125D SAP per layer and having a length of 215 mm combined with a single-layer absorbent laminate comprising 89 gsm W211 SAP and having a length of 345 mm; (b) a 5-layer surge core comprising 45-97 gsm W125 SAP per layer and having a length of 215 mm combined with a single layer absorbent laminate comprising 97 gsm W125 SAP and having a length of 385 mm; and (c) a 5-layer surge core comprising 45-97 gsm SA55SX II SAP per layer and having a length of 215 mm combined with a folded, 2-layer absorbent laminate comprising 89 gsm SA55SX II SAP and having a length of 385 mm. In each case, both surge and lower cores have a folded width of about 110 mm and a central channel having a width in the range from about 10 to about 20 mm.

Preferred embodiments for the One-Part core design, include (a) a 6-layer core comprising about 45-97 gsm S125D SAP per layer, (b) a 5-layer core comprising 45-97 gsm W125 SAP per layer, and (c) a 5-layer core comprising 45-97 gsm SA55SX II SAP per layer. The core has a length of from about 345 mm to about 385 mm, a width of about 110 mm, and a central channel width of from about 10 mm to about 20 mm.

The multi-layer folded cores of the present invention may be manufactured using conventional converting equipment. For example, large pancake rolls can be utilized to handle the absorbent laminate, thus avoiding the need for expensive separate processes for spooling or festooning. Similarly, the laminate can be folded in a relatively straightforward process, for example, by use of a folding shoe, or in other ways that will be well known to those skilled in the art. The process experiences little to no SAP loss during conversion because the SAP is confined between tissue or nonwoven layers. Additionally, the process offers ample opportunity to increase line speeds on an off-line laminate process to reduce raw material cost. Alternatively, it may be possible to reduce cost by making the laminate for the multi-layer core on-line.

The multi-layer folded absorbent cores of the present invention and the absorbent products that incorporate these cores present improved and unexpected results when compared with conventional cores. For example, the multi-layer cores exhibit improved liquid acquisition resulting from the central channel, crenellations, high internal surface area, and wicking between adjacent upper and lower layers. Additionally, the cores exhibit good core utilization with the central channel moving liquid in longitudinal and lateral directions and improved core stability and integrity in use.

The cores of the present invention display high SAP efficiency due to the low SAP basis weight in the individual layers of laminate and allow the use of higher capacity SAP's with moderate permeability. More specifically, high absorbency against pressure (AAP) and high SAP efficiency in a multi-layer laminate can be obtained with superabsorbent polymers of higher centrifuge retention capacity (CRC) than can otherwise be used in thin cores without fluff pulp. For example, a preferred SAP may exhibit a CRC value of about 33-38 g/g. Similarly, preferred SAP's exhibit a Saline Flow Conductivity (SFC) value between about 0 and about $10 \times 10^{-7}$ cm$^3$ sec/g. Saline Flow Conductivity, another measure well-known in the disposable absorbent article field and described, for example, in U.S. Pat. No. 5,599,335, measures the permeability of a swollen hydrogel layer.

The multi-layer structure of the absorbent core improves performance of the SAP. For example, six layers of laminate each comprised of 54 gsm of W211 SAP (an absorbent material with a relatively low AAP and high CRC) had an 0.7 psi AAP of 12.9 g/g. Adjusting for the contribution of twelve layers of the tissue in the laminate, the 0.7 psi AAP of the SAP alone was calculated to be 18.3 g/g. The 0.7 psi AAP of an equal basis weight (i.e., 324 gsm) of W211 SAP in a single layer was measured to be only 9.1 g/g. Thus, the 0.7 psi AAP of the SAP was doubled when incorporated into a multilayered core structure. More generally, the 0.7 psi AAP of the SAP in multi-layer absorbent cores according to the present invention is greater than 1.5 times the 0.7 psi AAP of the same total basis weight of SAP in a single layer. The ability to successfully use superabsorbent polymers with relatively low AAP and high CRC in the absorbent cores of this invention contrasts with current pulpless core designs which have used superabsorbent polymers with relatively high AAP, low CRC and high permeability (i.e., SFC>20×10$^{-7}$ cm$^3$ sec/g). A superabsorbent polymer with high values of SFC and 0.7 AAP has a relatively low CRC capacity, and more of this type of SAP will be needed to provide the liquid capacity required of an absorbent core to function.

In addition, the cores have excellent liquid containment, exhibiting no side leakage in testing. The cores offer manufacturing advantages as well. Specifically, they can be produced with moderate run times and by use of simple folding equipment well known in the art. Also, the inventive cores experience manufacturing savings in that they do not require a nonwoven core wrap.

In still another advantage, the multi-layer absorbent cores exhibit decreased thickness or caliper when compared to conventional fluff/SAP cores, as well as newer fluffless cores. This is true even for 6-layer cores according to the present invention. The thinner cores of the present invention have advantages for making more discreet, garment-like absorbent products that require less packaging and can be stored and shipped at lower cost. Caliper measurements of diaper cores, obtained under a restraining pressure of 2.5 g/cm$^2$, are shown in FIG. 16. A One-Part, folded 6-layer core made with a laminate containing 45 gsm of SAP had a thickness of only 3.1 mm. A Two-Part core with an upper layer comprised of 6 folded layers of a laminate containing 60 gsm of SAP and a lower layer comprised of a single layer of laminate containing 89 gsm of SAP had a thickness of 3.8 mm. In both cases, the thicknesses were materially thinner than commercially available products containing a conventional fluff/SAP.

Improved aspects of liquid acquisition and rewet, mannequin leakage performance, and core stability of folded, multi-layer cores will be described in more detail in the Experiments section, which follows.

VIII. EXEMPLARY EMBODIMENTS

Example 1

A laminate was produced by providing a continuous moving substrate of 17 gsm 3995 tissue, which, for example, is commercially available from Dunn Paper in East Hartford, Ct. A first layer of 30 gsm W125 SAP, which, for example, is commercially available from Nippon Shokubai was mixed with 1.3 gsm SP507 hot melt glue fibers, which, for example, is commercially available from Savare in Delaware, Ohio, to form a first mixture. The 1.3 gsm SP507 hot melt glue fibers was dispensed by Uniform Fiber Deposition (UFD) hot melt spray head from ITW Dynatec in Hendersonville, Tenn. A second layer of 70 gsm SAP was mixed with 1.6 gsm hot melt glue fibers to form a second mixture. The second mixture was deposited on top of the first mixture, and a second continuous moving substrate of 3995 tissue was placed on top of the hot melt adhesive. The resulting laminate was wound into a roll and comprised SAP asymmetry exceeding 3:1.

A size 4 diaper was produced using the Example 1 laminate. The laminate was slit to a width of 533 millimeters and folded into a 5-layer core on a commercial diaper machine using folding boards. FIG. 10A depicts one example of the 5-layer core fold that was used in this example. The resulting core comprised a width of approximately 110 mm (e.g., from 90 to 120 mm), a length of approximately 363 mm (e.g., from 350 to 400 mm), and a central channel width of approximately 10 mm (e.g., from 5 to 15 mm). The core was positioned approximately 28 mm from the front of the diaper. The acquisition layer comprised a width of approximately 108 mm and a length of approximately 149 mm. The approximate position of the ADL was 50 mm from the leading edge of the core. The elastic tack down was approximately 10 mm from the leading edge of the core. The end of the elasticated length was approximately 10 mm from the front of the diaper. The Average Mannequin ABL was approximately 243 ml. The remainder of the chassis was the same as the control product that is commercially available with a conventional fluff/SAP core.

Example 2

A laminate was produced in a similar manner to that described in Example 1. A However, a W211 SAP type was used. Further, rather than two plies of substrate, three plies of 3995 tissue was used. Between each tissue layer was disposed a layer of a mixture of 23.5 gsm SAP and 1.3 gsm SP507 adhesive. The Example 2 laminate was made into a diaper in the same or a substantially similar manner as the laminate in Example 1.

One-Part Cores having six layers were constructed with absorbent laminates of 89 gsm S125D SAP and 47 gsm W211 SAP. These six-layer cores were made with a laminate of approximately 385 mm in length and approximately 533 mm in width (e.g., and only approximately 513 mm SAP in width). The width of the folded core was approximately 98 mm, and the width of the central channel was approximately 10 mm. Measured values of AAP were greater than predicted from SAP properties because of a core-structure-induced increase in SAP efficiency. The folded core geometry with the central channel and internal crenellations provided improved core utilization to enhance performance at a reduced level of SAP. An examples of an additional embodiment is depicted in FIG. 16.

IX. EXPERIMENTS

A. Absorbent Laminate
 1. SAP Properties for Optimal Absorbency of Multi-Layer Laminate As discussed in preceding paragraphs, an absorbent laminate of the type described herein has provided evidence of structure-induced improvements in SAP efficiency in a multi-layered absorbent core. Specifically, Absorption Against Pressure (AAP), Capacity (CAP) and Retention Under Load (RUL) were measured for six layers of an absorbent laminate, using the Domtar Personal Care test method described below, and compared to values obtained for a single layer of the same total amount of SAP. The method is a modified version of EDANA WSP 242.3 (10) Worldwide Strategic Partners EDANA (European Disposables and Nonwoven Association, Avenue Eugene Plasky, 157, 1030 Brussels, Belgium, www.edana.com), which is incorporated herein by reference. Six layers of this absorbent laminate at this basis weight provide the necessary absorbency for an infant diaper. According to the test methodology, a "6-layer" sample of a multi-layer laminate was constructed. This 6-layer sample comprised six vertically stacked laminates, each laminate comprised of 0.15 g. SAP and a single layer of tissue placed above and below each layer of SAP. Each sample of multi-layer laminate, therefore, contained a total of 12 layers of tissue and 6 layers of SAP. For comparison, a more typical 1-layer sample was made using the same mass of absorbent materials by placing the total 0.9 g. of SAP between six layers of tissue above and six layers of tissue below the single layer of SAP, as shown schematically in FIG. 17. The more typical 1-layer core structure for a pulpless core is referenced in FIG. 17 as "A" and the 6-layer absorbent laminate structure is referenced as "B."

Pursuant to Domtar Personal Care test method for Absorption Against Pressure (AAP) test, a sample was placed in a holder or cell and tests were performed by following absorption of the samples in 0.9% saline under a load of 0.7 psi, followed by removing the 0.7 psi load and re-weighing the cell and hydrated sample to obtain Capacity (CAP) in an unloaded, free swell condition, then followed by replacing the 0.7 psi load on the hydrated sample in the cell to obtain Retention Under Load (RUL). Saline solution for the tests was purchased from Lab Chem Inc., Cat. No. 07933, which had a specification of 0.9% Wt./Vol.±0.005% sodium chloride. AAP and RUL were measured under a pressure of 0.7 psi, whereas CAP was measured using no load. SAP efficiency was calculated as AAP/RUL×100%. The SAP efficiency was expressed taking into account the contribution of the tissue (measured in a separate experiment) so as to provide a measure of absorbency that can be attributed to the SAP alone, i.e., SAP 0.7 AAP. Values of 4.6 g/g, 6.0 g/g, and 5.0 g/g were used, respectively, for the 0.7 AAP, CAP, and 0.7 RUL of the tissue. Note that 0.7 RUL provides a measure of the maximum possible value of 0.7 AAP, because 0.7 RUL does not depend materially on the permeability of the polymer. The ratio of AAP/RUL, or SAP efficiency, provides a measure of inefficiency in absorption due to a lack of permeability of the sample.

Results are presented in FIG. 18. SAP AAP and SAP efficiency (SAP EFF) for the 6-layer sample increased significantly over that of the 1-layer sample for the SAP's that had mid-range values of permeability, expressed as a Saline Flow Conductivity (SFC) greater than 0 and less than 10 ($\times 10^{-7}$ cm$^3$ sec/g). For example, SAP 0.7 AAP for S125D increased from 14.4 g/g to 23.2 g/g and SAP EFF increased from a value of 48% to 71%. The SAP efficiency of 6-layer samples made with the S125D polymer were significantly increased by the core structure of the present invention, and provided a high value of 0.7 psi AAP.

Centrifuge Retention Capacity (CRC), not measured here, is universally available from manufacturers of superabsorbent polymer. EDANA Test Method WSP 241.2.R3 (12) involves centrifugation of a fully saturated polymer (with 0.9% saline) at a force equal to a centrifugal acceleration of 250±5 G for 3 min.±10 sec. CRC is a good measure of the liquid-holding capacity of a superabsorbent polymer.

Superabsorbent polymers that are preferred for use in a 6-layer laminate are those capable of generating high values of 0.7 AAP at the highest possible value of CRC. Using the AAP test methodology previously described, it has been possible to identify the properties of preferred SAP's for use in a multi-layer core.

Testing of many superabsorbent polymers has shown that the SAP EFF of those SAP's measured in both 1-layer and 6-layer AAP tests decreased, as expected, with increasing CRC [FIG. 19]. SAP EFF decreased with increasing CRC because polymers with high CRC have low gel strength and this leads to the well-known phenomenon of gel blocking under pressure. Further, SAP EFF for the folded 6-layer cores of the present invention was higher than the SAP EFF of a 1-layer core for values of CRC greater than about 30 g/g. The 0.7 SAP AAP of many SAP's in 1-layer and 6-layer cores are shown in FIG. 20. Overall, 0.7 SAP AAP decreased with increasing CRC, but it was possible to identify SAP's that provided a high value of 0.7 SAP AAP (i.e. 28 g/g) at a relatively high value of CRC (i.e. 36 g/g). Comparing SAP's with CRC values of 30 and 36 g/g, it can be seen that it was possible to identify SAP's with a CRC of 36 g/g that provided a 20% increase in CRC with only a 3% decrease in 0.7 SAP AAP. For this reason, SAP's with a high 0.7 SAP AAP and a CRC in the mid-range of 33-38 g/g are preferred for use in a folded, multi-layer core. Other measurements of the liquid-holding capacity of SAP's in a multi-layer cores, CAP and RUL, were found to be mostly independent of CRC over a wide range of CRC [FIGS. 21 and 22].

2. SAP Asymmetry

Examples of SAP asymmetry are shown in FIGS. 23 and 24. SAP asymmetry is the ratio of the weight of the heavier tissue layer and its attached SAP to the weight of the lighter tissue layer and its attached SAP after the layers are gently separated after warming in an oven at about 50° C. for 10 min. FIG. 23 shows SAP asymmetry for nine samples cut from a laminate 533 mm in width. Three of the samples were equally spaced over the cross-direction (CD) of the material and this was repeated at three equally spaced positions in the machine-direction (MD), in a 3×3 matrix. The 533 mm width of material was one-half of the width of parent material at 1066 mm width, thus in FIG. 23, TS indicates the edge of the web and S indicates the center of the web as made on the machine. Samples 1, 2, and 3 were samples cut in the machine-direction at a particular position in the cross-direction. FIG. 23 shows that this laminate was made with relatively low values of SAP asymmetry (i.e., less than a value of 4). There were statistically significant differences in SAP asymmetry in the MD and CD directions. FIG. 24 shows a preferred level of SAP asymmetry for the laminate. Values of SAP asymmetry are all greater than 4 and there are no statistically significant differences in CD and MD directions. Process settings that drive SAP asymmetry can be specific to the web path and geometry of any particular process used to make the laminate and these settings may need to be optimized using standard optimization techniques and designed experiments.

B. Multi-Layer Folded Core Experiments

1. One-Part and Two-Part Multi-Layer Cores Generally

Rapid liquid acquisition over multiple doses, full-length core utilization, minimization of side leakage, and high SAP efficiency are exhibited by One-Part cores comprised of a folded, multi-layer laminate. These attributes are also exhibited by Two-Part cores, where at least one of the parts of the core is comprised of a folded, multi-layer laminate. Two-Part cores provide an effective means to zone absorbent capacity and reduce raw material cost while maintaining key attributes of the folded, multi-layer laminate. The folded multi-layer laminate can be placed in an absorbent article with the open side of the channel facing the wearer or with the open side facing the backsheet of the absorbent article. The latter is possible because a single layer of laminate in the center of a folded, multi-layer core has sufficient permeability to function as an open channel.

2. Rapid Liquid Acquisition for Multiple Doses

A conventional liquid acquisition and rewet test was performed according to the following procedure. The liquid acquisition is the time in seconds for a section of core to absorb a known volume (usually 75 or 100 ml) of 0.9% saline through a 48 mm diameter dosing head. Products were equilibrated overnight and tested in a room maintained at 22° C. and 50% RH. The saline solution was used at a room temperature of 22° C. The dosing head was weighted and had a screen on one end to apply an even pressure of 0.5 psi to the core at the point of liquid dosing. The remainder of the core was restrained under a 150 mm×300 mm plate that weighed 600 g. The dosing head extended through a hole drilled through the core restraining plate and was positioned over the center of the acquisition layer used on the absorbent core. A 75 ml dose was metered to the dosing head at a rate of approximately 20 ml/sec and the time to absorb the liquid was recorded as the acquisition time (±0.1 sec). After 30 minutes of equilibration, the restraining plate was removed, and a stack of ten filter papers (Whatman 4, 70 mm) were placed on the dosing area under a cylindrical brass weight of 60 mm diameter. The weight applied a pressure of 0.8 psi. After two minutes the weight was removed and rewet was determined from a difference in weight between the wet and dry filter papers (±0.01 g.). The acquisition and rewet test was repeated for 4 doses.

Compared to conventional cores, folded cores show improved acquisition times (i.e., the time to absorb a dose of liquid) and rewet after additional doses of liquids and exudates. In conventional cores, the acquisition time tends to rise with each subsequent dose, i.e., the second dose takes longer to absorb than the first dose, the third dose takes longer to absorb than the second dose, and so on. In contrast, the acquisition time for multi-layer absorbent cores according to the present invention falls abruptly after the first dose and stays at a low (good) value for the second, third, and fourth doses.

Liquid acquisition and rewet performance are shown in FIGS. 25A and 25B for a diaper prototype containing a One-Part, 6-layer, folded, multilayer core comprised of a 45 gsm laminate with only 8.9 g. of SAP. Despite the low SAP basis weight, the multi-layer core performed better in lab tests than a premium private label fluff/SAP core containing 9.5 g. of fluff and 11.5 g. of SAP ("Control 1"), and a market-leading "fluffless" diaper containing acquisition fiber and more than 12 g. of SAP ("Control 2"). FIG. 25A shows the characteristic improvement in acquisition time for the folded multilayer core (i.e., 6-45 W211) after the first liquid dose. The fourth dose acquisition time for the folded multilayer core is only 10 sec., compared to remarkably poorer values of 30 sec. for Control 1 and 24 sec. for Control 2. These results are statistically significant at 95% confidence. Fourth dose rewet of the folded multilayer core, shown in FIG. 25B, is better than that of the premium conventional fluff/SAP core and comparable to that of Control 2. Absorbent cores with less than 0.5 g. of rewet are generally "dry" to the touch.

In addition, to illustrate the advantages of the folded, multi-layer core design, the liquid acquisition and rewet performance of a 6-layer core containing a central channel was compared to a 6-layer core without a central channel FIGS. 26A and 26B. FIG. 26A shows the acquisition times for a One-Part, 6-layer, folded core (100 mm width) comprised of a laminate made with 60 gsm of S125D SAP and an unfolded core (i.e., NO FOLD) comprised of six stacked (i.e., unfolded) layers of the same laminate. The data on the right side of FIG. 26A show that acquisition times for a core constructed with unfolded layers of the laminate without a central channel increase with each dose, as the acquisition times do for conventional fluff/SAP cores. Furthermore, as shown in FIG. 26B, rewet for the folded core with a central channel is better than that of core made with the unfolded layers of laminate. This illustrates the advantages of the folded core and a central channel geometry with the laminates of the present invention. A 6-layer core without a central channel has no mechanism for containing large volumes of liquid and directing the bulk flow of liquid both longitudinally along the core and laterally within the crenellation. As FIG. 26A shows, liquid acquisition time for the 6-layer folded core decreased from 19 seconds to 11 seconds over four 75 ml doses, whereas acquisition for the unfolded core increased from 29 sec to 48 seconds over the four doses. Similarly, as shown in FIG. 26B, the folded core exhibits low rewet over the multiple doses, compared to the unfolded core, which exhibits significantly increased rewet after the fourth dose.

According to additional testing, a liquid acquisition and rewet test was performed on a conventional fluff/SAP absorbent core and on various embodiments of Two-Part absorbent cores according to the present invention. More specifically, each Two-Part core sample comprised a folded, multilayer surge core with either four or six laminate layers and an unfolded base core. The various multi-layer cores comprised varying basis weights and SAP types, according to the table below. As for nomenclature of Samples 2-9, the leading digit signifies the number of layers, the next two digits, such as "60" and "89," signify the SAP gsm and the remaining information, such as "S125D" and "W211" signifies SAP type.

| NO. | Surge Core (80 mm × 215 mm) | | | Unfolded Base Core (80 mm × 345 mm) | |
|---|---|---|---|---|---|
| | Layers | Unfolded Laminate Basis Weight (gsm) | SAP type | Unfolded Laminate Basis Weight (gsm) | SAP Type |
| 1. | Conventional Fluff/SAP ("Control") | 558 | | | |
| 2. | 6 | 60 | T9030 | 60 | T9030 |
| 3. | 4 | 89 | T9030 | 89 | T9030 |
| 4. | 6 | 60 | W112A | 60 | W112A |
| 5. | 4 | 89 | W112A | 89 | W112A |
| 6. | 6 | 60 | S125D | 60 | S125D |
| 7. | 4 | 89 | S125D | 89 | S125D |
| 8. | 6 | 60 | W211 | 60 | W211 |
| 9. | 4 | 89 | W211 | 89 | W211 |

The surprising and unique results are described below and illustrated in FIGS. 27A-27B. Results in FIGS. 27A and 27B were obtained using Two-Part cores comprised of a partial 215 mm length upper layer of 4- and 6-layer folded cores containing 60 and 89 gsm of four different superabsorbent polymers. The lower layer of the Two-Part cores was comprised of a single layer (345 mm length) of a laminate of the type used to make the upper core. Both upper and lower layers had a folded width of 80 mm. Compared to a conventional fluff/SAP core containing 9.5 g. of fluff and 11.5 g. of SAP (i.e., Control), the best overall liquid acquisition and rewet performance were obtained for the core that contained an upper core made with 6 folded layers of a laminate containing 60 gsm of S125D SAP (i.e., 6-60 S125D).

As shown in FIG. 27A, for each folded core (samples 2-9) the second dose had a markedly improved (i.e., lower) acquisition time over the acquisition time of the first dose. For most of the folded cores, the acquisition times continued to improve for the third dose (cores 2, 3, 4, 5, 6, 7, and 8). For some of the folded cores, the acquisition times improved even for the fourth dose (cores 2, 3, 4, and 6). The rewet results were better than for conventional fluff/SAP cores and nearly comparable to the best-in-class fluffless cores.

In contrast, the results for the control sample, a conventional premium pulp/SAP absorbent article comprising 9.5 g. fluff and 11.5 g. SAP, and referred to in FIGS. 27A-27B as "Control," reveal that the acquisition time fell very slightly for the second dose, then rose significantly for the third and fourth doses. For the fourth dose of 75 ml, the acquisition times of the folded multi-layer cores were about one-half that of the conventional fluff/SAP core. Further, the results of FIG. 27B show that the novel Two-Part multi-layer folded cores exhibit rewet properties comparable to conventional absorbent articles.

Thus, FIGS. 27A-27B clearly show an advantage for Two-Part cores over a conventional fluff/SAP core in that the inventive Two-Part cores exhibited improved acquisition and faster liquid acquisition for a preferred SAP that had a mid-range permeability and CRC value (i.e., a CRC in the range of 33-38 g/g) as described earlier for optimization of a 6-layer laminate structure. Tests of SAP 0.7 AAP for a 6-layer laminate, discussed in an earlier section, have been used to identify preferred SAP properties for making laminates for a folded, multi-layer core. Particularly, these results were even more pronounced for surge cores comprising 6-layers of absorbent laminate at 60 gsm SAP compared to those comprising 4-layers at 89 gsm. The SAP basis weight of the laminates was adjusted to provide approximately the same amount of SAP in the 6-layer and 4-layer folded cores.

3. Core Utilization

Improved liquid acquisition and rewet performance discussed above for One-Part cores can be understood in terms of improved core utilization of the folded core design over a conventional design. This is shown in FIG. 28, the top half of which reflects liquid spreading for a conventional fluff/SAP core, and the bottom half of which reflects liquid spreading in a multi-layer core according to the present invention. After four liquid doses of 75 ml of a 0.9% saline solution, cores were cut into five equal sections (i.e., from front to back) and weighed to determine the amount of liquid in each section. FIG. 28 demonstrates that liquid spreading was greater in the folded multilayer core. Absorbent material at the ends of the multilayer core was more effectively utilized (evidenced by the more even absorption across the sections) and the amount of liquid in the center of the core relative to the conventional control design was reduced. As FIG. 28 reflects, more than 100 grams of liquid were present in each of Sections 2 and 3 of the fluff/SAP core as a result of limited radial liquid spreading. In contrast, less than 70 grams of liquid were present in each section of the folded multilayer core as a result of liquid spreading by the central channel and crenellations of the core. The control core with excessive liquid in the center or crotch area of the core exhibited about 25 g. of side leakage after the fourth dose. The folded multilayer core exhibited no side leakage in the liquid acquisition and rewet test. Methodology for the measurement of side leakage is described in the next section.

The rate of absorbency of the SAP used in the laminate can be selected to further facilitate effective core utilization. A SAP with an optimal rate of saline absorption will spread evenly in a folded, multi-layer core, providing better core utilization and a lower probability of premature leakage in mannequin testing. It is generally understood that overly rapid absorption of liquid by SAP at the point of dosing should be avoided. If this occurs, the core quickly becomes saturated at the dosing point and bulk liquid spreading on the surface of the core increases the probability of leakage. The effect of SAP absorption rate on mannequin leakage performance will be discussed in a later section.

4. Minimal Side Leakage

A side leakage test was performed in conjunction with the liquid Acquisition and rewet testing for the One-Part and Two-Part cores shown in FIGS. 25A-25B and 27A-27B, respectively. Side leakage can occur by liquid running off of the surface of the core, as well as by moving through the core itself and leaking from the side. In this test, an absorbent bed pad was cut to a width that was 50 mm wider (i.e., 25 mm on each side) than the core and placed under the core samples. At the end of the testing, the bed pad material was re-weighed to determine the amount of side leakage that occurred during the testing. Test results revealed no measurable weight gain in the bedpad, for any of the One-Part and Two-Part cores, thus indicating that the cores did not experience any side leakage. In comparison, conventional fluff/SAP cores had 18-36 g. of side leakage of test liquid after the fourth dose of 75 ml (300 mls total) in this test.

5. Width of Central Channel

It has been discovered, according to the present invention, that the cross-directional width of the central channel should be greater than 2 mm for good liquid acquisition and rewet performance. FIG. 29A shows liquid acquisition times for 6-layer folded cores that had central channel widths of 2 mm, 10 mm, and 25 mm. These were One-Part cores of 100 mm width that were comprised of a laminate containing 60 gsm of S125D SAP. The core that had a central channel width of 2 mm did not exhibit good liquid acquisition performance when compared to the wider channel cores. As discussed above, a 2 mm channel does not provide sufficient free volume for liquid acquisition and can close shut as the core swells with absorbed liquid. The channel width of 10 mm exhibited satisfactory results, but care must be taken that the effective channel width is not decreased because of buckling of the thin section of the core between the folded side areas of the core under conditions of actual use. For this reason, a channel width greater than 15 mm is preferred. The data in FIG. 29A shows a modest reduction (i.e., improvement) in liquid acquisition times for a 25 mm channel relative to that for a 10 mm channel. Improvements in rewet are also observed for cores with central channel widths of 10 mm and 25 mm, compared to one with a central channel width of only 2 mm (FIG. 29B).

It is also possible to adjust the second and third folds of a laminate to make a folded core that has a central channel that is wider at the top and narrower in the interior of the core. Examples of this folding geometry are illustrated in FIGS. 2, 8 and 16. In FIG. 8, the folded core has a terraced central channel comprised of separate layers of laminate. The separate layers can be secured to one another via adhesive or mechanical bonding along the base of the core. In this embodiment, the separate layers of laminate encapsulate an optional acquisition material in the interior of the core. The acquisition material can be comprised of TAB polypropylene or polyester fiber, synthetic fiber tow, low-twist sliver or yarn staple fiber, or cellulosic acquisition fiber.

C. Mannequin Testing of Baby Diapers Containing Folded Multi-Layer Cores

For the mannequin testing, Large Size 4 diapers were constructed to include absorbent cores according to the present invention. These diapers were tested on a Size 4 prone Courtray mannequin diaper tester commercially available from SGS Courtray EURL, Douai, France, using the Courtray absorption before leakage (ABL) protocol provided with the apparatus.

The mannequin is made of a soft silicone rubber and has appropriate dimensions for a Large Size 4 infant. In this test a diaper was fitted to the mannequin and stressed until leakage with multiple doses of 0.9% saline test liquid supplied by Lab Chem Inc., Cat. No. 07933, which had a specification of 0.9% Wt./Vol.±0.005% sodium chloride. Products were equilibrated overnight and tested in a room maintained at 22° C. and 50% relative humidity. The saline solution used was at a room temperature of 22° C. Absorption Before Leakage (ABL) was defined as the mass of liquid that the diaper absorbed (±0.01 g.) under conditions of the test before a leak occurred. Higher values of ABL=(Final Weight of Diaper after Leakage)−(Initial Dry Weight of Diaper) are preferred. The mannequin was provided with female and male dosing tubes. The male mode was used in all tests. The liquid was pumped to the mannequin at a rate of 7 ml/sec using a Masterflex L/S Digital Drive, Model No. HV-07523-80 and a Masterflex L/S Easy-Load II Pump Head, Model No. EW-77200-62. The mannequin was placed on a rectangular foam pad that had a waterproof cover. Leakage was detected visually on a sheet of tissue placed under the mannequin. Times were measured using a stopwatch ±1 sec.

General instructions for fitting a diaper on the mannequin follow. The diaper should be folded in the longitudinal direction forming a pouch, concave inward, between the legs of the mannequin. The standing gathers of the product need to come to rise while applying it to the mannequin, paying close attention to how they lie in the groin. Correct position is achieved when the standing gathers remain extended and surround the male adapter evenly. The outer leg elastics are folded outwardly in the crotch region so that the inner face of the product remains in contact with the skin of the mannequin. The tabs of the diaper are unfolded and put on smoothly. The diaper is spread flatly on front and backside to ensure an even fit. The diaper is then fixed in place with the tape tabs. The tabs should be centered on the landing zone. On a Size 4 Large diaper the ends of the tabs should nearly touch (1 mm±0.5 mm) in the middle of the landing zone. The front and back ends of the diaper should remain at equal height on the torso of the mannequin. Small adjustments can be made to align the front and back ends of the diaper, if necessary. Differences in diaper dimensions can affect the tightness of fit of the diaper around the waist of the mannequin. In the testing described below, folded multi-layer cores were tested in commercially-available diaper chassis.

The protocol for liquid dosing of the product is given in the table below. An initial dose of 75 ml of liquid was delivered at t=0 with the mannequin lying on its belly. At t=4 min. the mannequin was turned on its back. At t=5 min. a dose of 25 ml was delivered with the mannequin lying on its back. At t=9 min. the mannequin was turned onto its belly, rotating the torso in the same direction as turned initially. At t=10 min. a dose of 75 ml was delivered with the mannequin lying on its belly. The mannequin remained on its belly for the remainder of the test and was dosed with 25 ml every 2 min. (e.g., t=12, 14, 16 min., etc.) until leakage occurred. Saline solution that leaks out of the diaper will be absorbed and spread by the tissue layer that covers the pad and will present a visible dark spot. After a leak occurred, the diaper was removed and weighed. The difference between the wet and initial dry weights of the diaper was defined as Absorption Before Leakage (ABL).

| Time (min) | Position | Dose No. | Dose Vol. (ml) |
|---|---|---|---|
| 0 | Belly | 1 | 75 |
| 4 | Back | — | — |
| 5 | Back | 2 | 25 |
| 9 | Belly | — | — |
| 10 | Belly | 3 | 75 |

After 10 min. the mannequin remains on its belly and is dosed with 25 ml every 2 min. until a leak occurs.

The diaper chassis used for making diapers containing the folded, multi-layer cores was a commercially available, private label disposable diaper. Diapers for mannequin testing were created using the following procedure. A 533 mm wide laminate was folded into a multi-layer core (e.g., a 115 mm wide, 5-layer core with a 10 mm wide channel as illustrated in FIG. 10A), and then cut to length (e.g., 300 mm). The diaper was taped flat to a table-top, liner side down, using tape attached to the corners of the diaper as needed keeping the elastics extended. A slit was cut through the centerline of the back sheet along the length of the diaper core. The core was removed through this slit along with any residual fluff adhered to the envelope and the folded, multi-layer core was inserted into the diaper in place of the removed conventional core. The slit in the diaper was neatly closed with tape with sufficient overlap to effectively seal the slit. The diapers were placed on the Courtray mannequin and the ABL was measured and recorded per the procedure supplied by the manufacturer of the mannequin.

1. One-Part and Two-Part Multi-Layer Cores

Folded, multi-layer cores were made with laminates containing S125D and W211 SAP's and compared to commercially available baby diapers in a mannequin leakage test. ABL values measured in these tests are given in the table below.

| BABY DIAPER CORE Size 4, Large | Absorbency Before Leakage or ABL (mean g., n = 4 ± 95% confidence interval) |
|---|---|
| Private label fluff/SAP core | 206 ± 19 |
| Branded, pulpless core No. 1 | 184 ± 33 |
| Branded, pulpless core No. 2 | 259 ± 39 |
| One-Part Folded 6-layer Core (345 mm × 110 mm) Laminate with 45 gsm W211 SAP ADL = 40 gsm TAB (110 mm × 149 mm) | 179 ± 2 |
| One-Part Folded 6-layer Core (345 mm × 110 mm) Laminate with 89 gsm S125D SAP ADL = 40 gsm TAB (110 mm × 149 mm) | 263 ± 17 |
| One-Part Folded 6-layer Core (345 mm × 110 mm) Tri-tissue laminate with 45 gsm W211 SAP ADL = 40 gsm TAB (110 mm × 149 mm) | 195 ± 9 |
| Two-Part Folded Core Upper Part: 6-layer, 60 gsm S125D SAP, 215 mm × 100 mm Lower Part: 1-layer, 89 gsm W211 SAP, 345 mm × 100 mm ADL = 60 gsm TAB (100 mm × 149 mm) | 209 ± 12 |

As the table reflects, One-Part folded, multi-layer cores made with a laminate containing only 45 gsm of SAP (i.e., 8.0 g. of SAP per core) provided adequate mannequin leakage performance at much reduced raw material usage. In comparison, the private label, fluff/SAP core provided similar ABL but contained significantly more (11.5 g.) of SAP. As the table further reflects, One-Part cores with 15.8 g. of SAP (89 gsm of SAP in laminate) and Two-Part cores with 9.7 g. of SAP performed as well or better than the private label, fluff/SAP core and, in the case of the One-Part core, equal to the better performing branded, pulpless core.

2. Width of Central Channel

Additionally, and as mentioned previously, it has been found that it is important to maintain a central channel width in the folded core greater than about 2, and preferably at least about 10, mm for optimum mannequin ABL performance and for liquid acquisition. More preferably, the central channel width should be in the range of about 15 to about 20 mm. As mentioned, channels of these preferred widths compensate for the occasional formation of a "ruck" or overlap in the center of the core at the base of the channel due in part to pressure applied to the sides of the core by the wearer and for swelling of the SAP in the laminate during liquid absorption, which further reduces the width of the channel and reduces performance. The following table records average mannequin ABL values for 5-layer cores made with 100 gsm W125 SAP in the laminate made with the different channel widths indicated. As shown, the ABL results improved with increased channel width.

| Channel Width (mm) | ABL (g) |
| --- | --- |
| 2-4 mm | 215 |
| 5-7 mm | 237 |
| 8-10 mm | 282 |

Pooled Std. Dev. = 8 g

3. Rate of Liquid Absorption of SAP and SAP Asymmetry of Laminate

SAP with an optimal rate of liquid absorption and high levels of SAP asymmetry were shown to improve mannequin ABL performance. First, the mannequin tests confirmed that a core of the present invention using SAP with a moderate absorbency time performed better than one having a shorter absorbency time. Specifically, in the mannequin tests, SAP with a 0.9% saline absorbency time in the range of about 160 sec. to about 220 sec. provided improved mannequin ABL compared to a comparable core made with a SAP with an absorbency time that was less than about 160 sec. FIG. 30 reports these measurements of the time of liquid absorption. FIG. 30 shows that the time of absorption of two different lots of S125D SAP was greater than that of superabsorbent polymers W211 and W125, and that these were statistically significant differences. S125D SAP was found to provide better mannequin leakage performance than W125 in one-part MLC cores when the laminates were made with comparable SAP asymmetry (see table below). All of the cores in the table below were constructed with a core length and width of 345 mm×110 mm and an ADL of 40 gsm TAB nonwoven (149 mm×110 mm) supplied by PGI Polymer Group Inc., Charlotte, N.C. Cores were placed into diapers as described above and tested for mannequin leakage.

| CORE | RATE OF ABSORBENCY OF SAP (sec.) | SAP ASYMMETRY | ABL (g) |
| --- | --- | --- | --- |
| One-Part Folded 6-layer Core Laminate with 89 gsm W125 SAP | 141 | 1.5:1 to 3.5:1 | 169 ± 10 |
| One-Part Folded 6-layer Core Laminate with 89 gsm S125D SAP | 203 | 1.5:1 to 4.0:1 | 246 ± 14 |
| One-Part Folded 6-layer Core Laminate with 89 gsm W125 SAP | 141 | 4.5:1 to 6.5:1 | 259 ± 13 |

SAP absorbency time was measured by placing 0.5 g. (±0.01 g.) of a SAP in a 50 mm diameter disposable aluminum weigh pan, and pouring 15 ml of a 0.9% saline solution over the polymer at a rate of about 5 ml/sec. Temperature of the SAP and saline solution was 22° C. A stopwatch was started during the pouring of the saline solution. After pouring the saline solution into the pan containing the SAP, the pan was swirled gently to provide an even distribution of SAP on the bottom of the pan. When all free liquid on the top of the SAP had been absorbed, a channel was formed in the SAP. Initially water filled the channel, but after repeating this process every two seconds, a point was reached where there was no free liquid on the bottom of the pan to fill the channel. At this point the stopwatch was stopped and the absorption time was recorded.

With regard to asymmetry, all three laminates in the table above were prepared with 89 gsm of SAP, two plies of 17 gsm 3995 tissue as substrates, and 3.2 gsm SP 507 adhesive. Tests were performed to measure SAP asymmetry. The first two laminates in the table above exhibited SAP asymmetry values that averaged well below 4:1 over most of the surface of the sheet. SAP asymmetry values for the second sample above are shown in FIG. 23. The third laminate (FIG. 24) was produced with similar SAP content but with SAP asymmetry values well over 4:1 over most of the laminate.

In considering these results, it should be noted that W125 and S125D SAP's exhibited comparable values of CRC and AAP, but different liquid absorption times. Mannequin absorption before leakage (ABL) for the diapers made with the low asymmetry laminate and the SAP with the shorter absorption time averaged 169±10 g.; n=3. ABL for the diapers made with low asymmetry laminate and the SAP with the longer absorption time of 203 sec. averaged 246±4 g.; n=6. Mannequin leakage performance was better for the core that contained the SAP with the longer absorption time. Without being restricted to any particular theory, it is thought that slower absorbing SAP facilitates more even spreading of liquid in the core, and helps to prevent oversaturation of the core at the dosing point. This oversaturation can inhibit penetration of liquid into the core and allow free liquid to leak from the absorbent product.

Second, turning to SAP asymmetry, it can be shown that a folded multi-layer core made using a laminate that had a value of SAP asymmetry greater than 4 performed better in a mannequin leakage test than a core made using a laminate with a lower value of SAP asymmetry. The mannequin absorption before leakage (ABL) for the diapers made with the low asymmetry laminate and the SAP with the shorter absorption time averaged 169±10 g.; n=3. ABL for the diapers made with the high asymmetry laminate and the same SAP with the shorter absorption time averaged 259±13 g.; n=6. This test showed that an increase in SAP asymmetry of the laminate can improve the mannequin leakage performance of a folded, multi-layer core. This improvement was achieved using a SAP in the laminate that had a liquid absorption rate that was somewhat too low for optimal performance. Laminates made with both the preferred, slower-absorbing S125D SAP and higher SAP asymmetry generated ABL values that were in the range of 240-270 g, i.e., not significantly higher than the values obtained using either the preferred SAP with the longer time of liquid absorption or the laminate with the higher SAP asymmetry alone.

4. Orientation of Laminate in Absorbent Product

Mannequin testing also revealed that, for absorbent articles made with cores of the present invention constructed from laminate material exhibiting significant SAP asymmetry, improved mannequin ABL occurred when the cores were constructed with the side with less SAP bonded to it presented towards the outer surface of the folded core.

5. ADL Width and Diaper Chassis Construction

As part of the mannequin testing, experiments were performed to analyze various additional chassis features of absorbent articles comprising multiple folded cores according to the present invention. Specifically, in preparation for the mannequin diaper trial, certain Designs of Experiments ("DOE") were done to determine the preferred dimensions for several of these chassis features in order to yield the best mannequin performance. These experiments were 4-factor, 2-level DOE's performed with One-Part cores unless indicated otherwise. The results from these DOE's are presented in FIGS. 31 A-C. Specifically, main effects plots for DOE #1 are shown in FIG. 31A. Results indicated better mean values of ABL for: (a) TAB fiber filled vs. unfilled central channel; (b) 110 mm ADL width vs. 65 mm ADL width; (c) Two-Part core vs. One-Part Core; and, (d) 30 min. time between doses vs. 2 min. time between doses. The 30 min. time between doses was a departure from the standard test protocol. Main The table below shows the magnitude of the difference in mannequin leakage performance that was measured for optimized and non-optimized baby diapers according to the factors described above. Channel width remained the same at 10 mm. Both diapers were made with One-Part, folded, 6-layer cores made with a laminate comprised of 89 gsm of S125D SAP.

| Core | Folded Core Width (mm) | ADL Dimensions (l × w) | Core Position (mm from front of diaper) | ADL Offset (mm from front of core) | Standing Gather Tackdown (mm from front of core) | ABL (g.) |
|---|---|---|---|---|---|---|
| ADL and Chassis Not Optimized | 100 | 197 mm × 65 mm | 50 | 25 | 50 | 157 ± 5 |
| ADL and Chassis Optimized | 110 | 149 mm × 110 mm | 26 | 50 | 0 | 246 ± 14 | effects plots for DOE #2 are shown in FIG. 31B. Results indicated better mean values of ABL for: (a) 215 mm ADL length vs. 103 mm ADL length; (b) 110 mm ADL width vs. 65 mm ADL width; (c) 25 mm ADL offset vs. 0 mm offset; and, (d) 0 mm tackdown position vs. 75 mm tackdown position. Main effects plots for DOE #3 are shown in FIG. 31C. Results indicated better mean values of ABL for: (a) no difference between ADL lengths of 149 and 215 mm when ADL width was 110 mm; (b) 50 mm ADL offset vs. 25 mm offset; (c) 0 mm tackdown position vs. 25 mm tackdown position; and, (d) no difference between SAP basis weights (BW) of 45 and 60 gsm.

A preferred diaper design having a number of these features included a five-layer folded core as illustrated in FIG. 10A. The design had a core width of 115 mm, positioned with the leading edge of the folded core about 2 mm from the leading edge of the front tape and about 26 mm from the front edge of the diaper. The ADL was a high-loft Through-Air-Bonded (TAB) nonwoven ADL having a basis weight of 40 gsm and length of 149 mm and a width of about 110 mm with the leading edge of the ADL positioned about 50 mm from the front edge of the core. FIG. 15 presents contour plots generated from designed experiments predicted that mannequin leakage performance would be independent of ADL length (over a range from about 149 mm to about 183 mm) when ADL widths were greater than about 105 mm, or 91% of the absorbent core width. FIG. 15 also shows that mannequin leakage performance improves with ADL length when the ADL width was less than about 100 mm.

It also was found that the standing leg gather should extend to the front of the core with the tack down at this location (i.e., a tackdown position of 0 mm). It further was found that a zone treated top sheet should have a treated hydrophilic zone of a width of about 108 mm. Also, adjustment of the ADL width to nearly equal the width of the core, and the other chassis adjustments mentioned above, were important for achieving the highest levels of mannequin leakage performance of a baby diaper containing a folded, multi-layer core. The ADL in many absorbent products, such as diapers and AI absorbent products, is frequently narrower than the core. The practice of making the ADL as wide as the core for optimum performance for the core of the present invention is a departure from this practice.

It is believed that optimal performance of larger absorbent articles, such as Adult briefs and pull up underwear, and smaller absorbent articles, such as Adult bladder control pads, can be achieved with folded, multi-layer cores by making appropriate changes in chassis design, adjusted for core size.

6. Acquisition Fiber

The mannequin testing results further showed that cellulosic acquisition fiber provided better mannequin ABL performance than TAB nonwoven ADL when used with the folded, multi-layer core of the present invention. Two commercially available diaper products were selected as "controls" for the experiment. The first diaper was a branded diaper product having a pulpless core and the second diaper was a private label diaper having a pulp/SAP core. The core and the ADL of the private label product were removed and the diaper was reconstructed to include the core and ADL of the branded product. Thus, the two commercially available products differed only by diaper chassis. As can be seen from the following table, the branded product exhibited better ABL than the reconstructed private label product. A third control was prepared using the private label chassis and a TAB ADL and a cellulosic fiber/SAP core. This control exhibited ABL inferior to Samples 1 and 2.

Multi-layer core products were constructed to compare to the three controls. Specifically, folded, multi-layer cores were made with laminates containing 45 gsm W211 SAP and 89 gsm S125D SAP and included in the private label chassis. The ABL performance of prototypes made with both the 45 gsm and 89 gsm SAP laminates was improved when a 40 gsm TAB ADL on those cores was replaced with an ADL comprised of about 230 gsm of acquisition fiber and a TAB layer of nonwoven. The folded, 6-layer core made with the 89 gsm S125D SAP and the cellulosic acquisition fiber provided an ABL value of 351±40 g., compared to a value of 259±39 g. for Sample 1. At n=3, this improvement in mannequin leakage performance for the folded, multi-layer core was statistically significant at 95% confidence.

| SAMPLE | CHASSIS | ADL | CORE | ABL (g.) |
|---|---|---|---|---|
| 1 | Branded diaper chassis | Acquisition Fiber and TAB | Branded, pulpless core | 259 ± 39 |

-continued

| SAMPLE | CHASSIS | ADL | CORE | ABL (g.) |
|---|---|---|---|---|
| 2 | Private label diaper chassis | Acquisition Fiber and TAB | Branded, pulpless core | 229 ± 33 |
| 3 | Private label diaper chassis | 60 gsm TAB (197 mm × 65 mm) | Fluff (x g.)/ SAP (11.5 g.) | 206 ± 19 |
| 4 | Private label chassis | 40 gsm TAB (149 mm × 110 mm) | One-Part Folded 6-Layer with 45 gsm W211 SAP in Laminate | 179 ± 2 |
| 5 | Private label chassis | Acquisition Fiber and TAB | One-Part Folded 6-Layer with 45 gsm W211 SAP in Laminate | 225 ± 30 |
| 6 | Private label chassis | 40 gsm TAB (149 mm × 110 mm) | One-Part Folded 6-Layer with 89 gsm S125D SAP in Laminate | 263 ± 17 |
| 7 | Private label chassis | Acquisition Fiber and TAB | One-Part Folded 6-Layer with 89 gsm S125D SAP in Laminate | 351 ± 40 |

D. Core Stability Testing

A laboratory core stability test was developed to provide a measure of the integrity and durability of the core and to simulate its performance in actual use. Fluff/SAP cores can fracture in use and lead to premature leakage. In the Core Stability test a diaper sample was prepared by removing all leg and leg gather elastics along with all side panels. The absorbent core was dosed with 50 ml of a dyed 0.9% saline solution at a point 50 mm forward of the product centerline in the machine direction. After 15 minutes, the product was clamped onto a horizontal supporting rod to hang vertically by the forward end of the article from a single centrally located clamp. The supporting rod and attached product was dropped from a height of 40 mm repeatedly onto hard stops until the absorbent core in the product fractured. The number of drops required to fracture the core was recorded as Core Stability. Four products were tested to obtain a mean value of core stability.

Four commercially available diapers, two branded and two private label, with conventional fluff/SAP absorbent, non-folded cores were selected for the test, along with a One-Part folded, 5-layer core constructed with a laminate containing 97 gsm of SAP. The folded, multi-layer core was produced in a machine-made diaper using a chassis that was comparable to the chassis of one of the private label chassis. All of the diapers with the fluff/SAP cores had a value of core stability in the range of 10 to 33 drops. The folded, multi-layer core was dropped 250 times without any evidence of core fracture. Actual values of mean number of drops and 95% confidence interval of the mean are shown in the table below.

| DIAPER CHASSIS | ABSORBENT CORE | CORE STABILITY (No. of Drops from 40 mm) |
|---|---|---|
| Private label chassis No. 1 | One-Part Folded, 5-Layer 97 gsm SAP Laminate | >250 |
| Private label chassis No. 1 | Fluff/SAP | 33 ± 8 |
| Private label chassis No. 2 | Fluff/SAP | 22 ± 7 |
| Branded chassis No. 1 | Fluff/SAP | 16 ± 7 |
| Branded chassis No. 2 | Fluff/SAP | 11 ± 5 |

The above specification and examples provide a complete description of the structure and use of exemplary embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the present structures and methods are not intended to be limited to the particular forms disclosed. Rather, they include all modifications and alternatives falling within the scope of the claims, and embodiments other than the ones shown or described may include some or all of the features of the depicted or described embodiments. For example, components may be combined as a unitary structure and/or connections may be substituted. Further, where appropriate, aspects of any of the examples described above may be combined with aspects of any of the other examples depicted or described to form further examples having comparable or different properties and addressing the same or different problems. Similarly, it will be understood that the benefits and advantages described above may relate to one embodiment or may relate to several embodiments.

The claims are not to be interpreted as including means-plus- or step-plus-function limitations, unless such a limitation is explicitly recited in a given claim using the phrase(s) "means for" or "step for," respectively.

We claim:

1. An absorbent core comprising a longitudinally folded absorbent laminate, the longitudinally folded absorbent laminate comprising:
    an upper laminate layer;
    a lower laminate layer; and
    an absorbent layer positioned between the upper laminate layer and the lower laminate layer, the absorbent layer comprising greater than about 90 percent by weight super absorbent polymer (SAP);
    wherein the longitudinally folded absorbent laminate is folded to form a longitudinally folded multi-layer absorbent laminate of at least three layers of laminate;
    wherein the longitudinally folded multi-layer absorbent laminate has two lateral laminate sides defined by outermost peripheral folds of the longitudinally folded multi-layer absorbent laminate, and the longitudinally folded multi-layer absorbent laminate has a width extending between the laminate sides, and
    wherein a first one of the layers spans the entire width, a second one of the layers is disposed above the first layer and spans between 80 percent and 92 percent of the width of the longitudinally folded multi-layer absorbent laminate, and a third one of the layers is disposed between the first layer and the second layer and has two portions extending inwardly relative to the laminate sides to inner edges or folds such that the inner edges or folds are separated from one another by a lateral distance of 10 millimeters (mm) or less and the third one of the layers spans more than 92 percent of the width of the longitudinally folded multi-layer absorbent laminate.

2. The absorbent core of claim 1, further comprising a third laminate layer between the upper laminate layer and the lower laminate layer.

3. The absorbent core of claim 1, wherein the longitudinally folded absorbent laminate comprises a channel.

4. The absorbent core of claim 3, wherein the channel extends along the length of the longitudinally folded absorbent laminate and optionally comprises a channel insert.

5. The absorbent core of claim 3, wherein the channel width is from about 2 mm to about 50 mm wide.

6. The absorbent core of claim 3, wherein the channel width is at least about 8 mm wide.

7. The absorbent core of claim 1, where at least one of the upper laminate layer and the lower laminate layer comprises tissue.

8. The absorbent core of claim 1, wherein at least one of the upper laminate layer or the lower laminate layer comprises a nonwoven.

9. The absorbent core of claim 1, wherein upper and lower laminate layers are bonded to each other through non-adhesive bonding.

10. The absorbent core of claim 1, wherein the longitudinally folded absorbent laminate further comprises an adhesive between the upper and lower laminate layers.

11. The absorbent core of claim 10, wherein the adhesive basis weight is less than about 10% of the SAP basis weight.

12. The absorbent core of claim 1, the absorbent core further comprising a surge core and a base core, wherein at least one of said surge and base cores comprises a longitudinally folded, multi-layer absorbent laminate.

13. The absorbent core of claim 12, wherein both of said surge and base cores comprise a longitudinally folded, multi-layer absorbent laminate and wherein each of said cores comprises a channel and said surge core is centered over the channel of said base core.

14. The absorbent core of claim 1, wherein the SAP in the absorbent core has a centrifuge retention capacity (CRC) in the range of about 33-38 g/g.

15. The absorbent core of claim 1, wherein the SAP has a mean particle size in the range of about 250 μm to about 350 μm, and wherein less than 10% of the weight of the SAP particles reside in particles that are greater than 500 μm.

16. The absorbent core of claim 1, wherein the longitudinally folded absorbent laminate comprises a single layer of SAP.

17. The absorbent core of claim 1, wherein the absorbent laminate exhibits a 2 ml Free Surface Absorption Time of less than about 10 seconds.

18. The absorbent core of claim 1, wherein the SAP content of each layer of the longitudinally folded multi-layer absorbent laminate is from about 40 gsm to about 150 gsm and wherein total SAP content of the layers of the longitudinally folded multi-layer absorbent laminate is from about 7.4 g. to about 18 g and the total SAP content of the layers of the longitudinally folded multi-layer absorbent laminate is between about 240 gsm to about 600 gsm.

19. The absorbent core of claim 1, wherein the longitudinally folded absorbent laminate exhibits SAP asymmetry.

20. A disposable absorbent article comprising:
a body-facing topsheet;
a backsheet; and
an absorbent core of claim 1.

21. The disposable absorbent article of claim 20, further comprising a through-air bonded (TAB) acquisition distribution layer (ADL) positioned between the topsheet and the absorbent core, wherein the ADL width is at least 80% of folded core width.

22. The disposable absorbent article of claim 20, further comprising a cellulosic acquisition fiber between the topsheet and the absorbent core.

23. The disposable absorbent article of claim 20, wherein the core and the absorbent article are stable and the absorbent article has a stability rating of at least 35 drops.

24. An absorbent core comprising a longitudinally folded multi-layer absorbent laminate the absorbent laminate comprising:
an upper laminate layer;
a lower laminate layer; and
an absorbent layer positioned between the upper laminate layer and the lower laminate layer, the absorbent layer containing SAP;
wherein the absorbent laminate is folded to form a longitudinally folded multi-layer absorbent laminate of at least three layers of laminate;
wherein the longitudinally folded multi-layer absorbent laminate has lateral laminate sides defined by outermost peripheral folds of the longitudinally folded multi-layer absorbent laminate, and the longitudinally folded multi-layer absorbent laminate has a width extending between the laminate sides, and
wherein a first one of the layers spans the entire width, a second one of the layers is disposed above the first layer and spans between 80 percent and 92 percent of the width of the longitudinally folded multi-layer absorbent laminate, and a third one of the layers is disposed between the first layer and the second layer and spans more than 92 percent but less than 100 percent of the width of the longitudinally folded multi-layer absorbent laminate.

25. The absorbent core of claim 24, further comprising:
a channel extending longitudinally along the longitudinally folded multi-layer absorbent laminate;
a first set of laminate layers positioned on one side of the channel and a second set of laminate layers positioned on the other side of the channel; and
a plurality of liquid passageways positioned between the laminate layers.

26. The absorbent core of claim 25, wherein the longitudinally folded multi-layer absorbent laminate has an interior interfacial area for liquid absorption that is greater than one and one half times the surface area of the top surface of the longitudinally folded multi-layer laminate.

27. The absorbent core of claim 25, wherein certain of the liquid passageways open toward the central channel and certain other of the liquid passageways open toward the sides of the longitudinally folded multi-layer laminate.

28. The absorbent core of claim 27, wherein either the passageways that open towards the channel or the passageways that open towards the laminate sides are laterally spaced from one another to form a terraced profile.

29. The absorbent core of claim 25, wherein at least one liquid passageway is positioned between the laminate layers and is open to the channel that is at least 2 millimeters and no greater than about 50 millimeters wide and wherein the laminate when unfolded and generally flat is at least about 150% the width of the longitudinally folded multi-layer absorbent laminate.

30. The absorbent core of claim 29, wherein the at least one liquid passageway of the longitudinally folded multi-layer absorbent laminate positioned between the laminate layers and open to the channel such that liquid flows away from the channel passing radially from the channel into the laminate layers and is comprised of at least four laminate layers on each side of the channel, wherein the longitudinally folded multi-layer laminate when unfolded and generally flat is at least about 345% the width of the folded absorbent laminate.

31. The absorbent core of claim 29, wherein the at least one liquid passageway of the longitudinally folded multi-layer absorbent laminate, positioned between the laminate layers and open to the channel, is comprised of at least two liquid passageways and wherein the longitudinally folded multi-layer absorbent laminate has an interior interfacial area for liquid absorption that is greater than two times the surface area of the top surface of the longitudinally folded multi-layer absorbent laminate.

32. The absorbent core of claim 25, wherein the longitudinally folded multi-layer absorbent laminate is comprised of at least six laminate layers on each side of the channel, wherein the laminate when unfolded and generally flat is at least about 475% the width of the longitudinally folded multi-layer absorbent laminate.

33. The absorbent core of claim 24, wherein the absorbent layer of the laminate of the longitudinally folded multi-layer absorbent laminate comprises an adhesive positioned between the upper laminate layer and lower laminate layer holding the upper and lower laminate layers together.

34. The absorbent core of claim 24, wherein the longitudinally folded multi-layer absorbent laminate has incorporated therein free volume articles.

\* \* \* \* \*

UNITED STATES PATENT AND TRADEMARK OFFICE
CERTIFICATE OF CORRECTION

PATENT NO.       : 9,789,012 B2
APPLICATION NO.  : 14/634718
DATED            : October 17, 2017
INVENTOR(S)      : Chmielewski et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 38 days.

Signed and Sealed this
Twenty-fifth Day of September, 2018

Andrei Iancu
*Director of the United States Patent and Trademark Office*